United States Patent
Finck et al.

(10) Patent No.: US 11,253,508 B2
(45) Date of Patent: Feb. 22, 2022

(54) PPARγ AGONIST FOR TREATMENT OF PROGRESSIVE SUPRANUCLEAR PALSY

(71) Applicant: Coherus Biosciences, Inc., Redwood City, CA (US)

(72) Inventors: Barbara Finck, San Francisco, CA (US); David E. Weinstein, Dobbs Ferry, NY (US); Sarita K. Jain, Sunnyvale, CA (US)

(73) Assignee: Coherus Biosciences, Inc., Redwood City, CA (US)

( * ) Notice: Subject to any disclaimer, the term of this patent is extended or adjusted under 35 U.S.C. 154(b) by 289 days.

(21) Appl. No.: 16/497,523

(22) PCT Filed: Apr. 3, 2018

(86) PCT No.: PCT/US2018/025923
§ 371 (c)(1),
(2) Date: Sep. 25, 2019

(87) PCT Pub. No.: WO2018/187350
PCT Pub. Date: Oct. 11, 2018

(65) Prior Publication Data
US 2021/0283121 A1 Sep. 16, 2021

Related U.S. Application Data

(60) Provisional application No. 62/480,838, filed on Apr. 3, 2017, provisional application No. 62/651,653, filed on Apr. 2, 2018.

(51) Int. Cl.
*A61K 31/47* (2006.01)
*A61P 25/28* (2006.01)
*A61K 49/00* (2006.01)

(52) U.S. Cl.
CPC .......... *A61K 31/47* (2013.01); *A61K 49/0004* (2013.01); *A61P 25/28* (2018.01)

(58) Field of Classification Search
CPC .................................................... A61K 31/47
See application file for complete search history.

(56) References Cited

U.S. PATENT DOCUMENTS

| | | |
|---|---|---|
| 4,166,452 A | 9/1979 | Generales, Jr. |
| 4,256,108 A | 3/1981 | Theeuwes |
| 4,265,874 A | 5/1981 | Bonsen et al. |
| 4,917,885 A | 4/1990 | Chiba et al. |
| 5,424,286 A | 6/1995 | Eng |
| 5,431,917 A | 6/1995 | Yamamoto et al. |
| 5,462,928 A | 10/1995 | Bachovchin et al. |
| 5,595,898 A | 1/1997 | Robinson et al. |
| 5,939,560 A | 8/1999 | Jenkins et al. |
| 6,011,155 A | 1/2000 | Villhauer |
| 6,040,145 A | 3/2000 | Huber et al. |
| 6,100,234 A | 8/2000 | Huber et al. |
| 6,107,317 A | 8/2000 | Villhauer |
| 6,110,949 A | 8/2000 | Villhauer |
| 6,124,305 A | 9/2000 | Villhauer |
| 6,166,063 A | 12/2000 | Villhauer |
| 6,172,081 B1 | 1/2001 | Damon |
| 6,200,995 B1 | 3/2001 | De la Brouse-Elwood et al. |
| 6,201,132 B1 | 3/2001 | Jenkins et al. |
| 6,242,422 B1 | 6/2001 | Karanewsky et al. |
| 6,303,661 B1 | 10/2001 | Demuth et al. |
| 6,319,893 B1 | 11/2001 | Demuth et al. |
| 6,380,398 B2 | 4/2002 | Kanstrup et al. |
| 6,395,767 B2 | 5/2002 | Robl et al. |
| 6,407,213 B1 | 6/2002 | Carter et al. |
| 6,413,463 B1 | 7/2002 | Yamamoto et al. |
| 6,432,969 B1 | 8/2002 | Villhauer |

(Continued)

FOREIGN PATENT DOCUMENTS

| CA | 2123128 | 5/1993 |
|---|---|---|
| CA | 2289124 | 11/1998 |

(Continued)

OTHER PUBLICATIONS

Albers et al., "Frontal lobe dysfunction in progressive supranuclear palsy: evidence for oxidative stress and mitochondrial impairment.", J Neurochem., 74(2): 878-81, 2000.
Bacioglu et al., "Neurofilament Light Chain in Blood and CSF as Marker of Disease Progression in Mouse Models and in Neurodegenerative Diseases", Neuron 91: 56-66, 2016.
Berg et al., "The adipocyte-secreted protein Acrp30 enhances hepatic insulin action", Nature Medicine, 7: 947-953, 2001.
Berge et al., "Pharmaceutical Salts", Journal of Pharmaceutical Science, 66, 1-19, 1977.
Bologna et al., "Voluntary, spontaneous and reflex blinking in patients with clinically probable progressive supranuclear palsy.", Brain 132: 502-510, 2009.

(Continued)

*Primary Examiner* — Paul V Ward
(74) *Attorney, Agent, or Firm* — Fish & Richardson P.C.

(57) ABSTRACT

Methods of treatment of progressive supranuclear palsy or its symptoms, with PPARγ agonists, and in particular, the compound of formula (I) known as INT 131: Formula (I). Also provided are methods of treating a subject that include selecting a subject having an elevated level of neurofilament light chain protein in a sample obtained from the subject, as compared to a reference level of neurofilament light chain protein, and administering a pharmaceutical composition including a therapeutically effective amount of a compound of formula (I) to the selected subject.

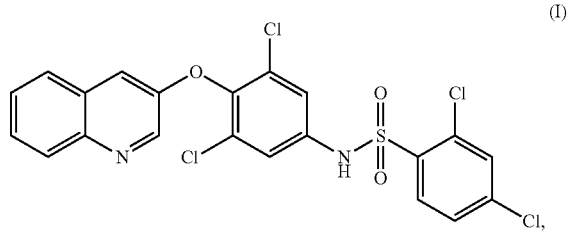

(I)

20 Claims, 2 Drawing Sheets
Specification includes a Sequence Listing.

(56) References Cited

U.S. PATENT DOCUMENTS

| | | |
|---|---|---|
| 6,573,287 B2 | 6/2003 | Sulsky et al. |
| 6,583,157 B2 | 6/2003 | McGee et al. |
| 6,617,340 B1 | 9/2003 | Villhauer |
| 6,645,995 B2 | 11/2003 | Kanstrup et al. |
| 6,649,180 B1 | 11/2003 | Matsuura et al. |
| 6,653,332 B2 | 11/2003 | Jaen et al. |
| 6,699,871 B2 | 3/2004 | Edmondsun et al. |
| 6,706,742 B2 | 3/2004 | De Nanteuil et al. |
| 6,710,040 B1 | 3/2004 | Hulin et al. |
| 6,716,843 B2 | 4/2004 | De Nanteuil et al. |
| 6,727,261 B2 | 4/2004 | Gobbi et al. |
| 6,770,648 B2 | 8/2004 | McGee et al. |
| 6,800,650 B2 | 10/2004 | Boehringer et al. |
| 6,803,357 B1 | 10/2004 | Bachovchin et al. |
| 6,812,350 B2 | 11/2004 | Hulin |
| 6,825,169 B1 | 11/2004 | Bachovchin et al. |
| 6,844,316 B2 | 1/2005 | Niestroj et al. |
| 6,849,622 B2 | 2/2005 | Tanaka et al. |
| 6,861,440 B2 | 3/2005 | Boehringer et al. |
| 6,867,205 B2 | 3/2005 | Boehringer et al. |
| 6,869,947 B2 | 3/2005 | Kanstrup et al. |
| 6,890,898 B2 | 5/2005 | Bachovchin et al. |
| 6,890,905 B2 | 5/2005 | Demuth et al. |
| 6,902,744 B1 | 6/2005 | Kolterman et al. |
| 6,911,467 B2 | 6/2005 | Evans |
| 7,026,316 B2 | 4/2006 | Ashton et al. |
| 7,034,039 B2 | 4/2006 | Oi et al. |
| 7,041,691 B1 | 5/2006 | McGee et al. |
| 7,053,055 B2 | 5/2006 | Demuth et al. |
| 7,060,269 B1 | 6/2006 | Baca et al. |
| 7,060,722 B2 | 6/2006 | Kitajima et al. |
| 7,074,794 B2 | 7/2006 | Kitajima et al. |
| 7,078,281 B2 | 7/2006 | Tanaka et al. |
| 7,078,397 B2 | 7/2006 | Arch et al. |
| 7,084,120 B2 | 8/2006 | Demuth et al. |
| 7,098,239 B2 | 8/2006 | Edmondsun et al. |
| 7,101,871 B2 | 9/2006 | Biftu et al. |
| 7,109,192 B2 | 9/2006 | Hauel et al. |
| 7,115,650 B1 | 10/2006 | Broqua |
| 7,122,555 B2 | 10/2006 | Boehringer et al. |
| 7,125,863 B2 | 10/2006 | Evans et al. |
| 7,125,873 B2 | 10/2006 | Edmondsun et al. |
| 7,132,443 B2 | 11/2006 | Haffner et al. |
| 7,144,886 B2 | 12/2006 | Evans et al. |
| 7,157,490 B2 | 1/2007 | Colandrea et al. |
| 7,166,579 B2 | 1/2007 | Demuth et al. |
| 7,169,806 B2 | 1/2007 | Evans |
| 7,169,926 B1 | 1/2007 | Burgess et al. |
| 7,179,809 B2 | 2/2007 | Eckhardt et al. |
| 7,183,280 B2 | 2/2007 | Himmelsbach et al. |
| 7,183,290 B2 | 2/2007 | Haffner et al. |
| 7,186,731 B2 | 3/2007 | Shima et al. |
| 7,186,846 B2 | 3/2007 | Sharma et al. |
| 7,189,728 B2 | 3/2007 | Evans et al. |
| 7,192,952 B2 | 3/2007 | Kanstrup et al. |
| 7,196,201 B2 | 3/2007 | Haffner et al. |
| 7,205,323 B2 | 4/2007 | Thomas et al. |
| 7,205,409 B2 | 4/2007 | Pei et al. |
| 7,208,498 B2 | 4/2007 | Mathvink et al. |
| 7,217,711 B2 | 5/2007 | Eckhardt et al. |
| 7,223,573 B2 | 5/2007 | Patel et al. |
| 7,223,761 B2 | 5/2007 | Kurk et al. |
| 7,229,969 B2 | 6/2007 | Ansorge et al. |
| 7,230,002 B2 | 6/2007 | Thomas et al. |
| 7,230,074 B2 | 6/2007 | Bachovchin et al. |
| 7,235,538 B2 | 6/2007 | Kanstrup et al. |
| 7,236,683 B2 | 6/2007 | Quan |
| 7,238,720 B2 | 7/2007 | Yasuda et al. |
| 7,238,724 B2 | 7/2007 | Madar et al. |
| 7,241,756 B2 | 7/2007 | Arch et al. |
| 7,253,172 B2 | 8/2007 | Brockunier et al. |
| 7,297,761 B2 | 11/2007 | Beeley et al. |
| 7,368,427 B1 | 5/2008 | Dong et al. |
| 7,601,841 B2 | 10/2009 | McGee |
| 7,626,033 B2 | 12/2009 | McGee et al. |
| 7,754,447 B2 | 7/2010 | Glover et al. |
| 7,939,551 B2 | 5/2011 | Jaen et al. |
| 7,960,408 B2 | 6/2011 | McGee et al. |
| 7,968,567 B2 | 6/2011 | McGee et al. |
| 8,003,665 B2 | 8/2011 | Kurk et al. |
| 8,202,893 B2 | 6/2012 | Makriyannis |
| RE44,512 E | 10/2013 | Glover et al. |
| 9,061,020 B2 | 6/2015 | Weinsten |
| 9,267,164 B2 | 2/2016 | O'Keefe |
| 9,539,249 B2 | 1/2017 | Weinsten |
| 9,675,603 B2 | 6/2017 | Lee et al. |
| 9,867,816 B2 | 1/2018 | Weinsten |
| 9,872,844 B2 | 1/2018 | Zemel et al. |
| 10,772,865 B2 | 9/2020 | Mantzoros |
| 2001/0020006 A1 | 9/2001 | Demuth et al. |
| 2002/0006899 A1 | 1/2002 | Posipilik |
| 2002/0019411 A1 | 2/2002 | Robl et al. |
| 2002/0049164 A1 | 4/2002 | Demuth et al. |
| 2002/0061839 A1 | 5/2002 | Scharpe et al. |
| 2002/0065239 A1 | 5/2002 | Caplan et al. |
| 2002/0071838 A1 | 6/2002 | Demuth et al. |
| 2002/0103384 A1 | 8/2002 | Kanstrup et al. |
| 2002/0110560 A1 | 8/2002 | Demuth et al. |
| 2002/0161001 A1 | 10/2002 | Kanstrup et al. |
| 2002/0165164 A1 | 11/2002 | Demuth et al. |
| 2002/0169185 A1 | 11/2002 | McGee et al. |
| 2002/0183367 A1 | 12/2002 | Sulsky et al. |
| 2002/0198205 A1 | 12/2002 | Himmelsbach et al. |
| 2002/0198242 A1 | 12/2002 | Demuth et al. |
| 2003/0060494 A1 | 3/2003 | Yasuda et al. |
| 2003/0078247 A1 | 4/2003 | De Nanteuil et al. |
| 2003/0087950 A1 | 5/2003 | Nanteuil et al. |
| 2003/0092630 A2 | 5/2003 | Demuth et al. |
| 2003/0096857 A1 | 5/2003 | Evans |
| 2003/0100563 A1 | 5/2003 | Edmondsun et al. |
| 2003/0105077 A1 | 6/2003 | Kanstrup et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0134802 A1 | 7/2003 | Demuth et al. |
| 2003/0136390 A1 | 7/2003 | McGee et al. |
| 2003/0139390 A1 | 7/2003 | McGee et al. |
| 2003/0149071 A1 | 8/2003 | Gobbi et al. |
| 2003/0162820 A1 | 8/2003 | Demuth et al. |
| 2003/0166578 A1 | 9/2003 | Arch et al. |
| 2003/0195188 A1 | 10/2003 | Boehringer et al. |
| 2003/0199528 A1 | 10/2003 | Kanstrup et al. |
| 2003/0216382 A1 | 11/2003 | Boehringer et al. |
| 2003/0216450 A1 | 11/2003 | Evans et al. |
| 2003/0225102 A1 | 12/2003 | Sankaranarayanan |
| 2003/0232788 A1 | 12/2003 | Karanewsky et al. |
| 2004/0034014 A1 | 2/2004 | Kanstrup et al. |
| 2004/0063935 A1 | 4/2004 | Tanaka et al. |
| 2004/0072892 A1 | 4/2004 | Fukushima et al. |
| 2004/0077645 A1 | 4/2004 | Himmelsbach et al. |
| 2004/0082497 A1 | 4/2004 | Evans et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0106655 A1 | 6/2004 | Kitajima et al. |
| 2004/0106656 A1 | 6/2004 | Ashton et al. |
| 2004/0106802 A1 | 6/2004 | Sankaranarayanan |
| 2004/0110817 A1 | 6/2004 | Hulin |
| 2004/0116328 A1 | 6/2004 | Yoshikawa et al. |
| 2004/0121964 A1 | 6/2004 | Madar et al. |
| 2004/0138214 A1 | 7/2004 | Himmelsbach et al. |
| 2004/0138215 A1 | 7/2004 | Eckhardt et al. |
| 2004/0147434 A1 | 7/2004 | Ansorge et al. |
| 2004/0152745 A1 | 8/2004 | Jackson et al. |
| 2004/0167133 A1 | 8/2004 | Edmondsun et al. |
| 2004/0167341 A1 | 8/2004 | Haffner et al. |
| 2004/0171555 A1 | 9/2004 | Demuth et al. |
| 2004/0171848 A1 | 9/2004 | Haffner et al. |
| 2004/0176406 A1 | 9/2004 | Gobbi et al. |
| 2004/0176428 A1 | 9/2004 | Edmondsun et al. |
| 2004/0180925 A1 | 9/2004 | Matsuno |
| 2004/0186153 A1 | 9/2004 | Yasuda et al. |

(56) References Cited

U.S. PATENT DOCUMENTS

| | | |
|---|---|---|
| 2004/0209891 A1 | 10/2004 | Broqua et al. |
| 2004/0224995 A1 | 11/2004 | Simpkins et al. |
| 2004/0229820 A1 | 11/2004 | Bachovchin et al. |
| 2004/0229848 A1 | 11/2004 | Demuth et al. |
| 2004/0229926 A1 | 11/2004 | Tanaka et al. |
| 2004/0235752 A1 | 11/2004 | Pitt et al. |
| 2004/0236102 A1 | 11/2004 | Brockunier et al. |
| 2004/0242566 A1 | 12/2004 | Feng et al. |
| 2004/0242568 A1 | 12/2004 | Feng et al. |
| 2004/0242636 A1 | 12/2004 | Haffner et al. |
| 2004/0242898 A1 | 12/2004 | Hulin |
| 2004/0254226 A1 | 12/2004 | Feng et al. |
| 2004/0259843 A1 | 12/2004 | Madar et al. |
| 2004/0259870 A1 | 12/2004 | Feng et al. |
| 2004/0259883 A1 | 12/2004 | Sakashita et al. |
| 2004/0259902 A1 | 12/2004 | Boehringer et al. |
| 2004/0259903 A1 | 12/2004 | Boehringer et al. |
| 2005/0004117 A1 | 1/2005 | Feng et al. |
| 2005/0004205 A1 | 1/2005 | Evans et al. |
| 2005/0026921 A1 | 2/2005 | Eckhardt et al. |
| 2005/0032804 A1 | 2/2005 | Cypes et al. |
| 2005/0038020 A1 | 2/2005 | Hamann et al. |
| 2005/0043292 A1 | 2/2005 | Parker et al. |
| 2005/0043299 A1 | 2/2005 | Evans et al. |
| 2005/0059716 A1 | 3/2005 | Wagner et al. |
| 2005/0059724 A1 | 3/2005 | Shoenafinger et al. |
| 2005/0065144 A1 | 3/2005 | Feng et al. |
| 2005/0065145 A1 | 3/2005 | Cao et al. |
| 2005/0065148 A1 | 3/2005 | Feng et al. |
| 2005/0065183 A1 | 3/2005 | Nandi et al. |
| 2005/0070530 A1 | 3/2005 | Feng et al. |
| 2005/0070531 A1 | 3/2005 | Feng et al. |
| 2005/0070535 A1 | 3/2005 | Feng et al. |
| 2005/0070706 A1 | 3/2005 | Feng et al. |
| 2005/0070719 A1 | 3/2005 | Belyakov et al. |
| 2005/0075330 A1 | 4/2005 | Feng et al. |
| 2005/0090539 A1 | 4/2005 | Vu et al. |
| 2005/0096348 A1 | 5/2005 | Boehringer et al. |
| 2005/0107309 A1 | 5/2005 | Demuth et al. |
| 2005/0107390 A1 | 5/2005 | Brockunier et al. |
| 2005/0113310 A1 | 5/2005 | Striggow et al. |
| 2005/0130981 A1 | 6/2005 | Aranyl et al. |
| 2005/0130985 A1 | 6/2005 | Himmelsbach et al. |
| 2005/0131019 A1 | 6/2005 | Pei et al. |
| 2005/0137224 A1 | 6/2005 | Shima et al. |
| 2005/0143377 A1 | 6/2005 | Himmelsbach et al. |
| 2005/0143405 A1 | 6/2005 | Boehringer et al. |
| 2005/0143416 A1 | 6/2005 | Kurk et al. |
| 2005/0165989 A1 | 7/2005 | Kim |
| 2005/0171093 A1 | 8/2005 | Eckhardt et al. |
| 2005/0176771 A1 | 8/2005 | Hayawaka |
| 2005/0187227 A1 | 8/2005 | Himmelsbach et al. |
| 2005/0192324 A1 | 9/2005 | Thomas et al. |
| 2005/0203027 A1 | 9/2005 | Bachovchin et al. |
| 2005/0203031 A1 | 9/2005 | Evans |
| 2005/0203095 A1 | 9/2005 | Eckhardt et al. |
| 2005/0209159 A1 | 9/2005 | Demuth et al. |
| 2005/0209249 A1 | 9/2005 | Akritopoulou-Zanze et al. |
| 2005/0215603 A1 | 9/2005 | Akritopoulou-Zanze et al. |
| 2005/0215784 A1 | 9/2005 | Madar et al. |
| 2005/0215882 A1 | 9/2005 | Chenevert et al. |
| 2005/0222140 A1 | 10/2005 | Colandrea et al. |
| 2005/0222222 A1 | 10/2005 | Jiaang et al. |
| 2005/0222242 A1 | 10/2005 | Sharma et al. |
| 2005/0233978 A1 | 10/2005 | Niestroj et al. |
| 2005/0234108 A1 | 10/2005 | Himmelsbach et al. |
| 2005/0234235 A1 | 10/2005 | Eckhardt et al. |
| 2005/0245538 A1 | 11/2005 | Kitajima et al. |
| 2005/0250820 A1 | 11/2005 | Chen |
| 2005/0254167 A1 | 11/2005 | Matsutan et al. |
| 2005/0260712 A1 | 11/2005 | Politino et al. |
| 2005/0260732 A1 | 11/2005 | Hiramatsu et al. |
| 2005/0261271 A1 | 11/2005 | Feng et al. |
| 2005/0272652 A1 | 12/2005 | Gault et al. |
| 2005/0272765 A1 | 12/2005 | Feng et al. |
| 2006/0004074 A1 | 1/2006 | Eckhardt et al. |
| 2006/0014764 A1 | 1/2006 | Feng et al. |
| 2006/0014953 A1 | 1/2006 | Kim |
| 2006/0023870 A1 | 2/2006 | Stenmark |
| 2006/0027022 A1 | 2/2006 | Flora et al. |
| 2006/0039974 A1 | 2/2006 | Akiyama et al. |
| 2006/0040963 A1 | 2/2006 | Mathvink et al. |
| 2006/0046978 A1 | 3/2006 | Pierau et al. |
| 2006/0052382 A1 | 3/2006 | Duffy et al. |
| 2006/0058323 A1 | 3/2006 | Eckhardt et al. |
| 2006/0069116 A1 | 3/2006 | Ashton et al. |
| 2006/0074058 A1 | 4/2006 | Holmes et al. |
| 2006/0074087 A1 | 4/2006 | Ashton et al. |
| 2006/0079541 A1 | 4/2006 | Langkopf |
| 2006/0111336 A1 | 5/2006 | Duffy et al. |
| 2006/0111428 A1 | 5/2006 | Wang |
| 2006/0116393 A1 | 6/2006 | Boehringer et al. |
| 2006/0135512 A1 | 6/2006 | Boehringer et al. |
| 2006/0135561 A1 | 6/2006 | Boehringer et al. |
| 2006/0135767 A1 | 6/2006 | Feng et al. |
| 2006/0142585 A1 | 6/2006 | Thomas et al. |
| 2006/0153940 A1 | 7/2006 | Prous |
| 2006/0154866 A1 | 7/2006 | Chu et al. |
| 2006/0173056 A1 | 8/2006 | Kitajima et al. |
| 2006/0205675 A1 | 9/2006 | Arch et al. |
| 2006/0205711 A1 | 9/2006 | Himmelsbach et al. |
| 2006/0211682 A1 | 9/2006 | Liang et al. |
| 2006/0217428 A1 | 9/2006 | Abrecht et al. |
| 2006/0223870 A1 | 10/2006 | Doken |
| 2006/0229286 A1 | 10/2006 | Kakigami et al. |
| 2006/0247226 A1 | 11/2006 | Himmelsbach et al. |
| 2006/0258646 A1 | 11/2006 | Biftu et al. |
| 2006/0259621 A1 | 11/2006 | Ranganathan et al. |
| 2006/0264400 A1 | 11/2006 | Cambell et al. |
| 2006/0264401 A1 | 11/2006 | Cambell et al. |
| 2006/0264433 A1 | 11/2006 | Backes et al. |
| 2006/0264457 A1 | 11/2006 | Devasthale et al. |
| 2006/0264481 A1 | 11/2006 | Chen |
| 2006/0270701 A1 | 11/2006 | Kroth et al. |
| 2006/0270722 A1 | 11/2006 | Thornberry et al. |
| 2006/0276410 A1 | 12/2006 | Cambell et al. |
| 2006/0276487 A1 | 12/2006 | Aranyl et al. |
| 2006/0281727 A1 | 12/2006 | Ashton et al. |
| 2006/0281796 A1 | 12/2006 | Edmondsun et al. |
| 2006/0293297 A1 | 12/2006 | Fukushima et al. |
| 2007/0016750 A1 | 1/2007 | Suzuki |
| 2007/0021477 A1 | 1/2007 | Edmondsun et al. |
| 2007/0049596 A1 | 3/2007 | Pei et al. |
| 2007/0049619 A1 | 3/2007 | Akahoshi et al. |
| 2007/0060547 A1 | 3/2007 | Cambell et al. |
| 2007/0072803 A1 | 3/2007 | Chu et al. |
| 2007/0072804 A1 | 3/2007 | Chu et al. |
| 2007/0072810 A1 | 3/2007 | Asakawa |
| 2007/0082908 A1 | 4/2007 | Nakahira et al. |
| 2007/0082932 A1 | 4/2007 | Jiaang et al. |
| 2007/0093492 A1 | 4/2007 | Jiaang et al. |
| 2007/0098781 A1 | 5/2007 | Loeffler et al. |
| 2007/0105890 A1 | 5/2007 | Nakahira et al. |
| 2007/0112059 A1 | 5/2007 | Fukushima et al. |
| 2007/0123579 A1 | 5/2007 | Sharma et al. |
| 2007/0142383 A1 | 6/2007 | Eckhardt et al. |
| 2007/0142436 A1 | 6/2007 | Bubendorf et al. |
| 2007/0149451 A1 | 6/2007 | Holmes et al. |
| 2007/0172525 A1 | 7/2007 | Sesha |
| 2007/0185061 A1 | 8/2007 | Cambell et al. |
| 2007/0239536 A1 | 12/2007 | Bollapragada |
| 2007/0293536 A1 | 12/2007 | Kurk et al. |
| 2008/0020046 A1 | 1/2008 | Dawson |
| 2008/0132555 A1 | 6/2008 | Gant |
| 2009/0074862 A1 | 3/2009 | Schioppi |
| 2010/0087481 A1 | 4/2010 | Lee |
| 2010/0104636 A1 | 4/2010 | Kerannidas |
| 2010/0184783 A1 | 7/2010 | Raud et al. |
| 2011/0034380 A1 | 2/2011 | Lanfear et al. |
| 2011/0112097 A1 | 5/2011 | Jaehne et al. |
| 2012/0137162 A1 | 5/2012 | Huang et al. |
| 2012/0322719 A1 | 12/2012 | Pavlov et al. |
| 2013/0243865 A1 | 9/2013 | Lee |
| 2013/0245024 A1 | 9/2013 | Lanfear et al. |

(56) References Cited

U.S. PATENT DOCUMENTS

| | | |
|---|---|---|
| 2014/0107154 A1 | 4/2014 | Filippi |
| 2014/0213612 A1 | 7/2014 | Weinstein |
| 2014/0303018 A1 | 10/2014 | Nikard et al. |
| 2014/0336113 A1 | 11/2014 | Hawiger et al. |
| 2014/0369965 A1 | 12/2014 | Herranz et al. |
| 2014/0377222 A1 | 12/2014 | Huang et al. |
| 2015/0023878 A1 | 1/2015 | Gredes et al. |
| 2015/0051143 A1 | 2/2015 | Harada et al. |
| 2015/0051261 A1 | 2/2015 | Zhao et al. |
| 2015/0224140 A1 | 8/2015 | Komorowski |
| 2015/0238478 A1 | 8/2015 | Insten |
| 2016/0146715 A1 | 5/2016 | Shim et al. |
| 2016/0260398 A1 | 9/2016 | Mantzoros |
| 2016/0287608 A1 | 10/2016 | Carnazza |
| 2017/0143687 A1 | 5/2017 | Weinsten |
| 2017/0273969 A1 | 9/2017 | Lee |
| 2018/0140219 A1 | 5/2018 | Yin et al. |
| 2019/0167660 A1 | 6/2019 | Lanfear |
| 2019/0224186 A1 | 7/2019 | Finck |
| 2019/0298708 A1 | 10/2019 | Jain |
| 2019/0350918 A1 | 11/2019 | Finck |
| 2020/0147036 A1 | 5/2020 | Mantzoros |
| 2020/0383945 A1 | 12/2020 | Mantzoros |

FOREIGN PATENT DOCUMENTS

| | | |
|---|---|---|
| CA | 2289125 | 11/1998 |
| CA | 2339537 | 3/2000 |
| CA | 2353462 | 6/2000 |
| CA | 2433090 | 7/2002 |
| CA | 2466870 | 6/2003 |
| CN | 1440383 | 9/2003 |
| DE | 296075 | 11/1991 |
| DE | 19616486 | 10/1997 |
| DE | 19823831 | 12/1999 |
| DE | 19828113 | 1/2000 |
| DE | 19834591 | 2/2000 |
| DE | 10143840 | 3/2003 |
| DE | 10238243 | 3/2004 |
| DE | 10238470 | 3/2004 |
| DE | 10238477 | 3/2004 |
| DE | 10251927 | 5/2004 |
| DE | 10256264 | 6/2004 |
| DE | 10327439 | 1/2005 |
| DE | 10333935 | 2/2005 |
| EP | 0528858 | 3/1993 |
| EP | 0610317 | 8/1994 |
| EP | 0641347 | 3/1995 |
| EP | 0731789 | 9/1996 |
| EP | 0975359 | 2/2000 |
| EP | 0980249 | 2/2000 |
| EP | 0995440 | 4/2000 |
| EP | 1043328 | 10/2000 |
| EP | 1050540 | 11/2000 |
| EP | 1082314 | 3/2001 |
| EP | 1104293 | 6/2001 |
| EP | 1123272 | 8/2001 |
| EP | 1137635 | 10/2001 |
| EP | 1192137 | 4/2002 |
| EP | 1215207 | 6/2002 |
| EP | 1228061 | 8/2002 |
| EP | 1245568 | 10/2002 |
| EP | 1248604 | 10/2002 |
| EP | 1254113 | 11/2002 |
| EP | 1258476 | 11/2002 |
| EP | 1261586 | 12/2002 |
| EP | 1280797 | 2/2003 |
| EP | 1282600 | 2/2003 |
| EP | 1296974 | 4/2003 |
| EP | 1301187 | 4/2003 |
| EP | 1304327 | 4/2003 |
| EP | 1333025 | 8/2003 |
| EP | 1338592 | 8/2003 |
| EP | 1354882 | 10/2003 |
| EP | 1355886 | 10/2003 |
| EP | 1377288 | 1/2004 |
| EP | 1385508 | 2/2004 |
| EP | 1399154 | 3/2004 |
| EP | 1399420 | 3/2004 |
| EP | 1399433 | 3/2004 |
| EP | 1399469 | 3/2004 |
| EP | 1399470 | 3/2004 |
| EP | 1399471 | 3/2004 |
| EP | 1404675 | 4/2004 |
| EP | 1406622 | 4/2004 |
| EP | 1406872 | 4/2004 |
| EP | 1406873 | 4/2004 |
| EP | 1412357 | 4/2004 |
| EP | 1426366 | 6/2004 |
| EP | 1441719 | 8/2004 |
| EP | 1442049 | 8/2004 |
| EP | 1446116 | 8/2004 |
| EP | 1450794 | 9/2004 |
| EP | 1461337 | 9/2004 |
| EP | 1463727 | 10/2004 |
| EP | 1465891 | 10/2004 |
| EP | 1469873 | 10/2004 |
| EP | 1476429 | 11/2004 |
| EP | 1476435 | 11/2004 |
| EP | 1480961 | 12/2004 |
| EP | 1489088 | 12/2004 |
| EP | 1490335 | 12/2004 |
| EP | 1492777 | 1/2005 |
| EP | 1513808 | 3/2005 |
| EP | 1517907 | 3/2005 |
| EP | 1296967 | 5/2006 |
| EP | 1664278 | 6/2006 |
| EP | 1738754 | 1/2007 |
| EP | 1782828 | 5/2007 |
| EP | 1905450 | 4/2008 |
| EP | 1677797 | 2/2012 |
| EP | 3267994 | 1/2018 |
| EP | 2618827 | 2/2021 |
| FR | 2822826 | 10/2002 |
| FR | 2824825 | 11/2002 |
| JP | 2000191616 | 7/2000 |
| JP | 2000256208 | 9/2000 |
| JP | 2000511559 | 9/2000 |
| JP | 2000327689 | 11/2000 |
| JP | 2007507537 | 3/2001 |
| JP | 2001510442 | 7/2001 |
| JP | 2002516318 | 6/2002 |
| JP | 2002517401 | 6/2002 |
| JP | 2002527504 | 8/2002 |
| JP | 2002265439 | 9/2002 |
| JP | 2002531541 | 9/2002 |
| JP | 2002531547 | 9/2002 |
| JP | 2002356471 | 12/2002 |
| JP | 2002356472 | 12/2002 |
| JP | 2002363157 | 12/2002 |
| JP | 2003520849 | 7/2003 |
| JP | 2003238566 | 8/2003 |
| JP | 2003524591 | 8/2003 |
| JP | 2003300977 | 10/2003 |
| JP | 2003531118 | 10/2003 |
| JP | 2003531191 | 10/2003 |
| JP | 2003531204 | 10/2003 |
| JP | 2003327532 | 11/2003 |
| JP | 2003535034 | 11/2003 |
| JP | 2003535898 | 12/2003 |
| JP | 2004002367 | 1/2004 |
| JP | 2004002368 | 1/2004 |
| JP | 2004026678 | 1/2004 |
| JP | 2004026820 | 1/2004 |
| JP | 2004035574 | 2/2004 |
| JP | 2004043429 | 2/2004 |
| JP | 2004503531 | 2/2004 |
| JP | 2004521149 | 7/2004 |
| JP | 2004522786 | 7/2004 |
| JP | 2004525179 | 8/2004 |
| JP | 2004525929 | 8/2004 |
| JP | 2004244412 | 9/2004 |
| JP | 2004530729 | 10/2004 |
| JP | 2004532220 | 10/2004 |

(56) References Cited

FOREIGN PATENT DOCUMENTS

| | | |
|---|---|---|
| JP | 2004315496 | 11/2004 |
| JP | 2004534815 | 11/2004 |
| JP | 2004534836 | 11/2004 |
| JP | 2004535433 | 11/2004 |
| JP | 2004535445 | 11/2004 |
| JP | 2004536115 | 12/2004 |
| JP | 2005023038 | 1/2005 |
| JP | 2005500308 | 1/2005 |
| JP | 2005500321 | 1/2005 |
| JP | 2005502624 | 1/2005 |
| JP | 2005505531 | 2/2005 |
| JP | 2005507261 | 3/2005 |
| JP | 2010265216 | 11/2010 |
| JP | 2013133312 | 7/2013 |
| JP | 2016506956 | 3/2016 |
| MX | PA06003313 | 6/2006 |
| WO | WO 1991/016339 | 10/1991 |
| WO | WO 1993/008259 | 4/1993 |
| WO | WO 1993/010127 | 5/1993 |
| WO | WO 1995/015309 | 6/1995 |
| WO | WO 1995/029691 | 11/1995 |
| WO | WO 1997/040832 | 11/1997 |
| WO | WO 1998/018763 | 5/1998 |
| WO | WO 1998/019998 | 5/1998 |
| WO | WO 1998/025621 | 6/1998 |
| WO | WO 1998/050046 | 11/1998 |
| WO | WO 1998/050066 | 11/1998 |
| WO | WO 1999/016864 | 4/1999 |
| WO | WO 1999/025719 | 5/1999 |
| WO | WO 1999/056753 | 11/1999 |
| WO | WO 1999/061431 | 12/1999 |
| WO | WO 1999/062914 | 12/1999 |
| WO | WO 1999/067278 | 12/1999 |
| WO | WO 2000/010549 | 3/2000 |
| WO | WO 2000/023421 | 4/2000 |
| WO | WO 2000/034241 | 6/2000 |
| WO | WO 2000/056297 | 9/2000 |
| WO | WO 2000/069868 | 11/2000 |
| WO | WO 2000/071135 | 11/2000 |
| WO | WO 2001/000579 | 1/2001 |
| WO | WO 2001/27128 | 4/2001 |
| WO | WO 2001/034594 | 5/2001 |
| WO | WO 2001/052825 | 7/2001 |
| WO | WO 2001/055105 | 8/2001 |
| WO | WO 2001/068603 | 9/2001 |
| WO | WO 2001/081304 | 11/2001 |
| WO | WO 2001/081337 | 11/2001 |
| WO | WO 2001/096295 | 12/2001 |
| WO | WO 2001/097808 | 12/2001 |
| WO | WO 2002/000633 | 1/2002 |
| WO | WO 2002/002560 | 1/2002 |
| WO | WO 2002/014271 | 2/2002 |
| WO | WO 2002/030890 | 4/2002 |
| WO | WO 2002/030891 | 4/2002 |
| WO | WO 2002/034900 | 5/2002 |
| WO | WO 2002/038541 | 5/2002 |
| WO | WO 2002/051836 | 7/2002 |
| WO | WO 2002/055088 | 7/2002 |
| WO | WO 2002/068420 | 9/2002 |
| WO | WO 2002/062764 | 10/2002 |
| WO | WO 2002/076450 | 10/2002 |
| WO | WO 2002/083109 | 10/2002 |
| WO | WO 2002/083128 | 10/2002 |
| WO | WO 2003/000180 | 1/2003 |
| WO | WO 2003/000181 | 1/2003 |
| WO | WO 2003/000250 | 1/2003 |
| WO | WO 2003/002530 | 1/2003 |
| WO | WO 2003/002531 | 1/2003 |
| WO | WO 2003/002553 | 1/2003 |
| WO | WO 2003/002593 | 1/2003 |
| WO | WO 2003/002595 | 1/2003 |
| WO | WO 2003/002596 | 1/2003 |
| WO | WO 2003/004496 | 1/2003 |
| WO | WO 2003/004498 | 1/2003 |
| WO | WO 2003/015775 | 2/2003 |
| WO | WO 2003/022871 | 3/2003 |
| WO | WO 2003/024942 | 3/2003 |
| WO | WO 2003/024965 | 3/2003 |
| WO | WO 2003/035057 | 5/2003 |
| WO | WO 2003/035067 | 5/2003 |
| WO | WO 2003/037327 | 5/2003 |
| WO | WO 2003/038123 | 5/2003 |
| WO | WO 2003/040174 | 5/2003 |
| WO | WO 2003/045228 | 6/2003 |
| WO | WO 2003/045977 | 6/2003 |
| WO | WO 2003/055881 | 7/2003 |
| WO | WO 2003/057144 | 7/2003 |
| WO | WO 2003/057666 | 7/2003 |
| WO | WO 2003/068748 | 8/2003 |
| WO | WO 2003/068757 | 8/2003 |
| WO | WO 2003/072528 | 9/2003 |
| WO | WO 2003/072556 | 9/2003 |
| WO | WO 2003/074500 | 9/2003 |
| WO | WO 2003/080633 | 10/2003 |
| WO | WO 2003/082817 | 10/2003 |
| WO | WO 2003/084940 | 10/2003 |
| WO | WO 2003/095425 | 11/2003 |
| WO | WO 2003/099279 | 12/2003 |
| WO | WO 2003/099836 | 12/2003 |
| WO | WO 2003/101448 | 12/2003 |
| WO | WO 2003/101958 | 12/2003 |
| WO | WO 2003/104229 | 12/2003 |
| WO | WO 2003/106456 | 12/2003 |
| WO | WO 2004/000327 | 12/2003 |
| WO | WO 2004/004661 | 1/2004 |
| WO | WO 2004/007446 | 1/2004 |
| WO | WO 2004/007468 | 1/2004 |
| WO | WO 2004/009544 | 1/2004 |
| WO | WO 2004/014860 | 2/2004 |
| WO | WO 2004/018467 | 3/2004 |
| WO | WO 2004/018468 | 3/2004 |
| WO | WO 2004/018469 | 3/2004 |
| WO | WO 2004/020407 | 3/2004 |
| WO | WO 2004/032836 | 4/2004 |
| WO | WO 2004/033455 | 4/2004 |
| WO | WO 2004/037169 | 5/2004 |
| WO | WO 2004/037181 | 5/2004 |
| WO | WO 2004/041795 | 5/2004 |
| WO | WO 2004/041820 | 5/2004 |
| WO | WO 2004/043940 | 5/2004 |
| WO | WO 2004/046106 | 6/2004 |
| WO | WO 2004/048379 | 6/2004 |
| WO | WO 2004/050022 | 6/2004 |
| WO | WO 2004/050658 | 6/2004 |
| WO | WO 2004/052362 | 6/2004 |
| WO | WO 2004/052850 | 6/2004 |
| WO | WO 2004/058266 | 7/2004 |
| WO | WO 2004/064778 | 8/2004 |
| WO | WO 2004/067509 | 8/2004 |
| WO | WO 2004/069162 | 8/2004 |
| WO | WO 2004/071454 | 8/2004 |
| WO | WO 2004/076433 | 9/2004 |
| WO | WO 2004/076434 | 9/2004 |
| WO | WO 2004/085378 | 10/2004 |
| WO | WO 2004/085661 | 10/2004 |
| WO | WO 2004/087053 | 10/2004 |
| WO | WO 2004/087650 | 10/2004 |
| WO | WO 2004/092128 | 10/2004 |
| WO | WO 2004/096806 | 11/2004 |
| WO | WO 2004/099134 | 11/2004 |
| WO | WO 2004/103276 | 12/2004 |
| WO | WO 2004/103993 | 12/2004 |
| WO | WO 2004/104215 | 12/2004 |
| WO | WO 2004/104216 | 12/2004 |
| WO | WO 2004/108730 | 12/2004 |
| WO | WO 2004/110375 | 12/2004 |
| WO | WO 2004/110436 | 12/2004 |
| WO | WO 2004/111041 | 12/2004 |
| WO | WO 2004/111051 | 12/2004 |
| WO | WO 2004/112701 | 12/2004 |
| WO | WO 2005/000846 | 1/2005 |
| WO | WO 2005/000848 | 1/2005 |
| WO | WO 2005/003135 | 1/2005 |
| WO | WO 2005/009956 | 2/2005 |

(56) References Cited

FOREIGN PATENT DOCUMENTS

| | | |
|---|---|---|
| WO | WO 2005/011581 | 2/2005 |
| WO | WO 2005/012249 | 2/2005 |
| WO | WO 2005/012308 | 2/2005 |
| WO | WO 2005/012312 | 2/2005 |
| WO | WO 2005/019168 | 3/2005 |
| WO | WO 2005/020920 | 3/2005 |
| WO | WO 2005/023762 | 3/2005 |
| WO | WO 2005/025554 | 3/2005 |
| WO | WO 2005/026148 | 3/2005 |
| WO | WO 2005/030127 | 4/2005 |
| WO | WO 2005/030751 | 4/2005 |
| WO | WO 2005/032590 | 4/2005 |
| WO | WO 2005/033074 | 4/2005 |
| WO | WO 2005/033099 | 4/2005 |
| WO | WO 2005/034940 | 4/2005 |
| WO | WO 2005/037779 | 4/2005 |
| WO | WO 2005/037828 | 4/2005 |
| WO | WO 2005/040095 | 5/2005 |
| WO | WO 2005/042003 | 5/2005 |
| WO | WO 2005/042488 | 5/2005 |
| WO | WO 2005/044195 | 5/2005 |
| WO | WO 2005/047297 | 5/2005 |
| WO | WO 2005/049022 | 6/2005 |
| WO | WO 2005/058849 | 6/2005 |
| WO | WO 2005/063750 | 7/2005 |
| WO | WO 2005/072530 | 8/2005 |
| WO | WO 2005/075426 | 8/2005 |
| WO | WO 2005/079795 | 9/2005 |
| WO | WO 2005/082348 | 9/2005 |
| WO | WO 2005/082849 | 9/2005 |
| WO | WO 2005/086904 | 9/2005 |
| WO | WO 2005/087235 | 9/2005 |
| WO | WO 2005/092877 | 10/2005 |
| WO | WO 2005/116029 | 12/2005 |
| WO | WO 2006/034435 | 3/2006 |
| WO | WO 2006/034489 | 3/2006 |
| WO | WO 2006/044391 | 4/2006 |
| WO | WO 2006/064033 | 6/2006 |
| WO | WO 2006/117359 | 11/2006 |
| WO | WO 2006/117360 | 11/2006 |
| WO | WO 2007/025943 | 3/2007 |
| WO | WO 2007/028814 | 3/2007 |
| WO | WO 2007/031548 | 3/2007 |
| WO | WO 2007/053865 | 5/2007 |
| WO | WO 2007/054577 | 5/2007 |
| WO | WO 2007/072992 | 6/2007 |
| WO | WO 2007/093610 | 8/2007 |
| WO | WO 2007/128749 | 11/2007 |
| WO | WO 2008/011154 | 1/2008 |
| WO | WO 2008/049923 | 5/2008 |
| WO | WO 2008/055870 | 5/2008 |
| WO | WO 2008/055940 | 5/2008 |
| WO | WO 2009/015179 | 1/2009 |
| WO | WO 2009/097996 | 8/2009 |
| WO | WO 2000/056296 | 9/2009 |
| WO | WO 2009/111078 | 9/2009 |
| WO | WO 2009/151116 | 12/2009 |
| WO | WO 2010/040055 | 4/2010 |
| WO | WO 2012/040072 | 3/2012 |
| WO | WO 2012/040082 | 3/2012 |
| WO | WO 2012/071459 | 5/2012 |
| WO | WO 2013/071077 | 5/2013 |
| WO | WO 2014/120538 | 8/2014 |
| WO | WO 2015/005365 | 1/2015 |
| WO | WO 2015/095548 | 6/2015 |
| WO | WO 2016/054728 | 4/2016 |
| WO | WO 2016/144862 | 9/2016 |
| WO | WO 2016/164413 | 10/2016 |
| WO | WO 2017/139588 | 8/2017 |
| WO | WO 2017/211830 | 12/2017 |
| WO | WO 2018/035446 | 2/2018 |
| WO | WO 2018/053040 | 3/2018 |
| WO | WO 2018/131626 | 7/2018 |
| WO | WO 2018/187350 | 10/2018 |
| WO | WO 2018/193006 | 10/2018 |
| WO | WO 2020/142365 | 7/2020 |

OTHER PUBLICATIONS

Boxer et al., "Advances in progressive supranuclear palsy: new diagnostic criteria, biomarkers, and therapeutic approaches.", Lancet 16:552-563, 2017.

Boxer et al., "Davunetide in patients with progressive supranuclear palsy: a randomised, double-blind, placebo-controlled phase 2/3 trial", Lancet Neural. 132: 676-685, 2014.

Boxer et al., "Saccade abnormalities in autopsy-confirmed frontotemporal lobar degeneration and Alzheimer disease.", Arch. Neural., 69: 509-517, 2012.

Cho et al., "Subcortical 18 F-AV-1451 binding patterns in progressive supranuclear palsy.", Mav. Disard. 32: 134-140, 2017.

Clerici et al., "Rehabilitation in progressive supranuclear palsy: Effectiveness of two multidisciplinary treatments", PLoS One 12: e0170927, 2017.

Collino et al., "Modulation of the oxidative stress and inflammatory response by PPAR-gamma agonists in the hippocampus of rats exposed to cerebral ischemia/reperfusion.", Eur J Pharmacol., 530(1-2): 70-80, 2006.

Corona et al., "PPAR[gamma] as a therapeutic target to rescue mitochondrial function in neurological disease", Free Radical Biology and Medicine, vol. 100, pp. 153-163, 2016.

DePaoli et al., "Can a Selective PPARγ Modulator Improve Glycemic Control in Patients With Type 2 Diabetes With Fewer Side Effects Compared With Pioglitazone?", Diabetes Care, 37: 1918-1923, 2014.

Disanto et al., "Serum neurofilament light chain levels are increased in patients with a clinically isolated syndrome.", J Neural Neurosurg Psychiatry 87(2): 126-129, 2015.

Disanto et al., "Serum Neurofilament light: A biomarker of neuronal damage in multiple sclerosis.", Ann. Neural. 81(6): 857-870, 2017.

Eyer and Peterson, "Neurofilament-deficient axons and perikaryal aggregates in viable transgenic mice expressing a neurofilament-β-galactosidase fusion protein", Neuron 12: 389-405, 1994.

Fernandez-Botran et al., "Cytokine expression and microglial activation in progressive supranuclear palsy", Parkinsonism Relat Disord., 17(9): 683-8, 2011.

Ferrer et al., "Phosphorylated map kinase (ERK1, ERK2) expression is associated with early tan deposition in neurones and glial cells, but not with increased nuclear DNA vulnerability and cell death, in Alzheimer disease, Pick's disease, progressive supranuclear palsy and corticobasal degeneration.", Brain Pathol., 11(2): 144-58, 2001.

Gaiottino et al., "Increased Neurofilament Light Chain Blood Levels in Neurodegenerative Neurological Diseases", PLoS One, 8(9):e75091, 9 pages, 2013.

Gisslen et al., "Plasma Concentration of the Neurofilament Light Protein (NFL) is a Biomarker of CNS Injury in HIV Infection: A Cross-Sectional Study", EBioMedicine 3: 135-140, 2016.

Godoy et al., "INT131 increases dendritic arborization and protects against Aβ toxicity by inducing mitochondrial changes in hippocampal neurons", Biochemical and Biophysical Research Communications, vol. 490, No. 3, pp. 955-962, 2017.

Golbe et al., "A clinical rating scale for progressive supranuclear palsy", Brain 130(6): 1552-1565, 2007.

Higgins et al., "The Development of INT131 as a Selective PPARγ Modulator: Approach to a Safer Insulin Sensitizer", PPAR Research, vol. 2008, pp. 1-9, 2008.

Hinz et al., "Molecular Genetics of Neurodegenerative Dementias.", Cold Spring Harb. Perspect Biol., 9(4), 23 pages, 2017.

Hoglinger et al. "Identification of common variants influencing risk of the tauopathy Progressive Supranuclear Palsy", Nature Genet. 43:699-705, 2011.

Hughes et al., "The binaural masking level difference: cortical correlates persist despite severe brain stem atrophy in progressive supranuclear palsy.", J Neuraphysial. 112: 3086-3094, 2014.

(56) References Cited

OTHER PUBLICATIONS

International Preliminary Report on Patentability and Written Opinion in International Application No. PCT/US2018/025923, dated Oct. 8, 2019.
Josephs et al., "Voxel-based morphometry in autopsy proven PSP and CBD.", Neurabial. Aging 29: 280-289, 2008.
Josephs et al.., "The evolution of primary progressive apraxia of speech", Brain 137: 2783-2795, 2014.
Kapadia et al., "Mechanisms of anti-inflammatory and neuroprotective actions of PPAR-gamma agonists", Front Biosci., 13: 1813-26, 2008.
Koros et al., "Interventions in progressive supranuclear palsy", Parkinsonism & Related Disorders, vol. 22, Supplement 1, pp. S93-S95, 2016.
Kubota et al., "Adiponectin Stimulates AMP-Activated Protein Kinase in the Hypothalamus and Increases Food Intake", Cell Metab., 6: 55-68, 2007.
Kuhle et al., "A comparative study of CSF neurofilament light and heavy chain protein in MS.", Mult Seier 19: 1597-1603, 2013.
Kuhle et al., "Comparison of three analytical platforms for quantification of the neurofilament light chain in blood samples: ELISA, electrochemiluminescence immunoassay and Simoa.", Clin. Chem. Lab Med. 54(10): 1655-166, 2016.
Kuhle et al., "Serum neurofilament light chain in early relapsing remitting MS is increased and correlates with CSF levels and with MRI measures of disease severity.", Mult Scler.. 22(12): 1550-1559, 2016.
Lamb et al., "Progressive Supranuclear Palsy and Corticobasal Degeneration: Pathophysiology and Treatment Options.", Curr, Treat Options Neural. 14: 42, 18 pages, 2016.
Lee et al., "Selective PPARγ modulator INT131 normalizes insulin signaling defects and improves bone mass in diet-induced obese mice", Am J Physiol Endocrinol Metab., 302: 552-560, 2012.
Ling et al., "Clinical Approach to Progressive Supranuclear Palsy", J Mov. Discord. 9(1): 3-13, 2016.
Litvan et al., "Environmental and Occupational Risk Factors for Progressive Supranuclear Palsy: Case-Control Study", Movement Disord 31: 644-652, 2016.
Lycke et al., "Neurofilament protein in cerebrospinal fluid: a potential marker of activity in multiple sclerosis.", J Neural. Neurosurg. Psychiatry 64(3): 402-404, 1998.
Magdalinou et al., "A panel of nine cerebrospinal fluid biomarkers may identify patients with atypical parkinsonian syndromes.", J Neural. Neurosurg. Psychiatry 86: 1240-124 7, 2015.
Magdalinou et al., "Cerebrospinal fluid biomarkers in parkinsonian conditions: an update and future directions", J. Neural. Neurosurg. Psychiatry, 85(10): 1065-1075, 2014.
Marquie et al., "Validating novel tan positron emission tomography tracer [F-18]-AV-1451 (T807) on postmortem brain tissue.", Ann. Neural. 78: 787-800, 2015.
Min et al., "Critical Role of Acetylation in Tau-Mediated Neurodegeneration and Cognitive Deficits", Nat. Med. 21: 1154-1162, 2015.
Ng et al., "Potential Neuroprotective Effects of Adiponectin in Alzheimer's Disease", International Journal of Molecular Sciences, vol. 18, No. 3, 592, 13 pages, 2017.
Novakova et al., "Monitoring disease activity in multiple sclerosis using serum neurofilament light protein,", Neurology 89(22): 2230-2237, 2017.
Odetti et al., "Lipoperoxidation Is Selectively Involved in Progressive Supranuclear Palsy", J Neuropathol Exp Neural., 59(5): 393-397, 2000.
Ohara et al., "Neurofilament Deficiency in Quaff Caused by Nonsense Mutation in Neurofilament-L Gene", J. Cell Biol. 121: 387-395, 1993.
Rigby et al., "Smooth centile curves for skew and kurtotic data modelled using the Box-Cox power exponential distribution,", Med 23: 3053-3076, 2004.
Rissin et al., "Single-molecule enzyme-linked immunosorbent assay detects serum proteins at subfemtomolar concentrations.", Nat Biotechnol 28: 595-599, 2010.

Rohrer et al., "Serum neurofilament light chain protein is a measure of disease intensity in frontotemporal dementia.", Neurology 87(13): 1329-1336, 2016.
Rojas et al., "Plasma neurofilament light chain predicts progression in progressive supranuclear palsy.", Ann, Clin, Transl. Neural. 3:216-255, 2016.
Santiago et al., "A Network Approach to Diagnostic Biomarkers in Progressive Supranuclear Palsy", Mov. Discord 29(4): 550-555, 2014.
Santos-Santos et al., "Features of Patients With Nonfluent/Agrammatic Primary Progressive Aphasia With Underlying Progressive Supranuclear Palsy Pathology or Corticobasal Degeneration.", JAMA Neural. 73:733-742, 2016.
Sasaki et al., "Aggregate formation and phosphorylation of neurofilament-L Pro22 Charcot-Marie-Tooth disease mutants.", Hum. Mol . Genet. 15: 943-952, 2006.
Scherling et al., "CSF neurofilament concentration reflects disease severity in frontotemporal degeneration", Ann. Neural.75: 116-126, 2014.
Schneider et al., "Retinal single-layer analysis in Parkinsonian syndromes: an optical coherence tomography study.", J Neural Transm. 121: 41-47, 2014.
Smith et al., "Increased basal ganglia binding of 18 F-AV-1451 in patients with progressive supranuclear palsy.", Mav. Disard. 32: 108-114, 2017.
Teunissen et al., "Combination of CSF N-acetylaspartate and neurofilaments in multiple sclerosis.", Neurology 72(15): 1322-1329, 2009.
Teunissen et al., "Neurofilaments as biomarkers in multiple sclerosis.", Mult. Seier. 18(5): 552-556, 2012.
Walsh et al., "Rest-activity rhythm disruption in progressive supranuclear palsy.", Sleep Med 22; 50-56, 2016.
Whitwell et al., "[18 F]AV-1451 tau positron emission tomography in progressive supranuclear palsy.", Mov Disord. 32: 124-133, 2017.
Whitwell et al., "Midbrain atrophy is not a biomarker of progressive supranuclear palsy pathology.", Eur. J Neural. 20: 1417-1422, 2013.
Wilson et al., "The Simoa HD-1 Analyzer: A Novel Fully Automated Digital Immunoassay Analyzer with Single-Molecule Sensitivity and Multiplexing,", J Lab Autom 21(4): 533-547, 2015.
Yamauchi et al., "Adiponectin stimulates glucose utilization and fatty-acid oxidation by activating AMP-activated protein kinase", Nat Med., 8: 1288-1295, 2002.
Yamauchi et al., "Targeted disruption of AdipoR1 and AdipoR2 causes abrogation of adiponectin binding and metabolic actions", Nat Med., 13: 332-339, 2007.
Yanamandra et al., "Anti-tau antibody reduces insoluble tau and decreases brain atrophy.", Ann Clin Transl Neurol. 2: 278-288, 2015.
Yates et al., "Neurofilament subunit (NFL) head domain phosphorylation regulates axonal transport of neurofilaments.", Eur. J Cell Biol. 88: 193-202, 2009.
Zhu et al., "Delayed Maturation of Regenerating Myelinated Axons in Mice Lacking Neurofilaments", Exp. Neural. 148: 299-316, 1997.
Abd El-Haleim et al., "Effects of combined PPAR-γ and PPAR-α agonist therapy on fructose induced NASH in rats: Modulation of gene expression" European Journal of Pharmacology, Feb. 2016, 773:59-70.
Abdelmegeed et al., "CYP2E1 potentiates binge alcohol-induced gut leakiness, steatohepatitis, and apoptosis" Free Radical Biology and Medicine, Dec. 2013, 65:1238-1245.
Abdelmegeed et al., "PPARa Expression Protects Male Mice from High Fat-Induced Nonalcoholic Fatty Liver" The Journal of Nutrition, Apr. 2011, 141(4):603-610.
Abenavoli et al., "Obeticholic acid: a new era in the treatment of nonalcoholic fatty liver disease" Pharmaceuticals, 11(4):104, 10 pages, Dec. 2018.
Abu-Elheiga et al., "Mutant mice lacking acetyl-CoA carboxylase 1 are embryonically lethal" Proc. Nat. Acad Sci. USA, Aug. 2005 102:12011-12016.
Adams et al., "Hepascore: An Accurate Validated Predictor of Liver Fibrosis in Chronic Hepatitis C Infection" Clin Chem., Oct. 2005, 51(10):1867-1873.

(56) References Cited

OTHER PUBLICATIONS

Addy et al., "Hypoadiponectinemia Is Associated with Insulin Resistance, Hypertriglyceridemia, and Fat Redistribution in Human Immunodeficiency Virus-Infected Patients Treated with Highly Active Antiretroviral Therapy" J Clin Endocrinol Metab, Feb. 2003 88(2):627-636.
Afdal et al., "Is pulmonary vascular disease reversible with PPAR γ agonists?" Microcirculation, 25(3):e12444, 19 pages, Apr. 2018.
Agerso et al., "The pharmacokinetics, pharmacodynamics, safety and tolerability of NN2211, a new long-acting GLP-1 derivative, in healthy men" Diabetologia, Feb. 2002, 45(2):195-202.
Aki et al., "Role of adiponectin in chronic lymphocytic leukemia" Egyptian J Haematology, Oct. 2012, 37(4):187-192.
Ali et al., "Recent advances in the development of farnesoid X receptor agonists" Ann Transl Med., Jan. 2015, 3(1):5.
Al-Quaydheb et al., "Relation between vitamin B12 and Non-alcoholic fatty Liver Disease: A Hospital Based Study" International Journal of Advanced Research, 3:(6) 1335-1343, Jun. 2015.
Altekruse et al., "SEER Cancer Statistics Review, 1975-2007" National Cancer Institute, Table of Contents, 2009, 4 pages.
Anagnostis et al., "Comparative effects of rosuvastatin and atorvastatin on glucose metabolism and adipokine levels in non-diabetic patients with dyslipidaemia: a prospective randomised open-label study" Int J Clin Pract, Jun. 2011, 65(6):679-83.
Anastasilakis et al., "Circulating Irisin in Healthy, Young Individuals: Day-Night Rhythm, Effects of Food Intake and Exercise, and Associations With Gender, Physical Activity, Diet, and Body Composition" J Clin Endocrinol Metab, Sep. 2014, 99(9):3247-3255.
Angulo et al., "The NAFLD Fibrosis Score: A Noninvasive System That Identifies Liver Fibrosis in Patients with NAFLD" Hepatology, Apr. 2007, 45(4):846-54.
Anonymous: "Coherus Announces Positive Phase 2b Efficacy Data on Novel Oral Therapy in Relapsing Remitting Multiple Sclerosis | Coherus Biosciences, Inc." Jun. 28, 2016, Retrieved from the Internet: URL: https://investors.coherus.com/news-releases/news-releasedetails/, 3 pages.
Ansel et al., "Pharmaceutical Dosage Forms and Drug Delivery Systems" 6th Ed., Williams & Wilkins, Baltimore MD, 1995, 8 pages.
Antoniadisa et al., "Insulin resistance in relation to melanoma risk" Melanoma research. Dec. 2011, 21(6):541-546.
Anty et al., "Liver fibrogenesis and metabolic factors" Clinics and Research in Hepathology and Gastroenterology, 2011, 35: S10-S20.
Aoyama et al., "Pioglitazone Promotes Survival and Prevents Hepatic Regeneration Failure After Partial Hepatectomy in Obese and Diabetic KK-Ay Mice" Hepatology. May 2009, 49(5): 1636-44.
Aragonès et al., "PNPLA3 Expression Is Related to Liver Steatosis in Morbidly ObeseWomen with Non-Alcoholic Fatty Liver Disease" International Journal of Molecular Sciences, May 2016, 17(5):630, 13 pages.
Aref et al., "Impact of serum adiponectin and leptin levels in acute leukemia" Hematology, Jun. 2013 18(4):198-203.
Arioglu et al., "Efficacy and safety of troglitazone in the treatment of lipodystrophy syndromes" Annals of internal medicine, Aug. 2000, 133(4):263-74.
Aronis et al., "Circulating irisin levels and coronary heart disease: association with future acute coronary syndrome and major adverse cardiovascular events" International Journal of Obesity, Jan. 2015, 39(1):156-161.
Aronis et al., "Short-term walnut consumption increases circulating total adiponectin and apolipoprotein A concentrations, but does not affect makers of inflammation or vascular injury in obese humans with the metabolic syndrome: data from a double-blinded, randomized, placebo-controlled study" Metab. Clinical and Experimental, Nov. 2011, 61:577-582.
Arulmozhi et al., "GLP-1 based therapy for type 2 diabetes" European Journal of Pharmaceutical Sciences, May 2006, 28:96-108.

Assad et al., "Metabolic dysfunction in pulmonary arterial hypertension" Current hypertension reports, 17(3):20, 9 pages Mar. 1, 2015.
AU Office Action in Australian Appln. No. 2016229982, dated Jun. 24, 2019, 4 pages.
Augeri et al., "Discovery and preclinical profile of Saxagliptin (BMS-477118): a highly potent, long-acting, orally active dipeptidyl peptidase IV inhibitor for the treatment of type 2 diabetes" Journal of medicinal chemistry, Jul. 2005, 48(15):5025-37.
Augustyns et al., "Dipeptidyl peptidase IV inhibitors as new therapeutic agents for the treatment of Type 2 diabetes" Exp. Opin. Ther. Patents, Apr. 2003, 13:499-510.
Augustyns et al., "Inhibitors of proline-specific dipeptidyl peptidases: DPP IV inhibitors as a novel approach for the treatment of Type 2 diabetes" Expert Opinion On Therapeutic Patents, Oct. 2005, 15(10):1387-1407.
Avcu et al., "Association of plasma adiponectin concentrations with chronic lymphocytic leukemia and myeloproliferative diseases" International journal of hematology, Apr. 1, 2006, 83(3):254-258.
Avcu et al., "Plasma Adiponectin Concentrations in Relation to Chronic Lymphocytic Leukemia and Chronic Myeloproliferative Diseases" Blood, Nov. 2004, 104(11):4743.
Axtell et al., "T helper type 1 and 17 cell Determine Efficacy of IFN-B in Multiple Sclerosis and Experimental Encephalomyelitis" Nat Med., Apr. 2010, 16(4):406-412.
Ballabh et al., "The blood-brain barrier: an overview: structure, regulation, and clinical implications" Neurobiol Dis, Jun. 2004, 16(1):1-13.
Ban et al., "Structure-based design, synthesis, and nonalcoholic steatohepatits (NASH)-preventive effect of phenylpropanoic acid peroxisome proliferator-activated receptor (PPAR) beta-selective agonists" Bioorganic & Medicinal Chemistry, May 2011, 19(10):3183-3191.
Barb et al., "Adiponectin in relation to malignancies: a review of existing basic research and clinical evidence" Am J Clin Nutr., Sep. 2007, 86(3):858S-66S.
Barb et al., "Adiponectin signals in prostate cancer cells through Akt to activate the mammalian target of rapamycin pathway" Endocrine-Related Cancer, Dec. 2007, 14(4):995-1005.
Barb et al., "Adiponectin: a link between obesity and cancer" Expert Opinion on Investigational Drugs, Aug. 2006, 15(8):917-931.
Barber et al., "Structure and regulation of acetyl-CoA carboxylase genes of metazoa" Biochim et Biophys. Acta., Mar. 2005, 1733(1):1-28.
Baron et al., "PPAR activation differently affects microparticle content in atherosclerotic lesions and liver of a mouse model of atherosclerosis and NASH" Atherosclerosis, Sep. 2011, 218(1):69-76.
Bastianello et al., "Serial study of gadolinium-DTPA MRI enhancement in multiple sclerosis" Neurology, Apr. 1990, 40(4):591-595.
Bedogni et al., "The Fatty Liver Index: a simple and accurate predictor of hepatic steatosis in the general population" BioMed Central, BMC Gastroenterology, Dec. 2006, 6:33, 7 pages.
Behringer et al., "Pioglitazone alleviates cardiac and vascular remodelling and improves survival in monocrotaline induced pulmonary arterial hypertension" Naunyn-Schmiedeberg's archives of pharmacology, 389(4): 11 pages, Apr. 1, 2016.
Belalcazar et al., "Adiponectin and the mediation of HDL-cholesterol change with improved lifestyle: the Look AHEAD Study" Journal of Lipid Research, Dec. 2012, 53(12):2726-2733.
Belalcazar et al., "Improving Adiponectin Levels in Individuals With Diabetes and Obesity: Insights From Look AHEAD" Diabetes Care, Aug. 2015, 38(8):1544-1550.
Belfort et al. "A Placebo-Controlled Trial of Pioglitazone in Subjects with Nonalcoholic Steatohepatitis" The New England Journal of Medicine, Nov. 2006, 355(22):2297-2307.
Beraza et al., "Pharmacological IKK2 inhibition blocks liver steatosis and initiation of non-alcoholic steatohepatitis" Gut, May 2008 57(5):655-663.
Bifari et al., "Multiple target tissue effects of GLP-1 analogues on non-alcoholic fatty liver disease (NAFLD) and non-alcoholic steatohepatitis (NASH)" Pharmacological research, 137:219-229, Nov. 1, 2018.

(56) References Cited

OTHER PUBLICATIONS

Bluher et al., "Altered Levels of Adiponectin and Adiponectin Receptors May Underlie the Effect of Ciliary Neurotrophic Factor (CNTF) to Enhance Insulin Sensitivity in Diet-induced Obese Mice" Horm Metab Res., Mar. 2008, 40(3):225-227.
Bluher et al., "Circulating Adiponectin and Expression of Adiponectin Receptors in Human Skeletal Muscle: Associations with Metabolic Parameters and Insulin Resistance and Regulation by Physical Training" J. Clin. Endocrinol. Metab., Jun. 2006, 91(6):2310-2316.
Bluher et al., "Effects of a 1-Year Exercise and Lifestyle Intervention on Irisin, Adipokines, and Inflammatory Markers in Obese Children" Obesity, Jul. 2014, 22(7):1701-1708.
Bluher et al., "From leptin to other adipokines in health and disease: Facts and expectations at the beginning of the 21st century" Metabolism Clinical & Experimental, Jan. 2015, 64(1):131-145.
Bluher et al., "Gene Expression of Adiponectin Receptors in Human Visceral and Subcutaneous Adipose Tissue Is Related to Insulin Resistance and Metabolic Parameters and Is Altered in Response to Physical Training" Diabetes Care, Dec. 2007, 30(12):3110-3115.
Bluher et al., "Responsiveness to Peripherally Administered Melanocortins in Lean and Obese Mice" Diabetes, Jan. 2004, 53(1):82-90.
Bluher et al., "Total and High-Molecular Weight Adiponectin in Relation to Metabolic Variables at Baseline and in Response to an Exercise Treatment Program" Diabetes Care, Feb. 2007, 30(2):280-285.
Boland et al., "Towards a standard diet-induced and biopsy-confirmed mouse model of non-alcoholic steatohepatitis: Impact of dietary fat source" World journal of gastroenterology, 25(33):4904, Sep. 7, 2019.
BR Office Action in Brazilian Appln. No. BR112013007468-8, dated May 29, 2019, 9 pages.
Bradley et al. "Pulmonary arterial hypertension and insulin resistance" Journal of molecular and genetic medicine: an international journal of biomedical research, 2(Suppl 1), 18 pages, 2014.
Brault et al., "Statin treatment and new-onset diabetes: A review of proposed mechanisms" Metabolism Clinical & Experimental, 2014, 63:735-745.
Brennan et al., "Leptin and Adiponectin: Their Role in Diabetes" Current Diabetes Reports, Feb. 2007, 7:1-2.
Brennan et al., "Phobic Anxiety Is Associated With Higher Serum Concentrations of Adipokines and Cytokines in Women With Diabetes" Diabetes Care, May 2009, 32(5):926-931.
Brenner et al., "Decoding cell death signals in liver inflammation" Journal of Hepatology, Sep. 2013, 59(3):583-94.
Bright et al., "PPAR Regulation of Inflammatory Signaling in CNS Diseases" PPAR Research, 2008, vol. 2008, Article ID 658520, 12 pages.
Brittain et al., "Fatty acid metabolic defects and right ventricular lipotoxicity in human pulmonary arterial hypertension" Circulation, 133(20):1936-1944, May 17, 2016.
Brunt et al., "Nonalcoholic Fatty Livery Disease (NAFLD) Activity Score and the Histopathologic Diagnosis in NAFLD: Distinct Clinicopathologic Meanings" Hepatology, Mar. 2011, 53:810-820.
Brunt et al., "Nonalcoholic Steatohepatitis: A Proposal for Grading and Staging the Histological Lesions" Am J Gastroenterol., Sep. 1999, 94(9):2467-2474.
Budas et al., "Reduction of liver steatosis and fibrosis with an askl inhibitor in a murine model of nash is accompanied by improvements in cholesterol, bile acid and lipid metabolism" J Hepatol., Jan. 2016, 64(2):S170.
Buechler et al., "Adiponectin, a key adipokine in obesity related liver diseases" World J. of Gastroenterology, 2011, 17(23):2801-2811.
Buehring et al., "Glucocorticoid-induced osteoporosis: an update on effects and management" Journal of allergy and clinical immunology 32(5):1019-1030, Nov. 1, 2013.
Bullen et al., "Regulation of adiponectin and its receptors in response to development of diet-induced obesity in mice" Am J Physiol Endocrinol Metab, Apr. 2007, 292:E1079-E1086.

Calvier et al., "LRP1 deficiency in vascular SMC leads to pulmonary arterial hypertension that is reversed by PPARγ activation" Circulation research, 124(12):1778-1785, Jun. 7, 2019.
Calvier et al., "PPARγ links BMP2 and TGFβ pathways in vascular smooth muscle cells, regulating cell proliferation and glucose metabolism" Cell metabolism, 25(5):1118-1134, May 2, 2017.
Caprio et al., "Antiadipogenic Effects of the Mineralocorticoid Receptor Antagonist Drospirenone: Potential Implications for the Treatment of Metabolic Syndrome" Endocrinology, Jan. 2011, 152(1):113-25.
Carr et al., "FXR agonists as therapeutic agents for non-alcoholic fatty liver disease" Current atherosclerosis reports, 17(4):16, 14 pages, Apr. 1, 2015.
CAS No. 275371-94-3, 3 pages, 2019.
CAS No. 445479-97-0, 2 pages, 2019.
CAS Registry Record for INT-131 (Jan. 19, 2001), retrieved from STN on Apr. 13, 2020. (Year: 2001).
Cave et al., "Nuclear receptors and nonalcoholic fatty liver disease" Biocehmica et Biophysica Acta, Sep. 2016, 1859(9):1083-1099.
Chalasani et al., "The Diagnosis and Management of Nonalcoholic Fatty Liver Disease: Practice Guidance From the American Association for the Study of Liver Diseases" Hepatology, Jan. 2018, 67(1):328-357.
Chalasani et al., "The Diagnosis and Management of Non-Alcoholic Fatty Liver Disease: Practice Guideline by the American Association for the Study of Liver Diseases, American College of Gastroenterology, and the American Gastroenterological Association" Hepatology, Jun. 2012, 55(6):2005-2023.
Chalasani et al., "The Diagnosis and Management of Non-alcoholic Fatty Liver Disease: Practice Guideline by the American Gastroenterological Association, American Association for the Study of Liver Diseases, and American College of Gastroenterology" Gastroenterology, Jun. 2012, 142(7):1592-1609.
Chen et al., "Oestrogen inhibition reverses pulmonary arterial hypertension and associated metabolic defects" European Respiratory Journal, 50(2), 14 pages, Aug. 1, 2017.
Chen et al., "Treatment with geraniol ameliorates methionine choline-deficient diet-induced nonalcoholic steatohepatitis in rats" Journal of Gastroenterology and Hepatology, Jul. 2016, 31(7):1357-1365.
Cherny et al., "PBT2 Reduces Toxicity in a C. elegans Model of polyQ Aggregation and Extends Lifespan, Reduces Striatal Atrophy and Improves Motor Performance in the R6/2 Mouse Model of Huntington's Disease" Journal of Huntington's Disease, Jan. 2012, 1(2):211-219.
Chia et al., "Incretin-Based Therapies in Type 2 Diabetes Mellitus" The Journal of Clinical Endocrinology & Metabolism, Oct. 2008, 93(10):3703-16.
Chigurupati et al.,"A step ahead of PPARγ full agonists to PPARγ partial agonists: Therapeutic perspectives in the management of diabetic insulin resistance" European J. of Pharm., 755:50-57, 2015.
Chitturi et al., "Etiopathogenesis of nonalcoholic steatohepatitis" Seminars in Liver Disease, 2001, 21(1):27-41.
Choe et al., "Corrigendum to 'Variants of the adiponectin gene and diabetic microvascular complications in patients with type 2 diabetes'" Metab. Clin. Exp. Feb. 2017, 67:115.
Choe et al., "Variants of the adiponectin gene and diabetic microvascular complications in patients with type 2 diabetes" Metab. Clin. & Experimental, May 2013, 62:677-85.
Choi et al., "Anti-diabetic drugs inhibit obesity-linked phosphorylation of PPARγ by cdk5" Nature, Jul. 2010, 466:451-456.
Choi et al., "Serum adipocyte fatty acid-binding protein, retinol-binding protein 4, and adiponectin concentrations in relation to the development of the metabolic syndrome in Korean boys: a 3-y prospective cohort study" Am J Clin Nutr, Jan. 2011, 93:19-26.
Chou et al., "Adiponectin Receptor Expression in Human Malignant Tissues" Hormones and cancer. Jun. 2010, (3):136-45.
Clapp et al., "The mechanistic basis of prostacyclin and its stable analogues in pulmonary arterial hypertension: Role of membrane versus nuclear receptors" Prostaglandins & other lipid mediators, 120: 16 pages, Jul. 1, 2015.
Clarke et al., "Cross-Species Differential Plasma Protein Binding of MBX-102/JNJ39659100: A Novel PPAR-gamma Agonist" PPAR Res, 2008, 465715, 10 pages.

(56) References Cited

OTHER PUBLICATIONS

Claudel et al., "The Farnesoid X Receptor A Molecular Link Between Bile Acid and Lipid and Glucose Metabolism" Arterioscler Thromb Vase Biol., Oct. 2005, 25(10):2020-2031.

ClinicalTrials.gov [Online], "Archive NCT02638038" Dec. 20, 2015, retrieved on Dec. 20, 2015 from URL<https://clinicaltrials.gov/ct2/history/NCT02638038>, 4 pages.

Cohen et al., "Low LDL cholesterol in individuals of African descent resulting from frequent nonsense mutations in PCSK9" Nat. Genet., Feb. 2005, 37(2):161-65.

Cong et al., "The establishment of a novel non-alcoholic steatohepatitis model accompanied with obesity and insulin resistance in mice" Life Sciences, May 2008, 82(19-20):983-990.

Correale et al., "The blood-brain barrier in multiple sclerosis: functional roles and therapeutic targeting." Autoimmunity, Jan. 2007,40(2):148-160.

Cox, "Rationally designed PPARδ-specific agonists and their therapeutic potential for metabolic syndrome" PNAS, Mar. 2017, 114(13):3284-3285.

Crowell et al., "Metabolic pathways link childhood adversity to elevated blood pressure in midlife adults" Obesity Research & Clinical Practice, Sep. 2016, 10:580-588.

Cusi et al., "Long-term pioglitazone treatment for patients with nonalcoholic steatohepatitis and prediabetes or type 2 diabetes mellitus: a randomized trial" Annals of internal medicine. Sep. 2016, 165(5):305-15.

Cutter et al., "Development of a multiple sclerosis functional composite as a clinical trial outcome measure" Brain, May 1999, 122(5):871-882.

Dal Maso et al., "Relationship between a wide range of alcohol consumptions, components of the insulin-like growth factor system and adiponectin" European Journal of Clinical Nutrition, Feb. 2007, 61(2):221-225.

Dalamaga et al., "Adiponectin and resistin are associated with risk for myelodysplastic syndrome, independently from insulin-like growth factor-I (IGF-I) system" Eur. J. of Cancer, Aug. 2008, 44(12):1744-1753.

Dalamaga et al., "B-cell chronic lymphocytic leukemia risk in association with serum leptin and adiponectin: a case-control study in Greece" Cancer Causes Control, Sep. 2010, 21(9):1451-1459.

Dalamaga et al., "Circulating Adiponectin and Leptin in Relation to Myelodysplastic Syndrome: A Case-Control Study" Oncology, 2007, 73(1-2):26-32.

Dalamaga et al., "Higher fetuin-A, lower adiponectin and free leptin levels mediate effects of excess body weight on insulin resistance for myelodysplastic syndrome" Metab. Clin. & Exp., Dec. 2013, 62(12):1830-1839.

Dalamaga et al., "Low circulating adiponectin and resistin, but not leptin, levels are associated with multiple myeloma risk: a case-control study" Cancer Causes Control, Mar. 2009, 20(2):193-199.

Dalamaga et al., "Pancreatic cancer expresses adiponectin receptors and is associated with hypoleptinemia and hyperadiponectinemia: a case-control study" Cancer Causes Control, Jul. 2009, 20(5):625-633.

Dalamaga et al., "Serum adiponectin and leptin in relation to risk for preeclampsia: results from a large case-control study" Metab. Clin. And Exp., Nov. 2011, 60(11):1539-1544.

Dalamaga et al., "The Role of Adiponectin in Cancer: A Review of Current Evidence" Endocrine Reviews, Aug. 2012, 33(4):547-594.

Danese et al., "Analytical evaluation of three enzymatic assays for measuring total bile acids in plasma using a fully-automated clinical chemistry platform" PLoS One, Jun. 2017, 12(6):e0179200, 13 pages.

Danne et al., "Combined SGLT1 and SGLT2 inhibitors and their role in diabetes care" Diabetes technology & therapeutics, 20(S2): 10 pages, Jun. 1, 2018.

De Ledinghen et al., "Controlled attenuation parameter for the diagnosis of steatosis in non-alcoholic fatty liver disease" J Gastroenterol Hepatol., Apr. 2016, 31(4):848-55.

Deacon et al., "Dipeptidyl Peptidase IV Inhibition Potentiates the Insulinotropic Effect of Glucagon-Like Peptide 1 in the Anesthetized Pig" Diabetes, May 1998, 47(5):764-769.

Deacon et al., "Inhibitors of dipeptidyl peptidase IV: a novel approach for the prevention and treatment of Type 2 diabetes?" Exp. Opin. Investig. Drugs, Sep. 2004, 13(9):1091-1102.

Delahanty et al., "Genetic Predictors of Weight Loss and Weight Regain After Intensive Lifestyle Modification,Metformin Treatment, or Standard Care in the Diabetes Prevention Program" Diabetes Care, Feb. 2012, 35(2):363-366.

Delyani, "Mineralocorticoid receptor antagonists: The evolution of utility and pharmacology" Kidney Int., Apr. 2000, 57(4):1408-11.

Depaoli et al., "INT131 Besylate, a Selective PPAR[gamma] Modulator (SPPARM), Improved Glyce~ic Control in Patients with Type 2 Diabetes without Causing the Edema Seen with Pioglitazone" Abstract, American Diabetes Association, 2 pages Jun. 1, 2010.

Depo-Provera, Trademark Reg. No. 2,680,672, 1 page Year: 2003.

Di Lascio et al., "Steato-Score: Non-Invasive Quantitative Assessment of Liver Fat by Ultrasound Imaging" Ultrasound Med Biol., Aug. 2018, 44(8):1585-1596.

Diehl et al., "Treatment with selonsertib, an inhibitor of apoptosis signal-regulating kinase 1, hepatic phospho-p38 expression and markers of hepatocellular apoptosis and necrosis in patients with nonalcoholic steatohepatitis" Journal of Hepatology, 66(1), S51-S52, 2017.

DiMasi et al., "The price of innovation: new estimates of drag development costs" J Health Econ., Mar. 2003, 22(2):151-185.

Ding et al., "Exendin-4, a glucagon-like protein-1 (GLP-1) receptor agonist, reverses hepatic steatosis in ob/ob mice" Hepatoiogy, Jan. 2006, 43(1):173-81.

Domenici et al., "Peroxisome proliferator-activated receptors alpha and gamma2 polymorphisms in nonalcoholic fatty liver disease: A study in Brazilian patients" Gene, Oct. 2013, 529(2):326-331.

Dongiovanni et al., "Peroxisome Proliferator-Activated Receptor Genetic Polymorphisms and Nonalcoholic Fatty Liver Disease: Any Role in Disease Susceptibility?" Oct. 2013, vol. 2013, Article ID 452061, 9 pages.

Donthamsetty et al., "Nonalcoholic steatohepatitc (NASH) mice are protected from higher hepatotoxicity of acetaminophen upon induction of PPARa with clofibrate" Toxicology and Applied Pharmacology, Aug. 2008, 230(3):327-337.

Doyle et al., "Biophysical signatures of noncovalent aggregates formed by a glucagonlike peptide-1 analog: A prototypical example of biopharmaceutical aggregation" J. Pharm Sci., Dec. 2005, 94(12):2749-2763.

Drew et al., "PPAR-y: Therapeutic Potential for Multiple Sclerosis" PPAR Research, vol. 2008, Article ID 627463, Hindawi Publishing Corporation, doi: 10.1155/2008/627463, 9 pages, 2008.

Drucker, "Enhancing incretin action for the treatment of type 2 diabetes." Diabetes Care, Oct. 2003, 26(10):2929-2940.

Dufour, "NASH and thiazolidinediones: Not to be taken lightly" Journal of Hepatology, Oct. 2007, 47(4):451-453.

Dunn et al., "Peroxisome proliferator-activated receptor (PPAR) alpha expression in T cells mediates gender differences in development of T cell-mediated autoimmunity" The Journal of experimental medicine, Feb. 2007, 204(2):321-330.

Dunn et al., "Peroxisome proliferator-activated receptor delta limits the expansion of pathogenic Th cells during central nervous system autoimmunity" Journal of Experimental Medicine, Aug. 2010, 207(8):1599-608.

Dunn et al., "Selective modulation of PPAR-gamma activity can lower plasma glucose without typical thiazolidinedione side-effects in patients with Type 2 diabetes" J Diabetes Complications, May 2011, 25(3):151-158.

Dunn et al., "The Gender Gap in Multiple Sclerosis" JAMA neurology, May 2013, 70(5):634-5.

Duparc et al., "Hepatocyte MyD88 affects bile acids, gut microbiota and metabolome contributing to regulate glucose and lipid metabolism" Gut., Apr. 2017, 66:620-632.

Dyson et al., "Non-alcoholic fatty liver disease: a practical approach to treatment" Frontline Gastroenterol., Jul. 2014, 5:277-86.

(56) References Cited

OTHER PUBLICATIONS

Elbrond et al., "Pharmacokinetics, pharmacodynamics, safety, and tolerability of a single-dose of NN2211, a long-acting glucagon-like peptide 1 derivative, in healthy male subjects." Diabetes Care., Aug. 2002, 25(8):1398-1404.
EP Extended European Search Report in Appln. No. 16762290, dated Oct. 4, 2018, 8 pages.
EP Extended European Search Report in Appln. No. 17842205, dated Mar. 12, 2020, 12 pages.
EP Extended European Search Report in Appln. No. 17851479, dated May 4, 2020, 7 pages.
EP Office Action in European Appln. No. 11827285.5, dated Jul. 5, 2018, 15 pages.
EP Office Action in European Appln. No. 14746632, dated Apr. 3, 2019, 4 pages.
Epstein et al., "Drug evaluation: PSN-9301, a short-acting inhibitor of dipeptidyl peptidase IV." Curr Opin Investig Drugs, Apr. 2007, 8(4):331-337.
Eshraghian et al., "Non-alcoholic fatty liver disease and thyroid dysfunction: A systematic review" World J Gastroenterol., Jul. 2014, 20(25):8102-8109.
Extended European Search Report in Appln. No. 18741523.7, dated Jul. 16, 2020, 8 pages.
Fargnoli et al., "Adherence to healthy eating patterns is associated with higher circulating total and high-molecular-weight adiponectin and lower resistin concentrations in women from the Nurses' Health Study" Am J Clin Nutr., Nov. 2008, 88(5):1213-1224.
Fargnoli et al., "Resistin is associated with biomarkers of inflammation while total and high-molecular weight adiponectin are associated with biomarkers of inflammation, insulin resistance, and endothelial function" European Journal of Endocrinology, Feb. 2010, 162(2):281-288.
Farrell et al., "Nonalcoholic Fatty Liver Disease: From Steatosis to Cirrhosis" Hepatology, Feb. 2006, 43(S1):S99-112.
Fasting et al., "Maternal Levels of Corticotropin-Releasing Hormone during Pregnancy in Relation to Adiponectin and Leptin in Early Childhood" J Clin Endocrinol Metab, Apr. 2009, 94(4):1409-1415.
Feghali et al., "Cytokines in acute and chronic inflammation" Front Biosci (Landmark Ed), Jan. 1997, 2(1):d12-26.
Feinstein et al., "Peroxisome proliferator-activated receptor-γ agonists prevent experimental autoimmune encephalomyelitis" Ann. Neurol., Jun. 2002, 51(6):694-702.
Feldstein et al., "Cytokeratin-18 fragment levels as noninvasive biomarkers for nonalcoholic steatohepatitis: a multicenter validation study" Hepatology, Oct. 2009, 50(4):1072-2078.
Festuccia et al., "Peroxisome proliferator-activated receptor-gamma-mediated positive energy balance in the rat is associated with reduced sympathetic drive to adipose tissues and thyroid status" Endocrinology, May 2008, 149(5):2121-2130.
Fialova et al., "Serum and cerebrospinal fluid light neurofilaments and antibodies against them in clinically isolated syndrome and multiple sclerosis" Journal of Neuroimmunology, Sep. 2013, 262(1):113-120.
Fiorenza et al., "Lipodystrophy: pathophysiology and advances in treatment" Nat. Rev. Endocrinol., Mar. 2011, 7(3):137-150.
Fiorucci et al., "Cross-talk between farnesoid-X-receptor (FXR) and peroxisome proliferator-activated receptor γ contributes to the antifibrotic activity of FXR ligands in rodent models of liver cirrhosis" Journal of Pharmacology and Experimental Therapeutics, 315(1): 12 pages, Oct. 1, 2005.
Fisher et al., "Drug metabolizing enzyme induction pathways in experimental non-alcoholic steatohepatitis" Arch Toxicol., Dec. 2008, 82(12):959-964.
Ford et al., "Prevalence of the Metabolic Syndrome Among US Adults Findings From the Third National Health and Nutrition Examination Survey" JAMA, Jan. 2002, 287(3):356-359.
Fowler, "Diabetes Treatment, Part 3: Insulin and Incretins" Clinical Diabetes, Jan. 2008, 26(1):35-39.
Fowler et at, "Host-derived adiponectin is tumor-suppressive and a novel therapeutic target for multiple myeloma and the associated bone disease" Blood, 118(22), 5872-5882, 2011.
Francque et al., "PPARa gene expression correlates with severity and histological treatment response in patients with non-alcoholic steatohepatitis" Journal of Hepatology, Jul. 2015, 63(1):164-173.
Friedrich et al., "Response of fibroblast growth factor 19 and bile acid synthesis after a body weight-adjusted oral fat tolerance test in overweight and obese NAFLD patients: a non-randomized controlled pilot trial" BAM Gastroenterol., Dec. 2018, 18(1):76-85.
Fujita et al., "Dysfunctional Very-Low-Density Lipoprotein Synthesis and Release Is a Key Factor in Nonalcoholic Steatohepatitis Pathogenesis" Hepatology, Sep. 2009, 50(3):772-780.
Fujita et al., "Telmisartan, An Angiotensin II Type 1 Receptor Blocker, Controls Progress of Nonalcoholic Steatohepatitis in Rats" Digestive diseases and sciences, Dec. 2007, 52(12):3455-3464.
Gaemers et al., "Lipotoxicity and steatohepatitis in an overfed mouse model for non-alcoholic fatty liver disease" Biochemica et Biophysica Acta, Apr. 2011, 1812(4):447-458.
Gale et al., "Energy Homeostasis, Obesity and Eating Disorders: Recent Advances in Endocrinology" J. Nutr. Feb. 2004, 134(2):295-298.
Garattini et al., "New approaches to cancer therapy." Ann. Oneal., 2003, 14:813-816.
Garcia-Ruiz et al., "NADPH oxidase is implicated in the pathogenesis of oxidative phosphorylation dysfunction in mice fed a high-fat diet" Scientific Reports, May 2016, 6(1):23664, 13 pages.
Gasbarrino et al., "Circulating Chemerin Is Associated With Carotid Plaque Instability, Whereas Resistin Is Related to Cerebrovascular Symptomatology" Arterioscler Thromb Vasc Biol., Aug. 2016, 36(8):1670-1678.
Gastaldelli et al., "Pioglitazone in the treatment of NASH: the role of adiponectin" Aliment Pharmacol Ther, Sep. 2010, 32(6):769-775.
Gatta et al., "Survival of European children and young adults with cancer diagnosed 1995-2002" Eur. J Cancer, Apr. 2009, 45(6):992-1005.
Gavrila et al., "Diurnal and Ultradian Dynamics of Serum Adiponectin in Healthy Men: Comparison with Leptin, Circulating Soluble Leptin Receptor, and Cortisol Patterns" J Clin Endocrinol Metab, Jun. 2003, 88:2838-2843.
Gavrila et al., "Serum Adiponectin Levels Are Inversely Associated with Overall and Central Fat Distribution but Are Not Directly Regulated by Acute Fasting or Leptin Administration in Humans: Cross-Sectional and Interventional Studies" J Clin Endocrinol Metab, Oct. 2003, 88(10):4823-4831.
George et al., "Nonalcoholic Fatty Liver Disease: Pathogenesis and Potential for Nuclear Receptors as Therapeutic Targets" Molecular pharmaceutics, Feb. 2008, 4;5(1):49-59.
Georgescu et al., "Angiotensin-receptor blockers as therapy for mildto-moderate hypertension-associated non-alcoholic steatohepatitis" World J Gastroenterol, Feb. 2009, 15(8):942-954.
Gialamas et al., "Serum adiponectin levels and tissue expression of adiponectin receptors are associated with risk, stage, and grade of colorectal cancer" Metabolism Clinical and Experimental, Nov. 2011, 60(11):1530-1538.
Gillman et al., "Breast-feeding, Adipokines, and Childhood Obesity" Epidemiology, Nov. 2007, 18(6):730-732.
Girnun et al., "Synergy between PPARgamma ligands and platinum-based drugs in cancer" Cancer Cell, May 2007, 11(5):395-406.
Glaesner et al., "Engineering and characterization of the long-acting glucagon-like peptide-1 analogue LY2189265, an Fc fusion protein" Diabetes/metabolism research and reviews, 26(4):287-296, May 2010.
Gold et al., "Understanding pathogenesis and therapy of multiple sclerosis via animal models: 70 years of merits and culprits in experimental autoimmune encephalomyelitis research" Brain, Aug. 2006, 129(8):1953-1971.
Gong et al., "Hypoxia induces downregulation of PPAR-γ in isolated pulmonary arterial smooth muscle cells and in rat lung via transforming growth factor-β signaling" American Journal of Physiology-Lung Cellular and Molecular Physiology, 301(6):L899-907, Dec. 2011.

(56) References Cited

OTHER PUBLICATIONS

Gouni-Berthold et al., "Short-term treatment with ezetimibe, simvastatin or their combination does not alter circulating adiponectin, resistin or leptin levels in healthy men" Clinical Endocrinology, Apr. 2008, 68(4):536-541.
Graham et al., "Antisense inhibition of proprotein convertase subtilisin/kexin type 9 reduces serum LDL in hyperlipidemic mice" J. Lipid Res., Apr. 2007, 48(4):763-67.
Grommes et al., "The PPARγ agonist pioglitazone crosses the blood-brain barrier and reduces tumor growth in a human xenograft model" Cancer Chemother Pharmacol., Apr. 2013, 71(4):929-936.
Gupte et al., "Rosiglitazone Attenuates Age- and Diet-Associated Nonalcoholic Steatohepatitis in Male Low-Density Lipoprotein Receptor Knockout Mice" Hepatology, Dec. 2010, 52(6):2001-11.
Hameed et al., "Emerging therapies for nonalcoholic fatty liver disease" Clin Liver Dis., 2016, 20:365-385.
Hansmann et al., "PPARγ activation: a potential treatment for pulmonary hypertension" Science translational medicine, 1(12):12ps14, 15 pages Dec. 23, 2009.
Haznedaroglu, "Monitoring the response to tyrosine kinase inhibitor (TKI) treatment in chronic myeloid leukemia (CML)" Mediterranean journal of hematology and infectious diseases, 6(1), e 2014009, 8 pages, 2014.
Heidemann et al., "Total and High-Molecular-Weight Adiponectin and Resistin in Relation to the Risk for Type 2 Diabetes in Women" Sep. 2008, 149(5):307-316.
Higgins et al., "Selective peroxisome proliferator-activated receptor gamma (PPAR-gamma) modulation as a strategy for safer therapeutic PPAR-gamma activation" Am J Clin Nutr, Jan. 2010, 91(1):267S-272S.
Hinds et al., "Does bilirubin prevent hepatic steatosis through activation of the PPARα nuclear receptor?" Med. Hypth., Aug. 2016, 96:54-7.
Hivert et al., "Circulating IL-18 and the risk of type 2 diabetes in women" Diabetologia, Oct. 2009, 52(10):2101-2108.
Hivert et al., "Higher Adiponectin Levels Predict Greater Weight Gain in Healthy Women in the Nurses' Health Study" Obesity, Feb. 2011, 19(2):409-415.
Ho et al., "Obelicholic acid, a synthetic bile acid agonist of the farnesoid X receptor, attenuates experimental autoimmune encephalomyelitis" PNAS, Feb. 2016, 113(6):1600-1605.
Hofmann et al., "Low levels of circulating adiponectin are associated with multiple myeloma risk in overweight and obese individuals" Cancer research, Apr. 2016, 1:76(7):1935-41.
Holst, "Treatment of Type 2 diabetes mellitus with agonists of the GLP-1 receptor or DPP-IV inhibitors" Exp. Opin. Emerg. Drugs, May 2004, 9(1):155-166.
Holz et al., "Glucagon-Like Peptide-1 Synthetic Analogs: New Therapeutic Agents for Use in the Treatment of Diabetes Mellitus" Chepumy, OG. Curr Med Chem., Nov. 2003, 10(22):2471-2483.
Honda et al., "The selective SGLT2 inhibitor ipragliflozin has a therapeutic effect on nonalcoholic steatohepatitis in mice" PLoS One, 11(1):e0146337, 13 pages, Jan. 5, 2016.
Horton et al., "Molecular biology of PCSK9: its role in LDL metabolism" Trends Biochem. Sci., Feb. 2007, 32(2):71-77.
Hossain et al., "The prevention and treatment of hypoadiponectinemia-associated human diseases by up-regulation of plasma adiponectin" Life Sciences, Aug. 2015, 135:55-67.
Hsu et al., "A Carboxyl-terminal Extension of the Zinc Finger Domain Contributes to the Specificity and Polarity of Peroxisome Proliferator-activated Receptor DNA Binding" J Biol. Chem., Oct. 1998, 273(43):27988-27997.
Hsu et al., "Monascin and ankaflavin act as natural AMPK activators with PPARα agonist activity to down-regulate nonalcoholic steatohepatitis in high-fat diet-fed C57BL/6 mice" Food Chem. Toxic., Nov. 2013, 64:94-103.
Huayu et al., "The correlation between peroxisome proliferator-activated receptor γ and liver diseases" International Journal of Epidemiology and Infectious Disease, 40(1): 62-65, English Abstract, Feb. 2013.
Huffman et al., "Abdominal Obesity, Independent from Caloric Intake, Accounts for the Development of Intestinal Tumors in Apc1638N/+ Female Mice" Cancer Prev Res, Mar. 2013, 6(3):177-187.
Huh et al., "FNDC5 and irisin in humans: I. Predictors of circulating concentrations in serum and plasma and II. mRNA expression and circulating concentrations in response to weight loss and exercise" Metabolism, Dec. 2012, 61(12):1725-38.
IL Office Action in Appln. No. 248954, dated Jan. 6, 2018, 3 pages.
Inamura et al., "Prediagnosis Plasma Adiponectin in Relation to Colorectal Cancer Risk According to KRAS Mutation Status" JNCI J Natl Cancer Inst, Apr. 2016, 108(4):djv363, 10 pages.
Inoue et al., "Bach1 gene ablation reduces steatohepatitis in mouse MCD diet model" J. Clin. Biochem. Nutr., Feb. 2011, 48(2):161-166.
International Preliminary Report on Patentability in International Appln. No. PCT/US2019/068688, dated Oct. 14, 2021, 9 pages.
International Preliminary Report on Patentability in International Appln. No. PCT/US2019/025118, dated Oct. 15, 2020, 11 pages.
International Preliminary Report on Patentability in International Appln. No. PCT/US2019/068693, dated Oct. 14, 2021, 10 pages.
International Preliminary Report on Patentability in International Appln. No. PCT/US2019/068698, dated Oct. 14, 2021, 12 pages.
International Preliminary Report on Patentability in International Appln. No. PCT/US2019/068704, dated Oct. 14, 2021, 13 pages.
International Preliminary Report on Patentability in International Appln. No. PCT/US2019/068706, dated Oct. 14, 2021, 11 pages.
International Preliminary Report on Patentability in International Appln. No. PCT/US2019/068710, dated Jul. 15, 2021, 12 pages.
International Search Report and Written Opinion in international Appln. No. PCT/US2020/055567, dated Jan. 22, 2021, 16 pages.
International Search Report and Written Opinion in International Appln. No. PCT/US2009/059384, dated May 25, 2010, 13 pages.
International Search Report and Written Opinion in International Appln. No. PCT/US2010/044495, dated Apr. 29, 2011, 11 pages.
International Search Report and Written Opinion in International Appln. No. PCT/US2011/052100, dated May 1, 2012, 13 pages.
International Search Report and Written Opinion in International Appln. No. PCT/US2014/12656, dated May 13, 2014, 5 pages.
International Search Report and Written Opinion in International Appln. No. PCT/US2016/021162, dated May 23, 2016, 10 pages.
International Search Report and Written Opinion in International Appln. No. PCT/US2017/47578, dated Nov. 17, 2017, 9 pages.
International Search Report and Written Opinion in International Appln. No. PCT/US2018/025923, dated Jul. 24, 2018, 18 pages.
International Search Report and Written Opinion in International Appln. No. PCT/US2018/14240, dated Mar. 19, 2018, 18 pages.
International Search Report and Written Opinion in International Appln. No. PCT/US2019/025118, dated May 6, 2019, 18 pages.
International Search Report and Written Opinion in International Appln. No. PCT/US2019/068688, dated Apr. 20, 2020, 17 pages.
International Search Report and Written Opinion in International Appln. No. PCT/US2020/034480, dated Aug. 18, 2020, 15 pages.
International Search Report and Written Opinion in International Appln. No. PCT/US2019/068693, dated Apr. 20, 2020, 19 pages.
International Search Report and Written Opinion in International Appln. No. PCT/US2019/068698, dated Jul. 3, 2020, 21 pages.
International Search Report and Written Opinion in International Appln. No. PCT/US2019/068704, dated Jun. 25, 2020, 22 pages.
International Search Report and Written Opinion in International Appln. No. PCT/US2019/068706, dated Jun. 25, 2020, 21 pages.
International Search Report and Written Opinion in International Appln. No. PCT/US2019/068710, dated Jun. 25, 2020, 22 pages.
Ishak et al., "Histological grading and staging of chronic hepatitis" J Hepatol., 1995, 22:696-699.
Jeftic et al., "Galectin-3 Ablation Enhances Liver Steatosis, but Attenuates Inflammation and IL-33-Dependent Fibrosis in Obesogenic Mouse Model of Nonalcoholic Steatohepatitis" Mol Med., Jan. 2015, 21(1):453-465.
Jeon et al., "Genistein alleviates the development of nonalcoholic steatohepatitis in ApoE−/− mice fed a high-fat diet" Mol. Nutr. Food Res., Apr. 2014, 58(4):830-841.

(56) References Cited

OTHER PUBLICATIONS

Jha et al., "Role of Adipose Triglyceride Lipase (PNPLA2) in Protection From Hepatic Inflammation in Mouse Models of Steatohepatitis and Endotoxemia" Hepatology. Mar. 2014, 59(3):858-69.
Jiang et al., "PPAR-gamma agonists inhibit production of monocyte inflammatory cytokines." Nature, Jan. 1998, 391(6662):82-86.
Jin et al., "Neuroprotective effects of PPAR-γ agonist rosiglitazone in N171-82Q mouse model of Huntington's disease" Journal of neurochemistry, May 2013, 125(3):410-419.
Jojima et al., "Empagliflozin (an SGLT2 inhibitor), alone or in combination with linagliptin (a DPP-4 inhibitor), prevents steatohepatitis in a novel mouse model of non-alcoholic steatohepatitis and diabetes" Diabetology & metabolic syndrome, Dec. 2016;8(1):1-11, Dec. 2016.
Joshi-Barve et al., "Alcoholic, Nonalcoholic, and Toxicant-Associated Steatohepatitis: Mechanistic Similarities and Differences" Cell Mol Gastroenterol Hepatol., Jul. 2015, 1(4):356-367.
Joung et al., "Early Life Adversity Is Associated With Elevated Levels of Circulating Leptin, Irisin, and Decreased Levels of Adiponectin in Midlife Adults" J Clin Endocrinol Metab, Jun. 2014, 99(6):E1055-E1060.
JP Office Action in Appln. No. 2017-566609, dated Dec. 24, 2019, English Translation, 8 pages.
Jung et al., "Sitagliptin attenuates methionine/choline-deficient diet-induced steatohepatitis" Diabetes research and clinical practice, 105(1): 12 pages, Jul. 1, 2014.
Kaiser et al., "A pilot test of pioglitazone as an add-on in patients with relapsing remitting multiple sclerosis" Journal of Neuroimmunology, Jun. 2009, 211(1-2):124-130.
Kakazu et al., "The influence of pioglitazone on the plasma amino acid profile in patients with nonalcoholic steatohepatitis (NASH)" Hepatol Int., Jun. 2013, 7(2):577-585.
Kaklamani et al., "Adiponectin pathway polymorphisms and risk of breast cancer in African Americans and Hispanics in the Women's Health Initiative" Breast Cancer Res. Trea., Apr. 2013, 139:461-8.
Kaklamani et al., "Polymorphisms of ADIPOQ and ADIPORI and prostate cancer risk" Metabolism, Sep. 2011, 60(9):1234-43.
Kaklamani et al., "Variants of the Adiponectin (ADIPOQ) and Adiponectin Receptor 1 (ADIPORI) Genes and Colorectal Cancer Risk" JAMA,, Oct. 2008, 300(13):1523-1531.
Kaklamani et al., "Variants of the Adiponectin and Adiponectin Receptor 1 Genes and Breast Cancer Risk" Cancer Res., May 2008, 68(9):3178-84.
Kallwitz et al., "Role of peroxisome proliferators-activated receptors in the pathogenesis and treatment of nonalcoholic fatty liver disease" Worl J. Gastroenterol., Jan. 2008, 14(1):22-8.
Kalra et al., "Glucagon-like peptide-1 receptor agonists in the treatment of type 2 diabetes: past, present, and future" Indian journal of endocrinology and metabolism, 20(2): 14 pages, Mar. 2016.
Kanakasabai et al., "Peroxisome proliferator-activated receptor delta agonists inhibit T helper type 1 (Th1) and Th17 responses in experimental allergic encephalomyelitis" Immunology, Aug. 2010, 130:572-588.
Kang and Chen, "Curcumin eliminates oxidized LDL roles in activating hepatic stellate cells by suppressing gene expression of lectin-like oxidized LDL receptor-1" Lab. Invest., Nov. 2009, 89:1275-90.
Kang et al., "Variants of the Adiponectin and Adiponectin Receptor-1 Genes and Posttransplantation Diabetes Mellitus in Renal Allograft Recipients" J. Clin. Endocrinol. Metab., Jan. 2012, 97(1):E129-35.
Karachialiou et al., "Real-time liquid biopsies become a reality in cancer treatment" Ann. Transl. Med, Mar. 2015, 3(3):36, 3 pages.
Karagozian et al., "Obesity-associated mechamsms of hepatocarcinogenesis" Metabolism, May 2014, 63(5):507-617.
Karakosta et al., "Cord blood leptin levels in relation to child growth trajectories" Metabolism, Mar. 2016, 65:874-82.
Karas et al., "Relations of Plasma Total and High-Molecular-Weight Adiponectin to New-Onset Heart Failure in Adults ≥65 Years of Age (from the Cardiovascular Health Study)" Am. J. Cardiol., Jan. 2014, 113:328-34.
Karla et al., "Glucagon-like peptide-I receptor agonists in the treatment of type 2 diabetes: Past, present, and future" Indian J Endocrinol Metab., 2016, 20(2):254-267.
Kato et al., "Therapeutic effects of angiotensin II type 1 receptor blocker, irbesartan, on non-alcoholic steatohepatitis using FLS-ob/ob male mice" Internatl. J. Mole. Med., Feb. 2012, 30:107-13.
Katsiki et al., "Non-alcoholic fatty liver disease and dyslipidemia: An update" Metabolism, May 2016, 65:1109-23.
Katsiki, "Statins in relation to adiponectin: A significant association with clinical implications" Atherosclerosis, Aug. 2016, 253:270-2.
Kawaguchi et al., "Pioglitazone prevents hepatic steatosis, fibrosis, and enzyme-altered lesions in rat liver cirrhosis induced by a choline-deficient L-amino acid-defined diet" Biochem. Biophys. Res. Comm., 2004, 315:187-95.
Kawahara et al., "Peroxisome Proliferator-Activated Receptor γ (PPARγ)-Independent Specific Cytotoxicity against Immature Adipocytes Induced by PPARγ Antagonist T0070907" Biol. Pharm. Bull., Jun. 2013, 36(9):1428-34.
Kelesidis et al., "Adiponectin and cancer: a systematic review" Br. J. Cancer, Mar. 2006, 94:1221-5.
Kersey et al., "T0903131, a selective modulator of PPAR-gamma activity, increases adiponectin levels in healthy subjects" Diabetes, Jun. 1, 2004.
Khalil et al., "Neurofilaments as biomarkers in neurological disorders" Nature Reviews Neurology, 14(10):577-589, Oct. 2018.
Khan et al., "Biomarker Detection of Neurological Disorders through Spectroscopy Analysis" International Dental & Medical Journal of Advanced Research, 2018, 4(1):1-9.
Khandekar et al., "Noncanonical agonist PPARγ ligands modulate the response to DNA damage and sensitize cancer cells to cytotoxic chemotherapy" Proceedings of the National Academy of Sciences, Jan. 2018, 115(3):561-6.
Kharitonenkov et al., "FGF-21 as a novel metabolic regulator" J Clin. Invest., Jun. 2005, 115:1627-1635.
Kim et al., "Development and characterization of a glucagon-like peptide 1-albumin conjugate: the ability to activate the glucagon-like peptide 1 receptor in vivo" Diabetes, Mar. 2003, 52(3):751-759.
Kim et al., "Intratracheal exposure to multi-walled carbon nanotubes induces a nonalcoholic steatohepatitislike phenotype in C57BL/6J mice" Nanotoxicology, Sep. 2014, 9(5):613-23.
Kim et al., "Lifestyle modification increases circulating adiponectin concentrations but does not change vaspin concentrations" Metabolism, Jan. 2011, 60:1294-9.
Kim et al., "Rosiglitazone attenuates hypoxia-induced pulmonary arterial hypertension in rats" Respirology, 15(4):659-668, May 2010.
Kizer et al., "Associations of Total and High-Molecular-Weight Adiponectin With All-Cause and Cardiovascular Mortality in Older Persons" Circulation, Dec. 2012, 126(25):2951-61.
Kizer et al., "Total and High-Molecular-Weight Adiponectin and Risk of Coronary Heart Disease and Ischemic Stroke in Older Adults" J. Clin. Endocrinol. Metab., Jan. 2013, 98(1):255-63.
Kizer et al., "Total and High-Molecular-Weight Adiponectin and Risk of Incident Diabetes in Older People" Diabetes Care, Feb. 2012, 35:415-23.
Kleiner et al., "Design and Validation of a Histological Scoring System for Nonalcoholic Fatty Liver Disease" Hepatology, Jun. 2005, 41(6):1313-1321.
Klotz et al., "The nuclear receptor PPARgamma selectively inhibits Th17 differentiation in a T cell-intrinsic fashion and suppresses CNS autoimmunity" Journal of Experimental Medicine, Sep. 2009, 206(10):2079-89.
Komeda, "Obesity and NASH in Japan" Hept. Res., Oct. 2005, 33:83-6.
Körner et al., "Total and High-Molecular-Weight Adiponectin in Breast Cancer: In Vitro and in Vivo Studies" J. Clin. Endocrinol, Metab., Mar. 2007,92(3):1041-8.

(56) References Cited

OTHER PUBLICATIONS

Kourouma et al., "Effects of 4-nonylphenol on oxidant/antioxidant balance systeminducing hepatic steatosis in male rat" Toxicol. Rep., Oct. 2015, 2:1423-33.
Kristiansen et al., "Obese diet-induced mouse models of nonalcoholic steatohepatitis-tracking disease by liver biopsy" World J Hepatol., Jan. 2016, 8(16):673-684.
Kuchay et al., "Effect of empagliflozin on liver fat in patients with type 2 diabetes and nonalcoholic fatty liver disease: a randomized controlled trial (E-LIFT Trial)" Diabetes care, 41(8):1801-1808, Aug. 1, 2018.
Kuhle et al., "Fingolimod and CSF neurofilament light chain levels in relapsing-remitting multiple sclerosis" Neurology, Apr. 21, 2015, 84(16):1639-1643.
Kummer et al., "PPARs in Alzheimer's disease" PPAR Research, ID 403896, 2008, 1-8 pages.
Kuwashiro et al., "Telmisartan improves nonalcoholic steatohepatitis in medaka (Oryzias latipes) by reducing macrophage infiltration and fat accumulation" Cell Tissue Res., Feb. 2011, 344:125-34.
Kyung-Kim et al., "PAR-1622 is a selective peroxisome proliferator-activated receptor gamma partial activator with preserved antidiabetic efficacy and broader safety profile for fluid retention" Arch Pharm Res, May 2009, 32(5):721-727.
Lake et al., "Transcription factor binding site enrichment analysis predicts drivers of altered gene expression in nonalcoholic steatohepatitis" Biochem. Pharmacol., Nov. 2016, 122:62-71.
Lalloyer et al., "Peroxisome Proliferator-Activated Receptor-Gene Level Differently Affects Lipid Metabolism and Inflammation in Apolipoprotein E2 Knock-In Mice" Arterioscler. Thromb. Vasc. Biol., Mar. 2011, 31:1573-9.
Larter et al., "Peroxisome proliferator-activated receptor-a agonist, Wy 14 643, improves metabolic indices, steatosis and ballooning in diabetic mice with non-alcoholic steatohepatitis" J. Gastroenterol. Hepatol., Feb. 2012, 27(2):341-50.
Lavine, "Vitamin E treatment of nonalcoholic steatohepatitis in children: A pilot study 2000" The Journal of pediatrics, Jun. 2000, 1; 136(6):734-8.
Lebovitz et al., "Rosiglitazone Clinical Trials Study Group. Rosiglitazone monotherapy is effective in patients with type 2 diabetes" The Journal of Clinical Endocrinology & Metabolism, 86(1):280-288, Jan. 1, 2001.
Leclercq, "Pathogenesis of steatohepatitis : insights from the study of animal models" Acta Gastroenterol. Belg., Jan.-Mar. 2007, 70(1):25-31.
Lee et al., "Effects of leptin and adiponectin on pancreatic β-cell function" Metabolism, Apr. 2011, 60:1664-72.
Legchenko et al., "PPARγ agonist pioglitazone reverses pulmonary hypertension and prevents right heart failure via fatty acid oxidation" Science translational medicine, 10(438): 18 pages, Apr. 25, 2018.
Lehmann et al., "An antidiabetic thiazolidinedione is a high affinity ligand for peroxisome proliferator-activated receptor gamma (PPAR gamma)" J. Biol. Chem, Jun. 1995, 270(22):12953-12956.
Lemoine et al., "Altered hepatic expression of SREBP-1 and PPARg is associated with liver injury in insulin-resistant lipodystrophic HIV-infected patients" AIDS, Sep. 2011, 20:387-95.
Lemoine et al., "Hepatic molecular effects of rosiglitazone in human non-alcoholic steatohepatitis suggest long-term pro-inflammatory damage" Heptal. Res., 2014, 44:1241-7.
Lemoine et al., "PPAR and Liver Injury in HIV-Infected Patients" PPAR Res., Jan. 2009, 2009:906167.
Leroux et al., "Toxic lipids stored by Kupffer cells correlates with their pro-inflammatory phenotype at an early stage of steatohepatitis" J. Hept., Jul. 2012, 57:141-9.
Li et al., "Effects of endoxins on the expression of peroxisome proliferator-activated receptor alpha in the development of nonalcoholic steatohpatitis in rats" Chin. J. Hepatol., Feb. 2006, 13(2):89-91.
Li et al., "The effects of PPAR-gamma ligand pioglitazone on platelet aggregation and arterial thrombus formation" Cardiovascular Research Mar. 2005. 65(4):907-912.
Liang et al., "Salsalate attenuates diet induced non-alcoholic steatohepatitis in mice by decreasing lipogenic and inflammatory processes" Br. J. Pharmacol., Aug. 2015, 172:5293-305.
Libbey et al., "Experimental autoimmune encephalomyelitis as a testing paradigm for adjuvants and vaccines" Apr. 2011, 29(17):3356-3362.
Lichtinghagen et al., "The Enhanced Liver Fibrosis (ELF) score: normal values, influence factors and proposed cut-off values." J Hepatol., Aug. 2013, 59(2):236-242.
Ligibel et al., "Impact of a mixed strength and endurance exercise intervention on levels of adiponectin, high molecular weight adiponectin and leptin in breast cancer survivors" Cancer Causes Control, May 2009, 20:1523-8.
Lin et al., "Lipid and inflammatory biomarkers and kidney function decline in type 2 diabetes" Diabetologia, Nov. 2009, 53:263-7.
Liss and Finck, "PPARs and nonalcoholic fatty liver disease" Biochimie, Dec. 2016, 136:65-74.
Liu et al., "Adiponectin administration prevents weight gain and glycemic profile changes in diet-induced obese immune deficient Rag1–/– mice lacking mature lymphocytes" Metabolism, Sep. 2016, 65:1720-30.
Liu et al., "Antioxidant Mechanisms in Nonalcoholic Fatly Liver Disease" Curr. Drug Tar., Nov. 2015, 16(12):1301-1314.
Liu et al., "Lack of mature lymphocytes results in obese but metabolically healthy mice when fed a high-fat diet" International Journal of Obesity, Oct. 2015, 39(10):1548-1557.
Liu et al., "The ameliorating effect of rosiglitazone on experimental nonalcoholic steatohepatitis is associated with regulating adiponectin receptor expression in rats" Euro. J. Pharmacol., Oct. 2010, 650:384-9.
Liu et al., "The role of fibroblast growth factor 21 in the pathogenesis of non-alcoholic fatty liver disease and implications for therapy" Metabolism, Mar. 2015, 64(3):380-90.
Liu et al., "Vitamin b6 prevents endothelial dysfunction, insulin resistance, and hepatic lipid accumulation in apoe–/– mice fed with high-fat diet" Journal of diabetes research, 2016, 8 pages Oct. 2016.
Lo et al., "Adipsin Is an Adipokine that Improves β Cell Function in Diabetes" Cell, Jul. 2014, 158(1):41-53.
Lomonaco et al., "Nonalcoholic Fatty Liver Disease: Current Issues and Novel Treatment Approaches" Drugs, Jan. 2013, 73(1):1-14.
Loyer et al., "Liver microRNA-21 is overexpressed in non-alcoholic steatohepatitis and contributes to the disease in experimental models by inhibiting PPARα expression" Gut, Sep. 2015, 65:1882-94.
Lubkowska et al, "Adiponectin as a Biomarker of Osteoporosis in Postmenopausal Women: Controversies" Hindawi Publishing Corporation, Disease Markers, Oct. 2014, vol. 2014, Article ID 975178, 1 page.
Lutchman et al., "The Effects of Discontinuing Pioglitazone in Patients with Nonalcoholic Steatohepatitis" Hepatology, Aug. 2007, 46(2):424-9.
Lv et al., "Noninvasive Quantitative Detection Methods of Liver Fat Content in Nonalcoholic Fatty Liver Disease." J. Clin Transl Hepatol., Jun. 2018, 6(2):217-221.
Ma et al., "Hepatoprotective effects of geniposide in a rat model of nonalcoholic steatohepatitis" J. Pharm. Pharmacol., Jan. 2011, 63:587-93.
Machado et al., "Vitamin B5 and N-acetylcysteine in nonalcoholic steatohepatitis: a preclinical study in a dietary mouse model" Digestive diseases and sciences, 61(1):12 pages, Jan. 1, 2016.
Madar et al., "Discovery of 2-[4-{{2-(2S,5R)-2-Cyano-5-ethynyl-1-pyrrolidinyl]-2-oxoethyl]amino]-4-methyl-1-piperidinyl]-4-pyridinecarboxylic Acid (ABT-279): A Very Potent, Selective, Effective, and Well-Tolerated Inhibitor of Dipeptidyl Peptidase-IV, Useful for the Treatment of Diabetes" J. Med. Chem, Oct. 2006, 49(21):6416-6420.
Maechiba et al., "Disposition of the new antidiabetic agent pioglitazone in rats, dogs, and monkeys" Arzneimittel-forschung, Jan. 1997, 47(1):29-35.
Magkos and Mantzoros, "Body fat redistribution and metabolic abnormalities in HIV-infected patients on highly active antiretroviral

(56) References Cited

OTHER PUBLICATIONS therapy: novel insights into pathophysiology and emerging opportunities for treatment" Metabolism, 2011, 60:749-53.
Magkos et al., "Leptin replacement improves postprandial glycemia and insulin sensitivity in human immunodeficiency virus-infected lipoatrophic men treated with pioglitazone: a pilot study" Metabolism, Oct. 2010, 60:1045-9.
Maglich et al., "The nuclear receptor CAR (NR1I3) regulates serum triglyceride levels under conditions of metabolic stress" J. Lipid Res., Oct. 2008, 50:439-45.
Mamalakis et al., "Depression and serum adiponectin and adipose omega-3 and omega-6 fatty acids in adolescents" Pharmacology, Biochemistry and Behavior, Oct. 2006, 85(2):474-479.
Mantzoros et al., "Adherence to the Mediterranean dietary pattern is positively associated with plasma adiponectin concentrations in diabetic women1-3" Am. J. Clin. Nutr., Aug. 2006, 84:328-35.
Mantzoros et al., "Adiponectin and Breast Cancer Risk" J. Clin. Endocrinol. Metab., Mar. 2004, 89(3):1102-7.
Mantzoros et al., "Circulating Adiponectin Levels Are Associated with Better Glycemic Control, More Favorable Lipid Profile, and Reduced Inflammation in Women with Type 2 Diabetes" J. Clin. Endcorinol. Metab., Aug. 2005, 90(8):4542-8.
Mantzoros et al., "Cord Blood Leptin and Adiponectin as Predictors of Adiposity in Children at 3 Years of Age: A Prospective Cohort Study" Pediatrics, Feb. 2009, 123:682-9.
Mantzoros et al., "Maternal diet and cord blood leptin and adiponectin concentrations at birth" Clinical Nutrition, Oct. 2010, 29(5):622-626.
Mantzoros et al., "Serum adiponectin concentrations in relation to maternal and perinatal characteristics in newborns" Eur. J. Endocrinol., Dec. 2004, 151:741-6.
Marangoni et al., "A candidate gene study reveals association between a variant of the Peroxisome Proliferator-Activated Receptor Gamma (PPAR-γ) gene and systemic sclerosis" Arthritis research & therapy, 17(1):Dec. 1-8, 2015.
Marino et al., "Glucocorticoid Receptor Induces Hepatic Steatosis by Augmenting Inflammation and Inhibition of the Peroxisome Proliferator-activated Receptor (PPAR)" The Journal of Biological Chemistry, Dec. 2016, 291(50):25776-88.
Martinez et al., "A mechanistic approach to understanding the factors affecting drug absorption: A review of fundamentals" J Clin Pharmacol, Jun. 2002, 42(6):620-643.
Mas et al., "IL-6 Deficiency Attenuates Murine Diet-Induced Non-Alcoholic Steatohepatitis" PLoS One, Nov. 2009, 4(11):e7929.
Maso et al., "Circulating Adiponectin and Endometrial Cancer Risk" J Clin Endocrinol Metab, 2004, 89(3):1160-1163.
Matarese et al., "Leptin and Adipocytokines: Bridging the Gap Between Immunity and Atherosclerosis" Current Pharmaceutical Design, Dec. 2007, 13(36):3676-3680.
Matsunami et al., "Regulation of synthesis and oxidation of fatty acids by adiponectin receptors (AdipoR1/R2) and insulin receptor substrate isoforms (IRS-1/-2) of the liver in a nonalcoholic steatohepatitis animal model" Metabolism Clinical and Experimental, Jun. 2011, 60(6):805-814.
Mazza et al., "The role of metformin in the management of NAFLD" Experimental diabetes research, 2012: 14 pages, Dec. 12, 2011.
McPherson et al., "Simple non-invasive fibrosis scoring systems can reliably exclude advanced fibrosis in patients with non-alcoholic fatty liver disease" Gut., Sep. 2010, 59(9):1265-1269.
Melistas et al., "Association of the C45TOG and C276GOT polymorphisms in the adiponectin gene with insulin resistance in nondiabetic Greek women" Eur. J. Endocrinol., 2009, 161:845-52.
Mencarelli et al., "VSL#3 Resets Insulin Signaling and Protects against NASH and Atherosclerosis in a Model of Genetic Dyslipidemia and Intestinal Inflammation" PLoS One, Sep. 2012, 7(9):e45425.
Mergulhao et al., "Recombinant protein secretion in *Escherichia coli*" Biotechnol. Advances, May 2005, 23(3):177-202.

Michalakis et al., "In prostate cancer, low adiponectin levels are not associated with insulin resistance" Eur. J. Clin. Invest. Jun. 2015, 45:572-8.
Michalakis et al., "Serum Adiponectin Concentrations and Tissue Expression of Adiponectin Receptors Are Reduced in Patients with Prostate Cancer: A Case Control Study" Cancer Epidemiol., Biomarkers Prev., Feb. 2007, 16(2):308-13.
Miller et al., "A Controlled Trial of Natalizumab for Relapsing Multiple Sclerosis" New England Journal of Medicine, Jan. 2003, 348(1):15-23.
Miller et al., "Efficacy of six months' therapy with oral rosiglitazone maleate in relapsing-remitting multiple sclerosis" 10th Annual Meeting of the Americas Committee for Treatment and Research in Multiple Sclerosis 2005, 1 page.
Minagar et al., "Blood-brain barrier disruption in multiple sclerosis" Multi Seier, Dec. 2003, 9(6):540-549.
Mintziori et al., "Emerging and future therapies for nonalcoholic steatohepatitis in adults" Expert Opinion on Pharmacotherapy, Sep. 2016, 17(14):1937-1946.
Mishra et al., "Current Treatment Strategies for Non-Alcoholic Fatty Liver Disease (NAFLD)" Current Drug Discovery Technologies, Aug. 2007, 4(2):133-140.
Mitsiades et al., "Circulating Adiponectin Is Inversely Associated with Risk of Thyroid Cancer: In Vivo and in Vitro Studies" J Clin Endocrinol Metab, Dec. 2011, 96(12):E2023-E2028.
Miyamura et al., "Drug-induced Nonalcoholic Steatohepatitis" Yakugaku Zasshi: Journal of the Pharmaceutical Society of Japan, Jan. 2016, 1;136(4):579-82.
Mokhtar et al., "Combination therapy in combating cancer." Oncotarget, Jun. 2017, 6;8(23):38022-38043.
Molica et al., "Does adiponectin act as an antiangiogenic factor in B-ceH chronic lympbocytic leukemia?", Adv Hematol., Jan. 2009:287974, 6 pages.
Monzillo et al., "Effect of Lifestyle Modification on Adipokine Levels in Obese Subjects with Insulin Resistance" Resistance. Obes Res., Sep. 2003, 11(9):1048-1054.
Moon et al., "Adiponectin and metformin additively attenuate IL1b-induced malignant potential of colon cancer" Endocrine-Related Cancer, Dec. 2013, 20(6):849-859.
Moon et al., "Amylin-induced downregulation of hippocampal neurogenesis is attenuated by leptin in a STAT3/AMPK/ERK-dependent manner in mice" Diabetologia, Mar. 2013, 56(3):627-634.
Moon et al., "Direct Role of Adiponectin and Adiponectin Receptors in Endometrial Cancer: In Vitro and Ex Vivo Studies in Humans" Mol Cancer Ther, Dec. 2011, 10(12):2234-2243.
Moon et al., "Salutary effects of adiponectin on colon cancer: in vivo and in vitro studies in mice" Gut., Apr. 2013, 62(4):561-570.
Motani et al., "A selective modulator of PPARy" J Mal. Biol., Mar. 2009, 386(5):1301-1311.
Mukundan et al., "PPAR-delta senses and orchestrates clearance of apoptotic cells to promote tolerance" Nat Med., Nov. 2009, 15(11):1266-1272.
Murphy et al., "Effects of thiazolidinediones on bone loss and fracture" Annals of Pharmacotherapy, Dec. 2007, 41(12):2014-2018.
Musso et al., "Impact of current treatments on liver disease, glucose metabolism and cardiovascular risk in non-alcoholic fatty liver disease (NAFLD): a systematic review and meta-analysis of randomised trials" Diabetologia, Apr. 2012, 55(4):885-904.
Musso et al., "New Pharmacologic Agents That Target Inflammation and Fibrosis in Nonalcoholic Steatohepatitis-Related Kidney Disease" Clinical Gastroenterology and Hepatology, Jul. 2017, 15(7):972-985.
MX Office Action in Mexican Appln. No. MX/a/2013/003160, dated Apr. 13, 2018, 4 pages.
Nagasawa et al., "Effects of bezafibrate, PPAR pan-agonist, and GW501516, PPARδ agonist, on development of steatohepatitis in mice fed a methionine- and choline-deficient diet" European Journal of Phannacology, Apr. 2006, 536(1-2):182-191.
Nagaya et al., "Mechanism of the development of nonalcoholic steatohepatitis after pancreaticoduodenectomy" BBA Clinical Jun. 2015. 3:168-174.

(56) References Cited

OTHER PUBLICATIONS

Nakagami et al., "Nifedipine prevents hepatic fibrosis in a non-alcoholic steatohepatitis model induced by an L-methionine-and choline-deficient diet" Molecular medicine reports, Jan. 2012, 5(1):37-40.

Nakagami et al., "Prevention and regression of non-alcoholic steatohepatitis (NASH) in a rat model by metabosartan, telmisartan" International journal of molecular medicine, Oct. 2010, 26(4):477-81.

Nakajima et al., "The roles of PPARs in digestive diseases" Apr. 2005, 63(4):665-671.

Nakayama et al., "Effects of adiponectin transgenic expression in liver of nonalcoholic steatohepatitis model mice" Metabolism Clinical and Experimental, Jul. 2009, 58(7):901-8.

Nan et al., "Rosiglitazone prevents nutritional fibrosis and steatohepatitis in mice" Scandinavian Journal of Gastroenterology, Jan. 2009, 44:358-365.

Natarajan et al., "Peroxisome proliferator-activated receptor-gamma agonists inhibit experimental allergic encephalomyelitis by blocking IL-12 production, IL-12 signaling and Th1 differentiation" Genes & Immunity, Apr. 2002, 3(2):59-70.

Nauck et al., "Gastric Inhibitory Polypeptide and Glucagon-Like Peptide-1 in the Pathogenesis of Type 2 Diabetes" Diabetes, Dec. 2004, 53(Suppl. 3):S 190-196.

Naumann et al., "A simple synthesis of dihydroxybipyridyls" Synthesis 1990, 4:279-281.

Neuman et al., "Biomarkers in Nonalcoholic Fatty Liver Disease" Can J Gastroenterol Hepatol., Dec. 2014, 28(11):607-618.

Neuschwander-Tetri et al., "Farnesoid X nuclear receptor ligand obeticholic acid for non-cirrhotic, non-alcoholic steatohepatitis (FLINT): a multicentre, randomised, placebo-controlled trial" Lancet, Mar. 2015, 385(9972):956-965.

Neuschwander-Tetri et al., "Improved Nonalcoholic Steatohepatitis After 48 Weeks of Treatment With the PPAR-γ Ligand Rosiglitazone" Hepatology, Oct. 2003, 38(4):1008-17.

Neuschwander-Tetri et al., "Interim results of a pilot study demonstrating the early effects of the PPAR-g ligand rosiglitazone on insulin sensitivity, aminotransferases, hepatic steatosis and body weight in patients with non-alcoholic steatohepatitis" Journal of Hepatology, Apr. 2003, 38(4):434-440.

Nordhoff et al., "The reversed binding of β-phenethylamine inhibitors of DPP-IV: X-ray structures and properties of novel fragment and elaborated inhibitors" Bioorganic Medical Chemistry Leiters, Mar. 2006, 16(6):1744-1748.

Nowak et al., "Differentiation therapy of leukemia: 3 decades of development" Blood, 113(16), 3655-3665.

Nozaki et al., "Deficiency of iNOS-derived NO accelerates lipid accumulation-independent liver fibrosis in nonalcoholic steatohepatitis mouse model" BMC Gastroenterology, Dec. 2015, 15(1):42.

Ogasawara et al., "A novel and comprehensive mouse model of human non-alcoholic steatohepatitis with the full range of dysmetabolic and histological abnormalities induced by gold thioglucose and a high-fat diet" Liver International, Apr. 2011, 31(4):542-51.

Oliveira et al., "Vitamin C and vitamin E in prevention of nonalcoholic fatty liver disease (NAFLD) in choline deficient diet fed rats" Nutrition journal, 2(1):1-5, Dec. 2003.

Ono et al., "Bofutsushosan, a Japanese herbal (Kampo) medicine, attenuates progression of nonalcoholic steatohepatitis in mice" Journal of Gastroenterology, Jun. 2014, 49(6):1065-73.

Oshima et al., "Adiponectin increases bone mass by suspecting osteoclast and activating osteoblast" Biochem. And Bophys. Res. Comm., 331:520-526, 2005.

Ota et al., "Insulin Resistance Accelerates a Dietary Rat Model of Nonalcohol Steatohepatitis" Gastroenterology, Jan. 2007, 132(1):282-93.

Park et al., "Adiponectin as an Anti-fibrotic and Anti-inflammatory Adipokine in the Liver" Curr Pathobiol Rep., Dec. 2015, 3(4):243-252.

Park et al., "Circulating Irisin in Relation to Insulin Resistance and the Metabolic Syndrome" J Clin Endocrinol Metab, Dec. 2013, 98(12):4899-907.

Park, "Current status of liver disease in Korea: Nonalcoholic fatty liver disease" Korean J. Hepatol., 2009, 15(Suppl 6):S34-S39.

Paruthi et al., "Adipokines in the HIV/HAART-associated lipodystrophy syndrome" Metabolism Clinic and Experimental, Sep. 2013, 62(9):1199-1205.

Pavo et al., "Effect of pioglitazone compared with metformin on glycemic control and indicators of insulin sensitivity in recently diagnosed patients with type 2 diabetes" The Journal of Clinical Endocrinology & Metabolism, 88(4):1637-1645, Apr. 1, 2003.

Pawella et al., "Perilipin discerns chronic from acute hepatocellular steatosis" Journal of Hepatology, Mar. 2014, 60(3):633-642.

Pawlak et al., "Molecular mechanism of PPARa action and its impact on lipid metabolism, inflammation and fibrosis in non-alcoholic fatty liver disease" Journal of Hepatology, Mar. 2015, 62(3):720-733.

Pawlak et al., "The Transrepressive Activity of Peroxisome Proliferator-Activated Receptor Alpha Is Necessary and Sufficient to Prevent Liver Fibrosis in Mice" Hepatology, Nov. 2014, 60(5):1593-606.

Pazaitou-Panayiotou et al., "Serum Adiponectin And Insulin-Like Growth Factor 1 In Predominantly Female Patients With Thyroid Cancer: Association With The Histologic Characteristics Of The Tumor"EndocrPract., Jan. 2016. 22(1):68-75.

Pederson et al., "Improved Glucose Tolerance in Zucker Fatty Rats by Oral Administration of the Dipeptidyl Peptidase IV Inhibitor Isoleucine Thiazolidide" Diabetes, Aug. 1998, 47(8):1253-1258.

Pei et al., "Discovery of ((4R,5S)-5-amino-4-(2,4,5-trifluorophenyl)cyclohex-1-enyl)-(3-(trifluoromethyl)-5,6-dihydro-[1,2,4]triazolo[4,3-a]pyrazin-7(8H)-yl)methanone (ABT-341), a highly potent, selective, orally efficacious, and safe dipeptidyl peptidase IV inhibitor for the treatment of type 2 diabetes" J. Med. Chem., Nov. 2006, 49(22):6439-6442.

Perez et al., "Bile-acid-induced cell injury and protection," World J Gastroenterol., Apr. 2009, 15(14):1677-1689.

Perng et al., "A prospective study of maternal prenatal weight and offspring cardiometabolic health in midchildhood" Annals of Epidemiology Nov. 2014, 24(11):793-800.

Perrotta et al., "Pulmonary hypertension and obesity: focus on adiponectin" International journal of molecular sciences, 20(4):912, 13 pages, Jan. 2019.

Pershadsingh et al., "Effect of pioglitazone treatment in a patient with secondary multiple sclerosis" Journal of Neuroinflammation, Dec. 2004, 1:3, 4 pages.

Perumpail et al., "Clinical epidemiology and disease burden of nonalcoholic fatty liver disease." World J Gastroenterology, Dec. 2017, 23(47):8263-8438.

Petridou et al., "Adiponectin in relation to childhood myeloblastic leukaemia" British Journal of Cancer, Jan. 2006, 94(1):156-160.

Petridou et al., "Circulating Adiponectin Levels and Expression of Adiponectin Receptors in Relation to Lung Cancer: Two Case-Control Studies" Oncology, 2007, 73(3-4):261-269.

Petridou et al., "Growth velocity during the first postnatal week of life is not related to adiponectin or leptin" Paediatric and Perinatal Epidemiology, Sep. 2004, 18(5):395.

Petridou et al., "Insulin resistance: an independent risk factor for lung cancer?" Metabolism Clinic and Experimental, Aug. 2011, 60(8):1100-1106.

Petridou et al., "Neonatal leptin levels are strongly associated with female gender, birth length, IGF-I levels and formula feeding" Clinical Endocrinology, Mar. 2005, 62(3):366-371.

Petridou et al., "Plasma Adiponectin Concentrations in Relation to Endometrial Cancer: A Case-Control Study in Greece" J. Clin. Endocrinol Metab, Mar. 2003, 88(3):993-997.

Petridou et al., "Serum Adiponectin As a Predictor of Childhood Non-Hodgkin's Lymphoma:ANationwide Case-Control Study" J Clin Oncol, Oct. 2009, 27(30):5049-5055.

Petzold, "Neurofilament phosphoforms: surrogate markers for axonal injury, degeneration and loss" Journal of the neurological sciences, 233(1-2): 35 pages, Jun. 15, 2005.

(56) References Cited

OTHER PUBLICATIONS

Phan et al., "Adipose tissue dysfunction tracks disease progression in two Huntington's disease mouse models" Human molecular genetics, Mar. 15, 2009, 18(6):1006-1016.
Piguet et al., "Hypoxia aggravates non-alcoholic steatohepatitis in mice lacking hepatocellular PTEN" Clinical Science, Mar. 2010, 118(6):401-410.
Polyzos et al., "Activin A and follistatin in patients with nonalcoholic fatty liver disease" Metabolism, Oct. 2016, 65:1550-1558.
Polyzos et al., "Adipocytokines and cytokeratin-18 in patients with nonalcoholic fatty liver disease: Introduction of CHA index" Sep. 2013, 15;12(5):749-57.
Polyzos et al., "Adipokines in nonalcoholic fatty liver disease" Metabolism, Aug. 2016, 65:1062-1079.
Polyzos et al., "Adiponectin as a potential therapeutic agent for nonalcoholic steatohepatitis" Hepatology Research, 2010, 40:446-447.
Polyzos et al., "Adiponectin as a target for the treatment of nonalcoholic steatohepatitis with thiazolidinediones: A systematic review" Metabolism, Sep. 2016, 65:1297-1306.
Polyzos et al., "Adiponectin in non-alcoholic fatty liver disease treatment: therapeutic perspectives and unresolved dilemmas" Int J Clin Pract, Feb. 2011, 3(65):372-374.
Polyzos et al., "Adipose tissue, obesity and non-alcoholic fatty liver disease" Minerva Endocrinologica, Jun. 2017, 42(2):92-108.
Polyzos et al., "Circulating leptin in non-alcoholic fatty liver disease: a systematic review and meta-analysis" Diabetologia, 2016, 59:30-43.
Polyzos et al., "Irisin in patients with nonalcoholic fatty liver disease" Metabolism, Feb. 2014, 63:207-217.
Polyzos et al., "Leptin in nonalcoholic fatty liver disease: A narrative review" Metabolism, Jan. 2015, 64:60-78.
Polyzos et al., "Necessity for timely noninvasive diagnosis of nonalcoholic fatty liver disease" Metabolism, Feb. 2014, 63(2):161-167.
Polyzos et al., "Nonalcoholic Fatty Liver Disease: The Pathogenetic Roles of Insulin Resistance and Adipocytokines" Current Molecular Medicine, Apr. 2009, 9(3):299-314.
Polyzos et al., "Nonalcoholic fatty liver disease: Updates on associations with the metabolic syndrome and lipid profile and effects of treatment with PPAR-γ agonists" Metabolism, Jan. 2017, 66:64-68.
Polyzos et al., "Nonlinear Distribution of Adiponectin in Patients With Nonalcoholic Fatty Liver Disease Limits Its Use in Linear Regression Analysis" Journal of clinical gastroenterology, Mar. 2010, 44(3):229-30.
Polyzos et al., "Serum total adiponectin in nonalcoholic fatty liver disease: a systematic review and meta-analysis" Metabolism, Mar. 2011,60(3):313-326.
Polyzos et al., "The multi-hit process and the antagonistic roles of tumor necrosis factor-alpha and adiponectin in non-alcoholic fatty liver disease" Hippokratia, Apr. 2009, 13(2):127.
Polyzos et al., "The role of adiponectin in the pathogenesis and treatment of non-alcoholic fatty liver disease" Diabetes, Obesity and Metabolism, May 2010, 12(5):365-383.
Polyzos, "Adiponectin in Health and Disease: Current Evidence and Therapeutic Perspectives" Current Medicinal Chemistry, 2012, 19(32):5425.
Portincasa et al., "Current Pharmacological Treatment of Nonalcoholic Fatty Liver" Current Medicinal Chemistry, Oct. 2006, 13:2889-2900.
Poste et al., "Lipid Vesicles as Carriers for Introdzhg Biologically Active Materials into Cells" Prescott, Ed., Methods in Cell Biology, vol. XIV, Academic Press, New York, N.Y., 1976, Chapter 4, p. 33.
Powell et al., "LX2761, a Sodium/Glucose Cotransporter 1 Inhibitor Restricted to the Intestine, Improves Glycemic Control in Mice" J Pharmacol Exp Ther., Jul. 2017, 362(1):85-97.
Prat et al., "The effect of antidiabetic medications on non-alcoholic fatty liver disease (NAFLD)" Hormones, 17(2):219-229, Jun. 2018.
PUBCHEM. CID 162584226, "Benzenesulfonamide, 2,4-dichloro-N-(3,5-dichloro-4-(3-quinolinyloxy)phenyl)" Oct. 25, 2006 [retrieved on Mar. 22, 2021], retrieved from the Internet. <URL: https://https://pubchem.ncbi.nlm.nih.gov/compound/10229498>, 23 pages.
Pulley, "CCR5 antagonists: from discovery to clinical efficacy" Chemokine Biology—Basic Research and Clinical Application, 2007 vol. II, 145-163, 2007.
Qi et al., "Adiponectin Genetic Variability, Plasma Adiponectin, and Cardiovascular Risk in Patients With Type 2 Diabetes" Diabetes, May 2006, 55(5):1512-1516.
Qi et al., "Dietary Fibers and Glycemic Load, Obesity, and Plasma Adiponectin Levels in Women With Type 2 Diabetes" Diabetes Care, Jul. 2006, 29(7):1501-1505.
Racke et al., "PPARs in Neuroinflammation" PPAR Research, 2008, vol. 2008, Article ID 638356, Hindawi Publishing Corporation.
Raji et al., "Insulin Resistance and Vascular Dysfunction in Nondiabetic Asian Indians" J Clin Endocrinol Metab, Aug. 2004, 89(8):3965-3972.
Rashid et al., "Inhaled sildenafil as an alternative to oral sildenafil in the treatment of pulmonary arterial hypertension (PAH)" Journal of Controlled Release, 250: 23 pages, Mar. 28, 2017.
Rashid et al., "Repurposing rosiglitazone, a PPAR-γ agonist and oral antidiabetic, as an inhaled formulation, for the treatment of PAH" Journal of Controlled Release, 280: 18 pages, Jun. 2018.
Raskin et al., "Rosiglitazone short-term monotherapy lowers fasting and post-prandial glucose in patients with type n diabetes" Diabetologia, 43(3):278-284, Mar. 2000.
Ratziu et al., "Elafibranor, an Agonist of the Peroxisome Proliferator-Activated Receptor-α and -δ, Induces Resolution of Nonalcoholic Steatohepatitis Without Fibrosis Worsening" Gastroenterology, May 2016, 150(5):1147-59.
Ratziu et al., "Nonalcoholic steatohepatitis" Ann. Endocrinol., 2005, 66(2 Pt2): 1S71-1S80.
Ray et al., "Human multiple myeloma cells express peroxisome proliferator-activated receptor γ and undergo apoptosis upon exposure to PPARγ ligands. Clinical Immunology" Nov. 1, 2004, 113(2):203-213.
Reddy et al., "Clinical and genetic predictors of weight gain in patients diagnosed with breast cancer" Br. J. Cancer, Aug. 2013, 109:872-81.
Reeder et al., "Quantitative assessment of liver fat with magnetic resonance imaging and spectroscopy" J Magn Reson Imaging., Oct. 2011, 34(4):729-749.
Remingtons Pharmaceutical Sciences, 18th Ed., Mack Publishing, Easton PA, 1990, Molecular Structure, Properties and States of Matter 26 pages.
Remington's The Science and Practice of Pharmacy, 21st Ed, 2005, Table of Contents, 4 pages.
Ricote et al., "The peroxisome proliferator-activated receptor-gamma is a negative regulator of macrophage activation." Nature, Jan. 1998, 391(6662):79-82.
Rivera et al., "Toll-Like receptor-2 deficiency enhances non-alcoholic steatohepatitis" BMC Gastroenterol., Dec. 2010, 10(1):52.
Ronis et al., "Global Deletion of Glutathione S-Transferase A4 Exacerbates Developmental Nonalcoholic Steatohepatitis" The American Journal of Pathology, Feb. 2017, 187(2):418-430.
Ronis et al., "Medium chain triglycerides dose-dependently prevent liver pathology in a rat model of non-alcoholic fatty liver disease" Exper.Biol. Med., Feb. 2013, 238:151-62.
Rosenstock et al., "Effects of dapagliflozin, an SGLT2 inhibitor, on HbA1c, body weight, and hypoglycemia risk in patients with type 2 diabetes inadequately controlled on pioglitazone monotherapy" Diabetes care, 35(7):1473-1478, Jul. 1, 2012.
Rosenstock et al., "Efficacy and Safety of the Dipeptidyl Peptidase-4 Inhibitor Sitagliptin Added to Ongoing Pioglitazone Therapy in Patients with Type 2 Diabetes: A 24-Week, Multicenter, Randomized, Double-Blind, Placebo-Controlled, Parallel-Group Study" Clinical Therapeutics, Oct. 2006, 28(10): 1556-68.
Rossi et al., "Neuroinflammation drives anxiety and depression in relapsing-remitting multiple sclerosis", Neurology, Sep. 2007, 89(13):1338-47.
Roth et al., "Combined obeticholic acid and elafibranor treatment promotes additive liver histological improvements in a diet-induced ob/ob mouse model of biopsy-confirmed NASH" Scientific reports, 9(1):1-3, Jun. 21, 2019.

(56) References Cited

OTHER PUBLICATIONS

Roth et al., "Vitamin D Deficiency in Obese Rats Exacerbates Nonalcoholic Fatty Liver Disease and Increases Hepatic Resistin and Toll-Like Receptor Activation" Hepatology, Apr. 2012, 55(4):1103-11.

Ruschke et al., "Gene expression of PPARg and PGC-1a in human omental and subcutaneous adipose tissues is related to insulin resistance markers and mediates beneficial effects of physical training" Eur. J. Endocrinol., 2010, 162:515-23.

Rusli et al., "Fibroblast growth factor 21 reflects liver fat accumulation and dysregulation of signalling pathways in the liver of C57BL/6J mice" Sci. Rep., Jul. 2016, 6:30484, 16 pages.

Saeed et al., "Disturbed vitamin A metabolism in non-alcoholic fatty liver disease (NAFLD)" Nutrients, 10(1):29, 25 pages, Jan. 2018.

Sahebkar et al., "New peroxisome proliferator-activated receptor agonists: potential treatments for atherogenic dlyslipidemia and non-alcoholic fatty liver disease" Expert Opin Pharmacother, Mar. 14, 15(4):493-503.

Sahebkar et al., "Role of selective peroxisome proliferator-activated receptor modulators in managing cardiometabolic disease: tale of a roller-coaster" Diabetes, Obesity and Metabolism, 16(9):780-792, Sep. 2014.

Sahin-Efe et al., "Advances in adipokines" Metabolism, Dec. 2012, 61(12): 1659-1665.

Sai et al., "Systematic design of trypsin cleavage site mutated exendin4-cysteine 1, an orally bioavailable glucagon-like peptide-1 receptor agonist" International journal of molecular sciences, 18(3):578, Mar. 2017.

Sakauchi et al., "Pleiotropic properties of ASK1. Biochimica et Biophysica Acta (BBA)-General Subjects" 1861(1):3030-3038, Jan. 1, 2017.

Sanyal et al., "LB-23 Tropifexor (TXR), an FXR Agonist for the Treatment of Nash—Interim Results from First Two Parts of Phase 2b Study Flight-FXR" Hepatology, 68(1): 2 pages Oct. 1, 2018.

Sanyal et al., "Piolitazone, Vitamin E, or Placebo for Nonalcoholic Steatohepatits" The New England Journal of Medicine, May 2010, 362(18):1675-1685.

Sarafidis et al., "Protection of the kidney by thiazolidinediones: An assessment from bench to bedside" Kidney International, Oct. 2006, 70(7):1223-1233.

Satapathy et al., "Epidemiology and Natural History of Nonalcoholic Fatty Liver Disease." Semin Liver Dis., Aug. 2015, 35(3):221-235.

Sato et al., "Vitamin E has a beneficial effect on nonalcoholic fatty liver disease: a meta-analysis of randomized controlled trials" Nutrition, 31(7-8): 22 pages, Jul. 1, 2015.

Scheen, "Cardiovascular Effects of New Oral Glucose-Lowering Agents" Circ Res, May 2018, 122(10):1439-1459.

Scheer et al., "Day/night variations of high-molecular-weight adiponectin and lipocalin-2 in healthy men studied underfed and fasted conditions" Diabetologia, Nov. 2010, 53(11):2401-5.

Schmidt et al., "Anti-inflammatory and antiproliferative actions of PPAR-y agonists on T lymphocytes derived from MS patients" Journal of Leukocyte Bilogy, Mar. 2004, 75(3):478-85.

Schreuder et al., "The hepatic response to FGF19 is impaired in patients with nonalcoholic fatty liver disease and insulin resistance." Gastrointest., Physiol., Mar. 2010, 298(3):G440-445.

Schultz et al., "Hepatic Adverse Effects of Fructose Consumption Independent of Overweight/Obesity" Int. J. Mol. Sci., Nov. 2013, 14:21873-86.

Scorletti et al., "Omega-3 Fatty Acids, Hepatic Lipid Metabolism, and Nonalcoholic Fatty Liver Disease" Ann. Rev. Nutr., Jul. 2013, 33:231-248.

SealRocktx.com [Online], "Seal Rock Therapeutics Advancing Differentiated ASK1 Inhibitor Lead Candidate SRT-015 in Nonalcoholic Steatohepatitis (NASH)" retrieved from the internet URL<https://www.prnewswire.com/news-releases/seal-rock-therapeuticsadvancing-differentiated-ask1-inhibitor-lead-candidate-srt-015-innonalcoholic-steatohepatitis-nash-3007 47392~html>, 4 pages.

Sebokova et al., "Dipeptidyl Peptidase IV Inhibitors: The Next Generation of New Promising Therapies for the Management of Type 2 Diabetes" Current Topics in Medicinal Chemistry, Mar. 2007, 7(6):547-555.

Seidah et al., "The secretory proprotein convertase neural apoptosis-regulated convertase 1 (NARC-1): Liver regeneration and neuronal differentiation" Proc. Nat. Acad Sci. USA, Feb. 2003, 100(3):928-33.

Serviddio et al., "Free radical biology for medicine: learning from nonalcoholic fatty liver disease" Free Radical Biology and Medicine, Dec. 2013, 65:952-968.

Seth et al., "Environmental Toxin-Linked Nonalcoholic Steatohepatitis and Hepatic Metabolic Reprogramming in Obese Mice" Toxicological Sci., Aug. 2013, 134(2):291-303.

Shah et al., "MicroRNAs in Liver Disease: Bench to Bedside" Journal of Clinical and Experimental Hepatology, Sep. 2013, 3(3):231-242.

Shalini et al., "Old, new and emerging functions of caspases" Cell Death Differ., Apr. 2015, 22(4):526-539.

Shapiro and Brack, "Therapeutic potential of curcumin in non-alcoholic steatohepatitis" Nutr. Res. Rev., Dec. 2005, 18(2):212-21.

Sharma et al., "The Riddle of Nonalcoholic Fatty Liver Disease: Progression From Nonalcoholic Fatty Liver to Nonalcoholic Steatohepatitis" Journal of Clinical and Experimental Hepatology, Jun. 2015, 5(2):147-158.

Shea et al., "Independent Circadian and Sleep/Wake Regulation of Adipokines and Glucose in Humans" J. Clin. Endocrinol. Metab., May 2005, 90(5):2537-44.

Sher et al., "Relationship Between Serum Adiponectin and Prostate Cancer Grade" The Prostate, Oct. 2008, 68(14):1592-8.

Shetty et al., "Circulating Adiponectin and Resistin Levels in Relation to Metabolic Factors, Inflammatory Markers, and Vascular Reactivity in Diabetic Patients and Subjects at Risk for Diabetes" Diabetes Care, Oct. 2004, 27(10):2450-7.

Shi et al., "Effects of apigenin on protein expressions of PPARs in liver tissues of rats with nonalcoholic steatohepatitis" Clin. J. Hepatol., Feb. 2015, 23(2):124-9.

Shi, "Caspase Activation: Revisiting the Induced Proximity Model" Cell, Jun. 2004, 117(7):855-858.

Shieh et al., "Increase of hepatic fat accumulation by liver specific expression of Hepatitis B virus X protein in zebrafish" Biochimica et Biophysica Acta, Jul. 2010, 1801(7):721-730.

Shih et al., "Synergistic Effect of Cyanidin and PPAR Agonist against Nonalcoholic Steatohepatitis-Mediated Oxidative Stress-Induced Cytotoxicity through MAPK and Nrf2 Transduction Pathways" J. Agric. Food Chem., Mar. 2012, 60(11):2924-33.

Shinoda et al., "Regulation of bone formation by adiponectin through autocrine/paracrine and endocrine pathvvays" Journal of Cellular Biochemistry, Sep. 2006, 99(1):196-208.

Shiri-Sverdlov et al., "Early diet-induced non-alcoholic steatohepatitis in APOE2 knock-in mice and its prevention by fibrates" Journal of Hepatology, Apr. 2006, 44:732-741.

Siuly et al., "Medical big data: neurological diseases diagnosis through medical data analysis" Data Science and Engineering, Jun. 1, 2016, 1(2):54-64.

Sleilati et al., "Efficacy and safety of pioglitazone in treatment of a patient with an atypical partial lipodystrophy syndrome." Pioglitazone and Lipodystrophy, Endocr Pract., Oct. 2007, 13(6):656-61.

Smith et al., "Clinical worsening in multiple sclerosis is associated with increased frequency and area of gadopentetate dimeglumine-enhancing magnetic resonance imaging lesions" Ann Neurol, May 1993, 33(5):480-9.

Sohn et al., "Lactobacillus paracasei Induces M2-Dominant Kupffer Cell Polarization in a Mouse Model of Nonalcoholic Steatohepatitis" Dig. Dis. Sci., Nov. 2015, 60:3340-50.

Sorrentino et al., "A clinical-morphological study on cholestatic presentation of nonalcoholic fatty liver disease." Dig Dis Sci., Jun. 2005, 50(6):1130-1135.

Souza-Mello, "Peroxisome proliferator-activited receptors as targets to treat non-alcoholic fatty liver disease" World J Hepatol., May 2015, 7(8):1012-1019.

(56) References Cited

OTHER PUBLICATIONS

Spatola et al., "SGLT1 and SGLT1 inhibitors: a role to be assessed in the current clinical practice" Diabetes Therapy, 9(1):427-430, Feb. 2018.
Spyridopoulos et al., "Low adiponectin levels are associated with renal cell carcinoma: A case-control study" Int. J. Cancer, Apr. 2007, 120(7):1573-8.
Staels et al., "Hepatoprotective Effects of the Dual Peroxisome Proliferator-Activated Receptor Alpha/Delta Agonist, GFT505, in Rodent Models of Nonalcoholic Fatty Liver Disease/Nonalcoholic Steatohepatitis" Hepatology, Dec. 2013, 58:1941-52.
Stefano et al., "Nonalcoholic Steatohepatitis (NASH) in OB/OB Mice Treated with Yo Jyo Hen Shi Ko (YHK): Effects on Peroxisome Proliferator-Activated Receptors (PPARs) and Microsomal Triglyceride Transfer Protein (MTP)" Dig. Dis. Sci., Dec. 2007, 52(12):3448-54.
Steinman et al., "Piet Mondrian's trees and the evolution in understanding multiple sclerosis, Charcot Prize Lecture 2011" Jan. 2013, Multiple Sclerosis Journal, 19(1):5-14.
Steinman et al., "Virtues and pitfalls of EAE for the development of therapies for multiple sclerosis" Trends in Immunology, Nov. 2005, 26(11):565-71.
Stephen et al., "Nonalcoholic Fatty Liver Disease and Bariatric Surgery" Expert Rev Gastroenterol Hepatol, Apr. 2012, 5(2):163-171.
Storer et al., "Peroxisome proliferator-activated receptor-gamma agonists inhibit the activation of microglia and astrocytes: Implications for multiple sclerosis" Journal of Neuroimmunology, Apr. 2005, 161(1-2):113-22.
Strum et al., "Rosiglitazone induces mitochondrial biogenesis in mouse brain" Jan. 2007, 11(1):45-51.
Struthers et al., "CCR2 antagonists" Current topics in medicinal chemistry, Sep. 1, 2010, 10(13):1278-1298.
Stuebe et al., "Duration of Lactation and Maternal Adipokines at 3 Years Postpartum" Diabetes, Apr. 2011, 60:1277-85.
Stuebe et al., "Gestational Glucose Tolerance and Maternal Metabolic Profile at 3 Years Postpartum" Obsterics & Gynecology, Nov. 2011, 118(5):1065-1073.
Su et al., "A novel therapy for colitis utilizing PPARgamma ligands to inhibit the epitheliah inflammatory response" The Journal of Clinical Investigation, Aug. 1999, 104(4):383-9.
Sumida et al., "Current and future pharmacological therapies for NAFLD/NAS" Journal of gastroenterology, 53(3): 15 pages, Mar. 2018.
Sun et al., "Leptin and Soluble Leptin Receptor Levels in Plasma and Risk of Type 2 Diabetes in U.S. Women" Diabetes, Mar. 2010, 59(3):611-8.
Svegliati-Baroni et al., "A Model of Insulin Resistance and Nonalcoholic Steatohepatitis in Rats" The American Journal of Pathology, Sep. 2006, 169(3):846-860.
Svegliati-Baroni et al., "Glucagon-like peptide-1receptor activation stimulates hepatic lipid oxidation and restores hepatic signalling alteration induced bya high-fat diet in nonalcoholic steatohepatitis" Liver Internatl., Oct. 2011, 31(9):1285-97.
Sweeney et al., "The role of adipokines in relation to HIV lipodystrophy" AIDS, May 2007, 21:895-904.
Tacke, "Cenicriviroc for the treatment of non-alcoholic steatohepatitis and liver fibrosis." Expert Opin Investig Drugs, Mar. 2018, 27(3):301-311.
Tahan et al., "Rosiglitazone Attenuates Liver Inflammation in a Rat Model of Nonalcoholic Steatohepatitis" Dig. Dis. Sci., Apr. 2007, 52:3465-72.
Takahashi et al., "Inhibitory Effects of Japanese Herbal Medicines Sho-saiko-to and Juzen-taiho-to on Nonalcoholic Steatohepatitis in Mice" PLoS One, Jan. 2014, 9(1):e87279.
Tanaka and Aoyama, "PPAR and NASH" Japanese Journal of Clinical Medicine, 2006, 64(6):1089-94, English abstract.
Tanaka et al., "Dysregulated expression of fatty acid oxidation enzymes and iron-regulatory genes in livers of Nrf2-null mice" J. Gastroenterol. Hepatol., Nov. 2012, 27(11):1711-7.
Tanaka et al., "Role of fiboblast growth factor 21 in the early stage of NASH induced by methionine-and choline-deficient diet" Biochimica et Biophysica Acta, Jul. 2015, 1852(7):1242-1252.
Tanaka, et al., "Role of PPARs in the pathophysiology of nonalcoholic fatty' liver disease" Japanese Journal of Clinical Medicine, Apr. 2005, 63(4):700-706, English abstract.
Tang et al., "Curcumin Eliminates Leptin's Effects on Hepatic Stellate Cell Activation via Interrupting Leptin Signaling" Endocrinology, Jul. 2009, 150(7):3011-20.
Tarantino et al., "Pathogenesis of hepatic steatosis: the link between hypercortisolism and nonalcoholic fatty liver disease." W. J. Gastroenterol., Oct. 2013, 19(40):6735-6743.
Taygerly et al., "Discovery of INT131: A selective PPAR-gamma modulator that enhances insulin sensitivity" Bioorg Med Chem, Feb. 2013, 21(4):979-992.
Taylor et al., "Health Impact Analysis of Cisplatin, Carboplatin and Oxaliplatin: Quantifying the health impact of platinum compounds" Johnson Matthey Technology Review, Jan. 2017, retrieved from URL <www.technology.matthey.com/article/61/1/32-39/>, 32-39.
Tella et al., "Prevention and treatment of postmenopausal osteoporosis" The Journal of steroid biochemistry and molecular biology, Jul. 1, 2014, 142:155-170.
Teoh et al., "Short-Term Therapy with Peroxisome Proliferation-Activator Receptor-Agonist Wy-14,643 Protects Murine Fatty Liver Against Ischemia-Reperfusion Injury" Hepatology, Mar. 2010, 51(3):996-1006.
Terao et al., "Design and biological evaluation of imidazo [1, 2-a] pyridines as novel and potent ASK1 inhibitors" Bioorganic & medicinal chemistry letters, 22(24):7326-7329, Dec. 15, 2012.
The United States Pharmacopeia, 23rd Ed., 1995, pp. 1843-1844.
Thorkildsen et al., "Glucagon-like peptide 1 receptor agonist ZP10A increases insulin mRNA expression and prevents diabetic progression in db/db mice." J. Pharmacol Exp Ther., Nov. 2003, 307(2):490-496.
Tilg et al., "Evolving therapies for non-alcoholoic steatohepatitis" Expert Opin. Drug Discov., Apr. 2014, 9(6):687-696.
Tolbol et al., "Metabolic and hepatic effects of liraglutide, obeticholic acid and elafibranor in diet-induced obese mouse models of biopsy-confirmed nonalcoholic steatohepatitis" World Journal of Gastroenterology, 24(2): 17 pages, Jan. 14, 2018.
Tomita et al., "Free Cholesterol Accumulation in Hepatic Stellate Cells: Mechamsm of Liver Fibrosis Aggravation in Nonalcoholic Steatohepatitis in Mice" Hepatology, Jan. 2014, 59(1):154-69.
Tomita et al., "Hepatic AdipoR2 Signaling Plays a Protective Role Against Progression of Nonalcoholic Steatohepatitis in Mice" Hepatology, Aug. 2008, 48(2):458-73.
Tong, "Acetyl-coenzyme A carboxylase: crucial metabolic enzyme and attractive target for drug discovery." Cell. Malec. Life Sci., Aug. 2005, 62(16):1784-1803.
Tourdias et al., "Neuroinflammatory imaging biomarkers: relevance to multiple sclerosis and its therapy" Neurotherapeutics, Jan. 2013, 10(1):111-123.
Tsiodras and Mantzoros, "Leptin and Adiponectin in the HIV Associated Metabolic Syndrome: Physiologic and Therapeutic Implications" Am. J. Infectious Dis., 2006, 2(3):141-52.
Tsiodras, et al., "The HIV-1/HAART associated metabolic syndrome—Novel adipokines, molecular associations and therapeutic implications" Journal of Infection, Aug. 2010, 61(2):101-113.
Tsukamoto et al., "Fat paradox of steatohepatitis" J. Gastroenterol. Hepatol., Mar. 2008, 23(Suppl. 1):S104-7.
Turton et al., "A role for glucagon-like peptide-I in the central regulation of feeding." Nature, Jan. 1996, 379(6560):69-72.
Tushuizen et al."Incretin mimetics as a novel therapeutic option for hepatic steatosis". Liver Int., Oct. 2006, 26(8):1015-1017.
Tworoger et al., "Plasma Adiponectin Concentrations and Risk of Incident Breast Cancer" J Clin Endocrinol Metab, Apr. 2007, 92(4):1510-1516.
Tworoger et al., "Relationship of Plasma Adiponectin With Sex Hormone and Insulin-like Growth Factor Levels" Obesity, Sep. 2007, 15(9):2217-2224.
Tziomalos et al., "Nonalcoholic fatty liver disease and stains" Metabolism, Oct. 2015, 64(10):1215-1223.

(56) References Cited

OTHER PUBLICATIONS

Uno et al., "Tranilast, an Antifibrogenic Agent, Ameliorates a Dietary Rat Model of Nonalcoholic Steatohepatitis" Hepatology, Jul. 2008, 48(1):109-18.
USP.org [online], "711 Dissolution" Dec. 1, 2011, retrieved Sep. 30, 2021, retrieved from URL <https://www.usp.org/sites/default/files/usp/document/harmonization/gen-method/stage_6_monograph Feb. 25, 2011.pdf>, 8 pages.
Uto, et al., "The peroxisome proliferator-activated receptor-gamma agonist, pioglitazone, inhibits fat accumulation and fibrosis in the livers of rats fed a choline-deficient, L-amino acid-defined diet" Hepatology Research, Aug. 2005, 32:235-242.
Vaddi, "TNF Signaling Pathway Inhibitors For Inflammation-CCR2 Antagonists" Target Validation in Drug Discovery, Jan. 1, 2007, Academic Press, 223-240.
Vamvini et al., "Differential Effects of Oral and Intravenous Lipid Administration on Key Molecules Related to Energy Homeostasis" J. Clin Endocrinol Metab, May 2016, 101(5):1989-1997.
Vamvini et al., "Irisin mRNA and circulating levels in relation to other myokines in healthy and morbidly obese humans" European Journal of Endocrinology, Dec. 2013, 169(6):829-834.
Van Herek et al., "Animal Models of Nonalcoholic Fatty Liver Disease—A Starter's Guide" Nutrients., Oct. 2017, 9(10):1072, 13 pages.
Van Raalte et al., "Peroxisome Proliferator-Activated Receptor (PPAR)-α: A Pharmacological Target with a Promising Future" D.H., Pharm Res., Sep. 2004, 21(9):1531-1538.
Vanni, et al., "From the metabolic syndrome to NAFLD or vice versa?" Digestive and Liver Disease, May 2010, 42:320-330.
Varhaug et al., "Neurofilament light chain predicts disease activity in relapsing-remitting MS" Neurology—Neuroimmunology Neuroinflammation, Jan. 2018, 5(1): p. e422.
Velayudham et al., "VSL#3 Probiotic Treatment Attenuates Fibrosis Without Changes in Steatohepatitis in a Diet-Induced Nonalcoholic Steatohepatitis Model in Mice" Hepatology, Mar. 2009, 49(3):989-97.
Verdi et al., "Peroxisome Proliferator-Activated Receptor α L162 V Polymorphism in Nonalcoholic Steatohepatitis and Genotype 1 Hepatitis C Virus-Related Liver Steatosis" Journal of investigative medicine, Nov. 2005, 53(7):353-9.
Vernon et al., "Systematic review: the epidemiology and natural history of non-alcoholic fatty liver disease and non-alcoholic steatohepatitis in adults" Aliment Pharmacol Ther., Aug. 2011, 34(3):274-285.
Villegas et al., "Rosiglitazone, an agonist of peroxisome proliferator-activated receptor gamma, protects against gastric ischemia-reperfusion damage in rats: role of oxygen free radicals generation" European Journal of Phamacology, Nov. 2004, 505(1-3):195-203.
Villhauer et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties" J Med Chem, Jun. 2003, 46(13):2774-2789.
Villhauer et al., "1-[2-[(5-Cyanopyridin-2-yl)amino]ethylamino]acetyl-2-(S)-pyrrolidinecarbonitrile: A Potent, Selective, and Orally Bioavailable Dipeptidyl Peptidase IV Inhibitor with Antihyperglycemic Properties" J Med Chem, Jun. 2002, 45(12):2362-2365.
Von Tils et al., "Type II secretion in Yersinia—a secretion system for pathogenicity and environmental fitness" Front. Cell Infect. Microbial., Dec. 2012, 2(160):1-11.
Wada et al., Eplerenone ameliorates the phenotypes of metabolic syndrome with NASH in liver-specific SREBP-1c Tg mice fed high-fat and high-fructose diet:, Am. J. Physiol. Endocrinol. J. Phy., Dec. 2013, 305(11):E1415-E1425.
Walker et al., "Subcutaneous Abdonninai Adipose Tissue Subcompartments: Potential Role in Rosiglitazone Effects" Obesity, Sep. 2008, 16(9):1983-1991.
Walter, et al., "Adiponectin reduces connective tissue growth factor in human hepatocytes which is already induced in non-fibrotic non-alcoholic steatohepatitis" Experimental and Molecular Pathology, Dec. 2011, 91:740-744.

Wang et al. "Peroxisome proliferator-activated receptor gamma in malignant diseases" Critical 1-59 Reviews in Oncology/Hematology, Apr. 2006, 58(1):1-14.
Wang et al., "Stat3-Mediated Activation of MicroRNA-23a Suppresses Gluconeogenesis in Hepatocellular Carcinoma by Down-Regulating Glucose-6-Phosphatase and Peroxisome Proliferator-Activated Receptor gamma, Coactivator 1 Alpha" Hepatology, Jul. 2012, 56(1):186-97.
Wang et al., "Targeting CASP8 and FADD-like apoptosis regulator ameliorates nonalcoholic steatohepatitis in mice and nonhuman primates" Nat. Med, Apr. 2017, 23(4):439-449.
Wang, et al., "Association between the Pro12A1a polymorphism of PPAR-gamma gene and the non-alcoholic fatty liver disease" Gene, Oct. 2013, 528:328-334.
Wang, et al., "Molecular regulation of miRNAs and potential biomarkers in the progression of hepatic steatosis to NASH" Biomark. Med., Nov. 2015, 9(11):1189-1200.
Wang, et al., "Raspberry ketone protects rats fed high-fat diets against nonalcoholic steatohepatitis" J. Med. Food., May 2012, 15(5):495-503.
Watson et al., "Pulmonary hypertension: old targets revisited (statins, PPARs, beta-blockers)" Pharmacotherapy of Pulmonary Hypertension, 531-548, 2013.
Weber, "Dipeptidyl peptidase IV inhibitors for the treatment of diabetes." J. Med. Chem., Aug. 2004, 47:4135-4141.
Wedick et al., "Effects of caffeinated and decaffeinated coffee on biological risk factors for type 2 diabetes: a randomized controlled trial" Nutrition Journal, Dec. 2011, 10(1):93, 9 pages.
Wei et al., "Low Plasma Adiponectin Levels and Risk of Colorectal Cancer in Men: A Prospective Study" J Natl Cancer Inst., Nov. 2005, 97(22):1688-1694.
Werner, "Preclinical pharmacology of the new GLP-1 receptor agonist A VE0010." Ann Endocrinol (Paris), 2008, 69(2):164-5.
Williams et al., "Adiponectin receptor expression is elevated in colorectal carcinomas but not in gastrointestinal stromal tumors" Endocrine-Related Cancer, Mar. 2008, 15(1):289-99.
Williams et al., "Coffee Consumption Is Associated With Higher Plasma Adiponectin Concentrations in Women With or Without Type 2 Diabetes" Diabetes Care, Mar. 2008, 31:504-507.
Williams et al., "Sleep Duration and Snoring in Relation to Biomarkers of Cardiovascular Disease Risk Among Women With Type 2 Diabetes" Diabetes Care, May 2007, 30(5): 1233-1240.
Wolfe et al., "Effect of dieting on plasma leptin, soluble leptin receptor, adiponectin and resistin levels in healthy volunteers" Clinical Endocrinology, Sep. 2004, 61(3):332-338.
Wright, "Renal Na+-glucose cotransporters" Am J Physiol Renal Physiol., Jan. 2001, 280:F10, 9 pages.
Wu et al., "Dietary fucoxanthin increases metabolic rate and upregnlated mRNA expressions of the PGC-1alpha network, mitochondrial biogenesis and fusion genes in white adipose tissues of mice." Afarine Drugs, Feb. 2014, 12(2):964-982.
Wu et al., "PPARg is essential for protection against nonalcoholic steatohepatitis" Gene Therapy, Jun. 2010, 17(6):790-798.
Xia et al., "Characterization of long noncoding RNA transcriptome in highenergy diet induced nonalcoholic steatohepatitis minipigs" Scientific Reports, Jul. 2016. 6:30709, 11 pages.
Xia et al., "Transcriptome Analysis on the Inflammatory Cell Infiltration of Nonalcoholic Steatohepatitis in Bama Minipigs Induced by a Long-Term High-Fat, High-Sucrose Diet" PLoS ONE, Nov. 2014, 9(11):e113724.
Yaghoubi et al., "Comparison of fenofibrate and pioglitazone effects on patients with nonalcoholic fatty liver disease" European journal of gastroenterology & hepatology, 29(12): 4 pages, Dec. 1, 2017.
Yakaryilmaz et al., "Effects of vitamin E treatment on peroxisome proliferatoractivated receptor-a expression and insulin resistance in patients with non-alcoholic steatohepatitis: results of a pilot study" Internal Medicine Journal, Apr. 2007, 37(4):229-235.
Yamada et al., "Characteristics of hepatic fatty acid compositions in patients with nonalcoholic steatohepatitis" Liver International ISSN, 2014, 1478-3223.
Yamada et al., "Suppressive Role of PPARγ-Regulated Endothelial Nitric Oxide Synthase in Adipocyte Lipolysis" PLoS ONE, Aug. 2015, 10(8):e0136597, 15 pages.

(56) References Cited

OTHER PUBLICATIONS

Yamaguchi et al., "Blockade of interleukin-6 signaling enhances hepatic steatosis but improves liver injury in methionine choline-deficient diet-fed mice" Laboratory Investigation, Aug. 2010, 90(8):1169-1178.
Yang et al., "Low vitamin D status is associated with advanced liver fibrosis in patients with nonalcoholic fatty liver disease" Endocrine, 55(2): 9 pages, Feb. 1, 2017.
Yang et al., "Regulation of Immune Responses and Autoimmune Encephalomyelitis by PPARs" PPAR Research, 2010, vol. 2010, Article ID 104705, 11 pages.
Yang et al., "Role of PPARgamma in renoprotection in Type 2 diabetes: molecular mechanisms and therapeutic potential" Clinical Science, Jan. 2009, 116(1):17-26.
Yang et al., "The emerging role of adiponectin in cerebrovascular and neurodegenerative diseases" Biochimica et Biophysica Acta, Sep. 2015, 1852(9):1887-1894.
Yannakoulia et al., "Body Fat Mass and Macronutrient Intake in Relation to Circulating Soluble Leptin Receptor, Free Leptin Index, Adiponectin, and Resistin Concentrations in Healthy Humans" Clin Endocrinol Metab, Apr. 2003, 88(4):1730-1736.
Yannakoulia et al., "Dietary factors associated with plasma high molecular weight and total adiponectin levels in apparently healthy women" European Journal of Endocrinology, Oct. 2008, 159(4):R5-R10.
Yannakoulia, et al., "A dietary pattern characterized by high consumption of whole-grain cereals and low-fat dairy products an dlow consumption of refined cereals is positively associated with plasma adiponectin levels in healthy women" Metabolism Clinical and Experimental, Jun. 2008, 57(6):824-830.
Yew et al., "Selective peroxisome proliferator-activated receptor-gamma modulation to reduce cardiovascular risk in patients with insulin resistance" Recent Pat on Cardiovasc Drug Discove, Apr. 2012, 7(1):33-41.
Yki-Jarvinen et al., "The fatty liver and insulin resistance" Current molecular medicine, May 2005, 5(3):287-95.
Yoneda et al., "Life Style-Related Diseases of the Digestive System: Gene Expression in Nonalcoholic Steatohepatitis Patients and Treatment Strategies" J Pharmacol Sci., Jan. 2007, 105(2):151-156.
Yoneda et al., "PPAR gamma ligand pioglitazone as a therapeutic strategy in nonalcoholic steatohepatitis (NASH)" Folia Pharmacol. Jpn., Oct. 2006; 128(4):235-238.
Yuan et al., "Cardioprotective effects of peroxisome proliferator activated receptor gamma activators on actue myocarditis: anti-inflammatory actions associated with nuclear factor kappaB blockade" Heat, 91: 1203-1208, 2005.
Zamanian et al., "Insulin resistance in pulmonary arterial hypertension" European respiratory journal, 33(2):318-324, Feb. 1, 2009.
Zambon et al., "The role of fenofibrate in clinical practice" Diabetes Vasc Dis Res., Sep. 2007, 4(suppl 3):S15-S20.
Zhan et al., "Protective effect of probucol on liver injury induced by carbon tetrachloride in rats" Hepatology international, 5(4):899-905, Dec. 2011.
Zhang et al., "Peroxisome proliferator-activated receptor (PPAR) alpha and -gamma regulate IFNgamma and IL-17A production by human T cells in a sex-specific way" PNAS, Jun. 2012, 109(24):9505-10.
Zhang et al., "Selective Modulators of PPARy Activity: Molecular Aspects Related to Obesity and Side-Effects" PPAR Research, 2007, vol. 2007, 7 pages.
Zhang, et al., "Association between resistin + 299A/A genotype and nonalcoholic fatty liver disease in Chinese patients with type 2 diabetes mellitus" Gene, Oct. 2013, 529:340-344.
Zhang, et al., "PPARalpha/gamma and antagonists differently affect hepatic lipid metabolism, oxidative stress and inflammatory cytokine production in steatohepatitic rats" Cytokine, Sep. 2015, 75:127-135.
Zhao et al., "An experimental study on the reverse mechanism of PPAR-Y agonist rosiglitazone in rats with non-alcoholic steatohepatitis" Chin. J. Hapatol., Jun. 2007, 15(6):450-455.
Zhao et al., "Pioglitazone ameliorates nonalcoholic steatohepatitis by down-regulating hepatic nuclear factor-kappa B and cyclooxygenases-2 expression in rats" Chin Med J., Jan. 2012, 125(13):2316-2321.
Zheng et al., "Fish consumption and CHD mortality: an updated meta-analysis of seventeen cohort studies" Public Health Nutr., Apr. 2012, 15(4):725-737.
Zheng, et al., "Exposure to ambient particulate matter induces a NASH-like phenotype and impairs hepatic glucose metabolism in an animal model" Journal of Hepatology, Jan. 2013, 58:148-154.
Ziamajidi, et al., "Amelioration by chicory seed extract of diabetes- and oleic acid-induced non-alcoholic fatty liver disease (NAFLD)/non-alcoholic steatohepatitis (NASH) via modulation of PPARalpha and SREBP-1" Food and Chemical Toxicology, Aug. 2013, 58:198-209.
Ziemke et al., "Adiponectin in insulin resistance: lessons from translational research" Am J Clin Nutr., Jan. 2010, 91(suppl):258S-61S.
Zou, et al., "High-fat emulsion-induced rat model of nonalcoholic steatohepatitis" Life Sciences, Aug. 2006, 79:1100-1107.

PPARγ AGONIST FOR TREATMENT OF PROGRESSIVE SUPRANUCLEAR PALSY

CROSS-REFERENCE TO RELATED APPLICATIONS

This application is a National Stage application under 35 U.S.C. § 371 of International Patent Application Serial No. PCT/US2018/025923, filed Apr. 3, 2018, which claims priority to U.S. Provisional Patent Application Ser. No. 62/480,838, filed Apr. 3, 2017, and U.S. Provisional Patent Application Ser. No. 62/651,653, filed Apr. 2, 2018; the entire contents of all of which are herein incorporated by reference.

FIELD OF THE INVENTION

The present invention relates to methods of treatment of progressive supranuclear palsy. The present invention also relates, at least in part, to methods using CHS-131 for the treatment of subjects having an elevated level of neurofilament light chain protein in a sample comprising cerebrospinal fluid, blood, serum, or plasma that has been obtained from the subject (e.g., as compared to a reference level of neurofilament light chain protein).

BACKGROUND OF THE INVENTION

Neurological disorders can cause permanent and irreversible damage that can affect a patient's quality of life, such as speech, cognitive skills, motor skills, and metabolism. Treatments that would delay the onset of symptoms of a neurological disorder in a subject are desired for patients that are diagnosed as being in the early or middle stages of a neurological disorder.

Progressive Supranuclear Palsy (PSP), a relentless and fatal tauopathy, accounts for ~10% of all parkinsonian cases in the U.S. Patients with PSP present with a variety of motor dysfunctions, including postural instability, falls, gait abnormalities, bradykinesia, vertical gaze palsy, pseudobulbar palsy, and axial rigidity without limb rigidity, as well as cognitive impairments including apathy, loss of executive function, and diminished fluency. The neuropathology of PSP is characterized by an accumulation of abnormal intracellular microtubule-associated protein tau, resulting in insoluble paired helical filaments. The neuropathological presentation of PSP neurodegeneration is localized to the subcortical regions including substantia nigra, globus palladus, and the subthalamic nucleus. The neurodegeneration of PSP is characterized by tissue destruction and cytokine profiles of the activated microglia and astrocytes. These findings are consistent with these activated glial cells as the local sources inflammation and oxidative stress in PSP.

There are approximately 1,400 new diagnosis of PSP per year in the US, with a mean survival 5.9-6.9 years. There are currently no disease modifying treatments for PSP. The current standard of care is palliative. Patients in the advanced stages of the disease often have feeding tubes inserted to avoid choking risks and to provide nutrition.

While there are therapies available to lessen some symptoms of PSP, none protect the brain or slow the deterioration of nerve cells. Current medications to treat symptoms of PSP include dopamine agonists, tricyclic antidepressants, methysergide, Onabotulinumtoxin A (to treat muscle rigidity in the face). However, as the disease progresses, and symptoms worsen, medications may fail to adequately lessen the symptoms.

Accordingly, there is need for new safe and effective treatments of progressive supranuclear palsy.

SUMMARY OF THE INVENTION

It has now been discovered that the peroxisome proliferator-activated receptor gamma (PPARγ) agonist INT131 (CHS131) is effective for treating progressive supranuclear palsy ("PSP"). The PPARγ is a transcription factor belonging to the superfamily of ligand-activated transcription factors, including the steroid, thyroid, and retinoid receptors [Thiemermann, 2004 #12090]. To date, PPARγ agonists have been therapeutic agents for disorders of metabolism, including obesity, Type 2 diabetes mellitus, and dyslipidemia. Recently, the novel, selective PPARγ agonist, CHS-131 has been shown to decrease inflammation and to be neuroprotective in patients with relapsing remitting Multiple Sclerosis.

In one aspect, the present invention provides methods of treating progressive supranuclear palsy and symptoms thereof. The methods typically involve administering to a subject in need thereof a therapeutically effective amount of compound INT131 described in U.S. Pat. No. 7,601,841. INT131 is unique among PPARγ agonists in that it exerts potent anti-inflammatory effects in the central nervous system without evidence of systemic immunosuppression and is a selective activator of a highly limited number of PPARγ pathways. Among these INT131-sensitive pathways are metabolic pathways including those pathways regulated by the hormone adiponectin.

As a result of this selective activation, administration of INT131 to patients results in fewer side effects than administration of other PPARγ agonists. For example, INT131 was equally efficacious in reducing HbA1c levels as 45 mg of pioglitazone but subjects taking INT131 experienced less edema, weight gain, and hemodilution than those taking pioglitazone. See, DePaoli, et al. *Diabetes Care.* 2014 July; 37(7):1918-23. Thus, INT131 can administered to treat PSP while limiting side effects. Limiting side effects is advantageous as it helps preserve the quality of life for subject taking the medication and results in improved subject compliance with taking medication.

In particular, the invention provides a method of treating progressive supranuclear palsy or symptoms thereof in a subject in need thereof comprising administering to the subject a pharmaceutical composition comprising a therapeutically effective amount of a compound of formula (I),

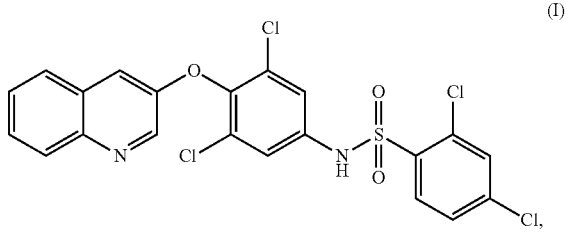 [SMILES: O=S(=O)(Nc1cc(Cl)c(Oc2cnc3ccccc3c2)c(Cl)c1)c1ccc(Cl)cc1Cl]

or a pharmaceutically acceptable salt, prodrug, or isomer thereof.

In one embodiment, the compound of formula (I) (i.e., INT131) is provided in the form of a besylate salt.

In one embodiment, the therapeutically effective amount is from about 0.1 to about 15 mg. In another embodiment, the therapeutically effective amount is from about 1 to about 10 mg. In still another embodiment, the therapeutically effective amount is from about 2 to about 6 mg. In yet another embodiment, the therapeutically effective amount is about 3 mg. In another embodiment, the therapeutically effective amount is about 15 mg, about 14 mg, about 13 mg, about 12 mg, about 11 mg, about 10 mg, about 9 mg, about 8 mg, about 7 mg, about 6 mg, about 5 mg, about 4 mg, about 3 mg, about 2 mg, or about 1 mg.

The pharmaceutical compositions used in the methods of the invention may be administered to the subject twice a day, daily, every other day, three times a week, twice a week, weekly, every other week, twice a month, or monthly.

Preferably, the methods of the invention result in increase of the adiponectin level in the subject by at least about 30%, at least about 68%, at least about 175%, or at least about 200%.

Provided herein are methods of treating a subject that include: selecting a subject having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein); and administering a pharmaceutical composition including a therapeutically effective amount of a compound of formula (I),

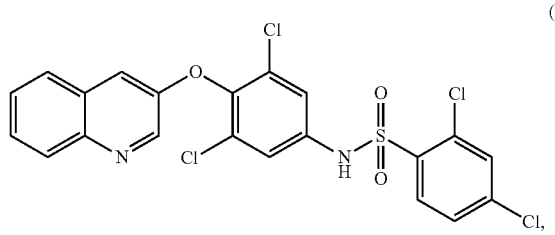

or a pharmaceutically acceptable salt, prodrug, or isomer thereof, to the selected subject.

Also provided herein are methods of selecting a treatment for a subject that include: identifying a subject having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein); and selecting a pharmaceutical composition including a therapeutically effective amount of a compound of formula (I), or a pharmaceutically acceptable salt, prodrug, or isomer thereof, for the identified subject. Some embodiments of any of the methods described herein further include administering the selected treatment to the identified subject.

Also provided herein are methods of selecting a subject for treatment that include: identifying a subject having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein); and selecting the identified subject for treatment with a pharmaceutical composition comprising a therapeutically effective amount of a compound of formula (I), or a pharmaceutically acceptable salt, prodrug, or isomer thereof.

Also provided herein are methods of selecting a subject for participation in a clinical trial that include: identifying a subject having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein); and selecting the identified subject for participation in a clinical trial that includes administration of a pharmaceutical composition including a therapeutically effective amount of a compound of formula (I), or a pharmaceutically acceptable salt, prodrug, or isomer thereof.

Also provided herein are methods of predicting the efficacy of a treatment in a subject that include: determining a level of neurofilament light chain protein level in a sample including cerebrospinal fluid, blood, serum, or plasma obtained from the subject; and determining that a treatment with a pharmaceutical composition including a therapeutically effective amount of a compound of formula (I), or a pharmaceutically acceptable salt, prodrug, or isomer thereof, is more likely to be effective in a subject having an elevated level of neurofilament light chain protein in the sample as compared to a reference level of neurofilament light chain protein (e.g., any of the exemplary reference levels of neurofilament light chain protein described herein), as compared to a subject not having an elevated level of neurofilament light chain protein in a sample including blood, serum, or plasma as compared to the reference level of neurofilament light chain protein.

In some embodiments of any of the methods described herein, the subject has not been diagnosed with a neurological disorder or neural tissue damage. In some embodiments of any of the methods described herein, the subject does not present with a symptom of a neurological disorder or neural tissue damage (e.g., any of the symptoms of a neurological disorder or neural tissue damage described herein or known in the art). In some embodiments of any of the methods described herein, the subject has been diagnosed as having a neurological disorder (e.g., any of the neurological disorders described herein or known in the art) or neural tissue damage. In some embodiments of any of the methods described herein, the subject has been diagnosed as having progressive supranuclear palsy. Some embodiments of any of the methods described herein further include performing an assay to determine the level of neurofilament light chain protein in the sample obtained from the subject (e.g., any of the exemplary assays for determining a level of neurofilament light chain protein described herein or known in the art). In some embodiments of any of the methods described herein, the assay is a single-molecule array assay.

In some embodiments of any of the methods described herein, the subject has been previously administered a different pharmaceutical composition and the different pharmaceutical composition was determined not to be therapeutically effective.

Also provided herein are methods of determining the efficacy of a treatment in a subject that include: determining a first level of neurofilament light chain protein level in a sample including cerebrospinal fluid, blood, serum, or plasma obtained from the subject at a first time point; determining a second level of neurofilament light chain protein level in a sample including cerebrospinal fluid, blood, serum, or plasma obtained from the subject at a second time point, where the subject received at least one dose of a pharmaceutical composition including a therapeutically effective amount of a compound of formula (I), or a pharmaceutically acceptable salt, prodrug, or isomer thereof, between the first and the second time points; and identifying the pharmaceutical composition as being effective in a subject having a reduced second level of neurofilament light chain protein as compared to the first level of neurofilament light chain protein.

In some embodiments of any of the methods described herein, the subject is a participant in a clinical trial. Some embodiments of any of the methods described herein, the method further includes administering one or more additional doses of the pharmaceutical composition identified as being effective in the subject.

Provided herein are methods of treating a subject that includes: selecting a subject having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and administering a pharmaceutical composition including a therapeutically effective amount of a compound of formula (I), or a pharmaceutically acceptable salt, prodrug, or isomer thereof, to the selected subject.

Also provided herein are methods of selecting a treatment for a subject that include: identifying a subject having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting a pharmaceutical composition including a therapeutically effective amount of a compound of formula (I), or a pharmaceutically acceptable salt, prodrug, or isomer thereof, for the identified subject. Some embodiments of any of the methods described herein further include administering the selected treatment to the identified subject.

Also provided herein are methods of selecting a subject for treatment that include: identifying a subject having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting the identified subject for treatment with a pharmaceutical composition including a therapeutically effective amount of a compound of formula (I), or a pharmaceutically acceptable salt, prodrug, or isomer thereof.

Also provided herein are methods of selecting a subject for participation in a clinical trial that include: identifying a subject having an elevated second level of neurofilament light chain protein in a sample providing cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting the identified subject for participation in a clinical trial that includes administration of a pharmaceutical composition including a therapeutically effective amount of a compound of formula (I), or a pharmaceutically acceptable salt, prodrug, or isomer thereof.

In some embodiments of any of the methods described herein, wherein the subject has not been diagnosed with a neurological disorder (e.g., any of the neurological disorders described herein or known in the art) or neural tissue damage. In some embodiments of any of the methods described herein, the subject does not present with a symptom of a neurological disorder or neural tissue damage (e.g., any of the symptoms of a neurological disorder or neural tissue damage described herein or known in the art). In some embodiments of any of the methods described herein, the subject has been diagnosed as having a neurological disorder (e.g., any of the neurological disorders described herein or known in the art) or neural tissue damage. In some embodiments of any of the methods described herein, the subject has been diagnosed as having progressive supranuclear palsy.

Some embodiments of any of the methods described herein that includes performing an assay to determine the first level and second levels of neurofilament light chain protein in the sample obtained from the subject at the first time point and the second time point, respectively (e.g., any of the assays for determining a level of neurofilament light chain protein described herein or known in the art). In some embodiments of any of the methods described herein, the assay is a single-molecule array assay.

In some embodiments of any of the methods described herein, the subject has been previously administered a different pharmaceutical composition and the different pharmaceutical composition was determined not to be therapeutically effective. In some embodiments of any of the methods described herein, the subject has not been diagnosed with a neurological disorder (e.g., any of the neurological disorders described herein or known in the art) or neural tissue damage. In some embodiments of any of the methods described herein, the subject does not present with a symptom of a neurological disorder or neural tissue damage (e.g., any of the symptoms of a neurological disorder or neural tissue damage described herein or known in the art).

DETAILED DESCRIPTION OF THE INVENTION

Figure 1:
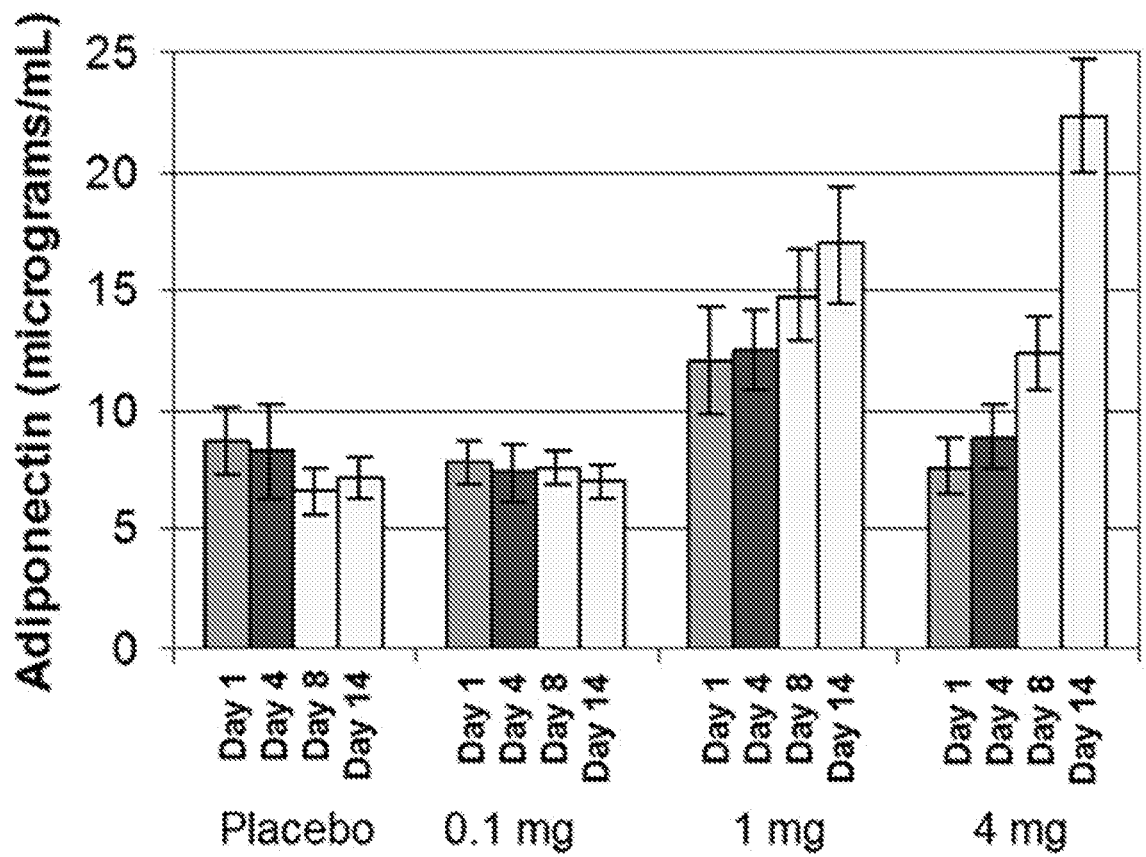
FIG. 1. Serum adiponectin levels at Day 1, 4, 8, and 14 following administration of a placebo or 0.1, 1.0 or 4.0 mg INT131.

In particular, the compound (I),

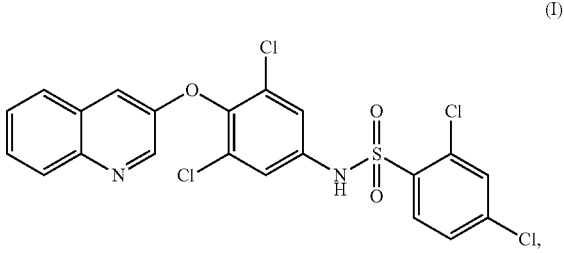 [SMILES: O=S(=O)(Nc1cc(Cl)c(Oc2cnc3ccccc3c2)c(Cl)c1)c1ccc(Cl)cc1Cl]

(I)

has been found to be unexpectedly effective for the treatment of progressive supranuclear palsy. This compound is also known as INT131 or CHS131.

Definitions

The terms "treat," "treating" and "treatment" refer to a method of alleviating or abrogating a disease and/or its attendant symptoms. In another embodiment, treating refers to impeding or halting progression of a disease. In yet another embodiment, treating refers to extending the life of a subject with a disease.

In some embodiments, treatment can result in a reduction (e.g., an about 1% to about 99% reduction, an about 1% to about 95% reduction, an about 1% to about 90% reduction, an about 1% to about 85% reduction, an about 1% to about 80% reduction, an about 1% to about 75% reduction, an about 1% to about 70% reduction, an about 1% to about 65% reduction, an about 1% to about 60% reduction, an about 1% to about 55% reduction, an about 1% to about 50% reduction, an about 1% to about 45% reduction, an about 1% to about 40% reduction, an about 1% to about 35% reduction, an about 1% to about 30% reduction, an about 1% to about 25% reduction, an about 1% to about 20% reduction, an about 1% to about 15% reduction, an about 1% to about 10% reduction, an about 1% to about 5% reduction, an about 5% to about 99% reduction, an about 5% to about 95% reduction, an about 5% to about 90% reduction, an about 5% to about 85% reduction, an about 5% to about 80% reduction, an about 5% to about 75% reduction, an about 5% to about 70% reduction, an about 5% to about 65% reduction, an about 5% to about 60% reduction, an about 5% to about 55% reduction, an about 5% to about 50% reduction, an about 5% to about 45% reduction, an about 5% to about 40% reduction, an about 5% to about 35% reduction, an about 5% to about 30% reduction, an about 5% to about 25% reduction, an about 5% to about 20% reduction, an about 5% to about 15% reduction, an about 5% to about 10% reduction, an about 10% to about 99% reduction, an about 10% to about 95% reduction, an about 10% to about 90% reduction, an about 10% to about 85% reduction, an about 10% to about 80% reduction, an about 10% to about 75% reduction, an about 10% to about 70% reduction, an about 10% to about 65% reduction, an about 10% to about 60% reduction, an about 10% to about 55% reduction, an about 10% to about 50% reduction, an about 10% to about 45% reduction, an about 10% to about 40% reduction, an about 10% to about 35% reduction, an about 10% to about 30% reduction, an about 10% to about 25% reduction, an about 10% to about 20% reduction, an about 10% to about 15% reduction, an about 15% to about 90% reduction, an about 15% to about 85% reduction, an about 15% to about 80% reduction, an about 15% to about 75% reduction, an about 15% to about 70% reduction, an about 15% to about 65% reduction, an about 15% to about 60% reduction, an about 15% to about 55% reduction, an about 15% to about 50% reduction, an about 15% to about 45% reduction, an about 15% to about 40% reduction, an about 15% to about 35% reduction, an about 15% to about 30% reduction, an about 15% to about 25% reduction, or an about 15% to about 20% reduction) in the number, severity, and/or duration of one or more (e.g., two, three, four, five, or six) symptoms and/or metrics (e.g., scores) of a neurological disorder (e.g., progressive supranuclear palsy) or neural tissue damage (e.g., any of the symptoms and/or metrics of any of the neurological disorders described herein or known in the art) (e.g., any of the symptoms and/or metrics of progressive supranuclear palsy described herein or known in the art).

The term "progressive supranuclear palsy" or "PSP" refers to a neurologic disorder of unknown origin that gradually destroys cells in many areas of the brain and the accumulation of abnormal aggregates of the microtubule-associated protein tau, resulting in insoluble paired helical filaments [Friedhoff, 2000 #12095], including the gradual deterioration of neurons and glial cells in the midbrain and frontal cortex that display insoluble helical filaments of tau proteins.

PSP starts with a pre-symptomatic phase during which there is an increase in neuropathological abnormalities. Next, patients develop isolated symptoms that are suggestive of PSP (soPSP). In any of the methods described herein, PSP can be classic PSP-Richardson's syndrome (PSP-RS), PSP-Parkinsonism (PSP-P), PSP-corticobasal syndrome (PSP-CBS), PSP-progressive non-fluent aphasia (PSP-PNFA), or PSP-pure akinesia with gait freezing (PSP-PAGF) (Ling et al., *J. Mov. Discord.* 9(1):3-13, 2016). In some embodiments of any of the methods described herein, a subject can be previously diagnosed or identified as having PSP (e.g., PSP-RS, PSP-P, PSP-PNFA, or PSP-PAGF). In some embodiments of any of the methods described herein, a subject can previously be identified as having an increased risk of developing PSP (e.g., a subject having a genetically-related family member (e.g., a parent, grandparent, aunt, uncle, or sibling) that has been identified or diagnosed as having PSP). In some embodiments of any of the methods described herein, a subject can previously be identified or diagnosed as having pre-symptomatic PSP or suggestive-of-PSP.

After onset, symptoms of PSP become rapidly and progressively worse. Subjects diagnosed with PSP may become severely disabled within five years and die within six years.

Symptoms of PSP usually first appear at the age of 60 and worsen until death. People with PSP commonly die from pneumonia, choking or other complications caused by the loss of functional brain cells, resulting in loss of autonomic and motor function (e.g. the ability to swallow).

Signs and symptoms of PSP include movement, cognitive and psychiatric disorders. Voluntary movement can be impaired in PSP and include pseudobulbar palsy (i.e. inability to control facial movements), bradykinesia (i.e. slow or abnormal muscle movement), neck and trunk rigidity, impaired gait, impaired balance, posture instability and difficulty with speech and swallowing. Individuals who become unable to swallow food can be fitted with a feeding tube to provide nutrition. A most obvious, outward sign of the disease is an inability to coordinate and move the eyes normally, resulting in a vertical gaze palsy. Cognitive impairments include loss of executive functions (e.g. attention control, inhibitory control, working memory, cognitive flexibility, reasoning, problem solving and planning) and diminished fluency. Associated psychiatric symptoms include depression, feelings of irritability, sadness or apathy, insomnia, fatigue and loss of energy.

In some embodiments, a subject can be identified as having PSP using the MDS PSP Diagnostic Criteria (as described in, e.g., Hoglinger et al., *Mov. Disord.* 31:644-652, 2016).

In some embodiments, a subject can be identified as being at increased risk of developing PSP or identified as having PSP (e.g., any of the types of PSP described herein), e.g., at least in part, by detecting a genetic alteration in a gene encoding the microtubule-associated protein tau (MAPT) (e.g., any of the inversion polymorphisms in the MAPT gene, any of the haplotype-specific polymorphisms in the MAPT gene, the rare-coding MAPT variant (A152T), or mutations that enhance splicing of exon 10 in the MAPT gene described, e.g., in Hoglinger et al., *Nature Genet.* 43:699-705, 2011, and Hinz et al., *Cold Spring Harb.*

*Perspect Biol.*). Non-limiting examples of genetic alterations in a gene encoding MAPT include mutations that result in the production of MAPT protein that include one or more point mutations of: S285R, L284R, P301L, and G303V. Additional specific genetic mutations in a gene encoding MAPT protein that can be used to identify a subject as having an increased risk of developing PSP or can be used to identify a subject as having PSP (e.g., any of the types of PSP described herein) are described in, e.g., Boxer et al., *Lancet* 16:552-563, 2017.

In some embodiments, a subject can be identified as having an increased risk of developing PSP or identified as having PSP (e.g., any of the types of PSP described herein), e.g., at least in part, by detecting tau protein deposits (e.g., 4-repeat tau protein deposits), detecting of atrophy of the midbrain and/or superior cerebellar peduncles (e.g., using any of the imaging techniques described herein or known in the art, e.g., magnetic resonance imaging (MM) or positron emission tomography (PET) scans), and/or detecting of hypometabolism in the frontal cortex, caudate, and/or thalamus in the subject (e.g., using any of the imaging techniques described herein or known in the art, e.g., MRI, CT scan, or PET scan).

For example, in some embodiments a subject can be identified or diagnosed as having PSP (e.g., any of the types of PSP described herein), e.g., at least in part, by using Mill to detect brain atrophy (Min et al., *Nat. Med.* 21:1154-1162, 2015; Yanamandra et al., *Ann. Clin. Transl. Neurol.* 2:278-288, 2015), changes in regional gray and white matter volume to detect atrophy (see, e.g., Josephs et al., *Brain* 137:2783-2795, 2014; Santos-Santos et al., *JAMA Neurol.* 73:733-742, 2016), and midbrain atrophy by detecting midbrain area and volume in the subject (Josephs et al., *Neurobiol. Aging* 29:280-289, 2008; Whitwell et al., *Eur. J. Neurol.* 20:1417-1422, 2013). In some embodiments, a subject can be identified or diagnosed as having PSP (e.g., any of the types of PSP described herein), e.g., at least in part, by administering to a subject a tau protein tracer (e.g., AV1451 or PBB3) and detecting tau protein in the subject's brain using a PET scan (see, e.g., Marquie et al., *Ann. Neurol.* 78:787-800, 2015; Cho et al., *Mov. Disord.* 32:134-140, 2017; Whitwell et al., *Mov. Disord.* 32:124-133, 2017; and Smith et al., *Mov. Disord.* 32:108-114, 2017). In some embodiments, a subject can be diagnosed or identified as having PSP (e.g., any of the types of PSP described herein), e.g., at least in part, by detecting the difference in binaural masking level in the subject using a PET scan (see, e.g., Hughes et al., *J. Neurophysiol.* 112:3086-3094, 2014).

In some embodiments, a subject can be identified as being at increased risk of developing PSP or identified as having PSP (e.g., any of the types of PSP described herein), e.g., at least in part, by detecting the presence of, or an elevated level (e.g., as compared to a level in a healthy control subject) of, one or more biomarkers in a subject. In some embodiments, a subject can be identified or diagnosed as having PSP (e.g., any of the types of PSP described herein), e.g., at least in part, by detecting the presence of, or detection of an elevated level (e.g., as compared to a level in a healthy control subject) of, neurofilament light chain in the blood and/or cerebrospinal fluid in a subject (e.g., using any of the immunoassays described in Scherling et al., *Ann. Neurol.* 75:116-126, 2014; Bacioglu et al., *Neuron* 91:56-66, 2016; and Rojas et al., *Ann. Clin. Transl. Neurol.* 3:216-255, 2016). In some embodiments, a subject can be identified or diagnosed as having PSP (e.g., any of the types of PSP described herein), e.g., at least in part, by detecting the presence of, or detection of an elevated level (e.g., as compared to a level in a healthy control subject) of, YKL-40 in cerebrospinal fluid from the subject (see, e.g., Magdalinou et al., *J. Neurol. Neurosurg. Psychiatry* 2014 October; 85(10): 1065-1075; and Magdalinou et al., *J. Neurol. Neurosurg. Psychiatry* 86:1240-1247, 2015).

In some embodiments, a subject can be identified or diagnosed as having PSP (e.g., any of the types of PSP described herein), e.g., at least in part, by detecting decreased saccade velocity and gain in the subject using infrared oculography (see, e.g., Boxer et al., *Arch. Neurol.* 69:509-517, 2012; Boxer et al., *Lancet Neurol.* 132:676-685, 2014). In some embodiments, a subject can be identified or diagnosed as having PSP (e.g., any of the types of PSP described herein), e.g., at least in part, by detecting a spontaneous and evoked blink rate associated with PSP in the subject (see, e.g., Bologna et al., *Brain* 132:502-510, 2009). In some embodiments, a subject can be identified or diagnosed as having PSP (e.g., any of the types of PSP described herein), e.g., at least in part, by detecting decreased retinal thickness in a subject's eye using optical coherence tomography (see, e.g., Schneider et al., *J. Neural Transm.* 121:41-47, 2014). In some embodiments, a subject can be identified or diagnosed as having PSP (e.g., any of the types of PSP described herein), e.g., at least in part, by detecting disrupted circadian rhythms and sleep in the subject (see, e.g., Walsh et al., *Sleep Med.* 22; 50-56, 2016).

In some embodiments, a subject can be identified or diagnosed as having PSP (e.g., any of the types of PSP described herein), e.g., at least in part, by detected a decreased ratio of 33 kDa tau to 55 kDa tau in the subject (e.g., as compared to the ratio of 33 kDa tau to 55 kDa tau in a healthy subject). In some embodiments, a subject can be identified or diagnosed as having PSP (e.g., any of the types of PSP described herein), e.g., at least in part, by detecting the presence of, or detecting an elevated level of, protein tyrosine phosphatase 1 (Ptpn1) (e.g., as described in Santiago et al., *Mov. Discord.* 29(4):550-555, 2014).

Some embodiments of any of the methods described herein can include monitoring the progression of PSP in the subject, e.g., by assessing the severity of PSP in the subject over time, e.g., using the Progressive Supranuclear Palsy Rating Scale (PSPRS) (e.g., as described in Golbe et al., *Brain* 130(6):1552-1565, 2007). The PSPRS evaluates subjects according to their ability to perform daily activities, behavior, bulbar function, ocular motor function, limb motor function, and gait.

In some embodiments of any of the methods described herein, a subject can be further administered levodopa and/or physical therapy (e.g., as described in Lamb et al., *Curr. Treat Options Neurol.* 14:42, 2016, and Clerici et al., *PLoS One* 12: e0170927, 2017).

The term "therapeutically effective amount" refers to that amount of the compound being administered sufficient to treat a disease. In one embodiment, the therapeutically effective amount is sufficient to prevent development of or alleviate to some extent one or more of the symptoms of the condition or disorder being treated.

The term "subject" is defined herein to include animals such as mammals, including but not limited to, primates (e.g., humans), cows, sheep, goats, horses, dogs, cats, rabbits, rats, mice and the like. In preferred embodiments, the subject is a human.

In some embodiments of any of the methods described herein, a subject may be referred to as a patient. In some embodiments of any of the methods described herein, the subject is 40 years old or older (e.g., 41 years old or older, 42 years old or older, 43 years old or older, 44 years old or older, 45 years old or older, 50 years old or older, 55 years old or older, 60 years old or older, 65 years old or older, 70 years old or older, 75 years old or older, 80 years old or older, 90 years old or older, or 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, or 103 years old).

In some embodiments, the subject does not present with a symptom (e.g., any of the symptoms described herein or known in the art) of a neurological disorder or neural tissue damage (e.g., progressive supranuclear palsy, multiple sclerosis, relapsing-remitting MS (RRMS), clinically isolated syndrome (CIS), primary progressive MS (PPMS), secondary progressive MS (SPMS), or radiologically isolated syndrome (RIS)). In other embodiments, the subject has been diagnosed as having a neurological disorder (e.g., multiple sclerosis, relapsing-remitting MS (RRMS), clinically isolated syndrome (CIS), primary progressive MS (PPMS), secondary progressive MS (SPMS), or radiologically isolated syndrome (RIS)) or neural tissue damage. In other embodiments, the subject has been diagnosed as having neural tissue damage (e.g., severe traumatic brain injury, sports-related mild traumatic brain injury, or post-concussion syndrome). In yet other embodiments, the subject has not been diagnosed as having a neurological disorder or neural tissue damage.

In some embodiments, the subject has a degenerative and traumatic neurological disorder (e.g., dementia, amyotrophic lateral sclerosis, or spinal cord injury).

In yet other embodiments, the subject has been diagnosed or identified as having a neurological disorder that would benefit from treatment with a proliferator-activated receptor gamma (PPARγ) agonist (e.g., CHS-131).

In some embodiments, the subject has previously been administered at least one dose of a CHS-131. In some embodiments, the subject is a participant in a clinical trial.

In other embodiments, the subject has been previously administered a different pharmaceutical composition and the different pharmaceutical composition was determined not to be therapeutically effective.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either net or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either net or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isbutyric, oxalic, maleic, malonic, benzoic, succinic, suberic, fumeric mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science,* 1977, 66, 1-19). Certain specific compounds of the present inventions contain both basic and acidic functionalities that allow the compounds to be converted into either base or acid addition salts.

The neutral forms of the compounds may be registered by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In additional to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, the term "biological sample" or "sample" refers to a sample obtained or derived from a subject. By way of example, the sample can include cerebrospinal fluid (CSF), blood, serum, or plasma. In some embodiments, a sample can be, or include, a blood sample. In some embodiments, a sample can be, or include, a serum sample. In some embodiments, a sample can be, or include, a plasma sample.

As used herein, "obtain" or "obtaining" can be any means whereby one comes into possession of the sample by "direct" or "indirect" means. Directly obtaining a sample means performing a process (e.g., performing a physical method such as extraction or phlebotomy) to obtain a sample from the subject. Indirectly obtaining a sample refers to receiving the sample from another party or source (e.g., a third-party laboratory that directly acquired the sample). Thus, obtain is used to mean collection and/or removal of the sample from the subject. Some embodiments of any of them methods described herein can include obtaining a sample or samples from a subject.

The phrase "an elevated" or "an increased level" can be an elevation or an increase of at least 1% (e.g., at least 2%, at least 4%, at least 6%, at least 8%, at least 10%, at least 12%, at least 14%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least 100%, at least 110%, at least 115%, at least 120%, at least 140%, at least 150%, at least 200%, at least 250%, at least 300%, at least 350%, at least 400%, or between 1% and 400%, between 1% and 300%, between 1% and 200%, between 1% and 100%, between 1% and 50%, between 1% and 25%, between 1% and 10%, between 10% and 400%, between 10% and 300%, between 10% and 200%, between 10% and 100%, between 10% and 50%, between 50% and 400%, between 50% and 300%, between 50% and 200%, between 50% and 100%, between 50% and 75%, between 75% and 100%, or 1%, 2%, 4%, 5%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 250%, 300%, 350%, or 400%), e.g., as compared to a reference level (e.g., any of the exemplary reference levels described herein) or a first level of neurofilament light chain protein.

In some embodiments, an elevated level can be an elevation or an increase of about 1% to about 500%, about 1% to about 450%, about 1% to about 400%, about 1% to about 350%, about 1% to about 300%, about 1% to about 250%, about 1% to about 200%, about 1% to about 150%, about 1% to about 100%, about 1% to about 50%, about 1% to about 25%, about 1% to about 20%, about 1% to about 15%, about 1% to about 10%, about 1% to about 5%, about 2% to about 500%, about 2% to about 450%, about 2% to about 400%, about 2% to about 350%, about 2% to about 300%, about 2% to about 250%, about 2% to about 200%, about 2% to about 150%, about 2% to about 100%, about 2% to about 50%, about 2% to about 25%, about 2% to about 20%, about 2% to about 15%, about 2% to about 10%, about 5% to about 500%, about 5% to about 450%, about 5% to about 400%, about 5% to about 350%, about 5% to about 300%, about 5% to about 250%, about 5% to about 200%, about 5% to about 150%, about 5% to about 100%, about 5% to about 50%, about 5% to about 25%, about 5% to about 20%, about 5% to about 15%, about 5% to about 10%, about 10% to about 500%, about 10% to about 450%, about 10% to about 400%, about 10% to about 350%, about 10% to about 300%, about 10% to about 250%, about 10% to about 200%, about 10% to about 150%, about 10% to about 100%, about 10% to about 50%, about 10% to about 25%, about 10% to about 20%, about 10% to about 15%, about 15% to about 500%, about 15% to about 450%, about 15% to about 400%, about 15% to about 350%, about 15% to about 300%, about 15% to about 250%, about 15% to about 200%, about 15% to about 150%, about 15% to about 100%, about 15% to about 50%, about 15% to about 25%, about 15% to about 20%, about 20% to about 500%, about 20% to about 450%, about 20% to about 400%, about 20% to about 350%, about 20% to about 300%, about 20% to about 250%, about 20% to about 200%, about 20% to about 150%, about 20% to about 100%, about 20% to about 50%, about 20% to about 25%, about 25% to about 500%, about 25% to about 450%, about 25% to about 400%, about 25% to about 350%, about 25% to about 300%, about 25% to about 250%, about 25% to about 200%, about 25% to about 150%, about 25% to about 100%, about 25% to about 50%, about 50% to about 500%, about 50% to about 450%, about 50% to about 400%, about 50% to about 350%, about 50% to about 300%, about 50% to about 250%, about 50% to about 200%, about 50% to about 150%, about 50% to about 100%, about 100% to about 500%, about 100% to about 450%, about 100% to about 400%, about 100% to about 350%, about 100% to about 300%, about 100% to about 250%, about 100% to about 200%, about 100% to about 150%, about 150% to about 500%, about 150% to about 450%, about 150% to about 400%, about 150% to about 350%, about 150% to about 300%, about 150% to about 250%, about 150% to about 200%, about 200% to about 500%, about 200% to about 450%, about 200% to about 400%, about 200% to about 350%, about 200% to about 300%, about 200% to about 250%, about 250% to about 500%, about 250% to about 450%, about 250% to about 400%, about 250% to about 350%, about 250% to about 300%, about 300% to about 500%, about 300% to about 450%, about 300% to about 400%, about 300% to about 350%, about 350% to about 500%, about 350% to about 450%, about 350% to about 400%, about 400% to about 500%, about 400% to about 450%, or about 450% to about 500%, e.g., as compared to a reference level (e.g., any of the exemplary reference levels described herein) or a first level of neurofilament light chain protein.

A "reduced level" can be a 1% to about 99% reduction, a 1% to about 95% reduction, a 1% to about 90% reduction, a 1% to about 85% reduction, a 1% to about 80% reduction, a 1% to about 75% reduction, a 1% to about 70% reduction, a 1% to about 65% reduction, a 1% to about 60% reduction, a 1% to about 55% reduction, a 1% to about 50% reduction, a 1% to about 45% reduction, a 1% to about 40% reduction, a 1% to about 35% reduction, a 1% to about 30% reduction, a 1% to about 25% reduction, a 1% to about 20% reduction, a 1% to about 15% reduction, a 1% to about 10% reduction, a 1% to about 5% reduction, an about 5% to about 99% reduction, an about 5% to about 95% reduction, an about 5% to about 90% reduction, an about 5% to about 85% reduction, an about 5% to about 80% reduction, an about 5% to about 75% reduction, an about 5% to about 70% reduction, an about 5% to about 65% reduction, an about 5% to about 60% reduction, an about 5% to about 55% reduction, an about 5% to about 50% reduction, an about 5% to about 45% reduction, an about 5% to about 40% reduction, an about 5% to about 35% reduction, an about 5% to about 30% reduction, an about 5% to about 25% reduction, an about 5% to about 20% reduction, an about 5% to about 15% reduction, an about 5% to about 10% reduction, an about 10% to about 99% reduction, an about 10% to about 95% reduction, an about 10% to about 90% reduction, an about 10% to about 85% reduction, an about 10% to about 80% reduction, an about 10% to about 75% reduction, an about 10% to about 70% reduction, an about 10% to about 65% reduction, an about 10% to about 60% reduction, an about 10% to about 55% reduction, an about 10% to about 50% reduction, an about 10% to about 45% reduction, an about 10% to about 40% reduction, an about 10% to about 35% reduction, an about 10% to about 30% reduction, an about 10% to about 25% reduction, an about 10% to about 20% reduction, an about 10% to about 15% reduction, an about 15% to about 99% reduction, an about 15% to about 95% reduction, an about 15% to about 90% reduction, an about 15% to about 85% reduction, an about 15% to about 80% reduction, an about 15% to about 75% reduction, an about 15% to about 70% reduction, an about 15% to about 65% reduction, an about 15% to about 60% reduction, an about 15% to about 55% reduction, an about 15% to about 50% reduction, an about 15% to about 45% reduction, an about 15% to about 40% reduction, an about 15% to about 35% reduction, an about 15% to about 30% reduction, an about 15% to about 25% reduction, an about 15% to about 20% reduction, an about 20% to about 99% reduction, an about 20% to about 95% reduction, an about 20% to about 90% reduction, an about 20% to about 85% reduction, an about 20% to about 80% reduction, an about 20% to about 75% reduction, an about 20% to about 70% reduction, an about 20% to about 65% reduction, an about 20% to about 60% reduction, an about 20% to about 55% reduction, an about 20% to about 50% reduction, an about 20% to about 45% reduction, an about 20% to about 40% reduction, an about 20% to about 35% reduction, an about 20% to about 30% reduction, an about 20% to about 25% reduction, an about 25% to about 99% reduction, an about 25% to about 95% reduction, an about 25% to about 90% reduction, an about 25% to about 85% reduction, an about 25% to about 80% reduction, an about 25% to about 75% reduction, an about 25% to about 70% reduction, an about 25% to about 65% reduction, an about 25% to about 60% reduction, an about 25% to about 55% reduction, an about 25% to about 50% reduction, an about 25% to about 45% reduction, an about 25% to about 40% reduction, an about 25% to about 35% reduction, an about 25% to about 30% reduction, an about 30% to about 99% reduction, an about 30% to about 95% reduction, an about 30% to about 90% reduction, an about 30% to about 85% reduction, an about 30% to about 80% reduction, an about 30% to about 75% reduction, an about 30% to about 70% reduction, an about 30% to about 65% reduction, an about 30% to about 60% reduction, an about 30% to about 55% reduction, an about 30% to about 50% reduction, an about 30% to about 45% reduction, an about 30% to about 40% reduction, an about 30% to about 35% reduction, an about 35% to about 99% reduction, an about 35% to about 95% reduction, an about 35% to about 90% reduction, an about 35% to about 85% reduction, an about 35% to about 80% reduction, an about 35% to about 75% reduction, an about 35% to about 70% reduction, an about 35% to about 65% reduction, an about 35% to about 60% reduction, an about 35% to about 55% reduction, an about 35% to about 50% reduction, an about 35% to about 45% reduction, an about 35% to about 40% reduction, an about 40% to about 99% reduction, an about 40% to about 95% reduction, an about 40% to about 90% reduction, an about 40% to about 85% reduction, an about 40% to about 80% reduction, an about 40% to about 75% reduction, an about 40% to about 70% reduction, an about 40% to about 65% reduction, an about 40% to about 60% reduction, an about 40% to about 55% reduction, an about 40% to about 50% reduction, an about 40% to about 45% reduction, an about 45% to about 99% reduction, an about 45% to about 95% reduction, an about 45% to about 90% reduction, an about 45% to about 85% reduction, an about 45% to about 80% reduction, an about 45% to about 75% reduction, an about 45% to about 70% reduction, an about 45% to about 65% reduction, an about 45% to about 60% reduction, an about 45% to about 55% reduction, an about 45% to about 50% reduction, an about 50% to about 99% reduction, an about 50% to about 95% reduction, an about 50% to about 90% reduction, an about 50% to about 85% reduction, an about 50% to about 80% reduction, an about 50% to about 75% reduction, an about 50% to about 70% reduction, an about 50% to about 65% reduction, an about 50% to about 60% reduction, an about 50% to about 55% reduction, an about 55% to about 99% reduction, an about 55% to about 95% reduction, an about 55% to about 90% reduction, an about 55% to about 85% reduction, an about 55% to about 80% reduction, an about 55% to about 75% reduction, an about 55% to about 70% reduction, an about 55% to about 65% reduction, an about 55% to about 60% reduction, an about 60% to about 99% reduction, an about 60% to about 95% reduction, an about 60% to about 90% reduction, an about 60% to about 85% reduction, an about 60% to about 80% reduction, an about 60% to about 75% reduction, an about 60% to about 70% reduction, an about 60% to about 65% reduction, an about 65% to about 99% reduction, an about 65% to about 95% reduction, an about 65% to about 90% reduction, an about 65% to about 85% reduction, an about 65% to about 80% reduction, an about 65% to about 75% reduction, an about 65% to about 70% reduction, an about 70% to about 99% reduction, an about 70% to about 95% reduction, an about 70% to about 90% reduction, an about 70% to about 85% reduction, an about 70% to about 80% reduction, an about 70% to about 75% reduction, an about 75% to about 99% reduction, an about 75% to about 95% reduction, an about 75% to about 90% reduction, an about 75% to about 85% reduction, an about 75% to about 80% reduction, an about 80% to about 99% reduction, an about 80% to about 95% reduction, an about 80% to about 90% reduction, an about 80% to about 85% reduction, an about 85% to about 99% reduction, an about 85% to about 95% reduction, an about 85% to about 90% reduction, an about 90% to about 99% reduction, an about 90% to about 95% reduction, or an about 95% to about 99% reduction, e.g., in a second level of neurofilament light chain protein as compared to a first level of neurofilament light chain protein.

As used herein a "first time point" can, e.g., refer to an initial time point wherein the subject has not yet received a dose of a pharmaceutical composition (e.g., any of the pharmaceutical compositions described herein). In some embodiments, a first time point can be, e.g., a time point when a subject has been diagnosed with a neurological disorder or neural tissue damage prior to receiving any treatment (e.g., any of the exemplary treatments described herein). In other examples, a first time point can be a time point when a subject has developed at least one (e.g., 1, 2, 3, 4, 5, 6, 7, 8, 9 or 10) symptom(s) associated with a neurological disorder or neural tissue damage (e.g., any of the exemplary symptoms of a neurological disorder or neural tissue damage described herein or known in the art) and has not received any treatment. In some embodiments, a first time point can represent a time point after which a subject has previously received a different pharmaceutical treatment and the different pharmaceutical treatment was deemed not be successful.

As used herein a "second time point" can, e.g., refer to a second time point after the first time point. In some embodiments, a subject can receive or has received at least one (e.g., 1, 2, 3, 4, 5, 6, 7, 8, 9 or 10) dose of a pharmaceutical composition (e.g., any of the pharmaceutical compositions) between the first and the second time points. In some embodiments, the time difference between a first and second time point can be, e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 151 days, 152 days, 153 days, 154 days, 155 days, 156 days, 157 days, 158 days, 159 days, 160 days, 161 days, 162 days, 163 days, 164 days, 165 days, 166 days, 167 days, 168 days, 169 days, 170 days, 171 days, 172 days, 173 days, 174 days, 175 days, 176 days, 177 days, 178 days, 179 days, 180 days, 7 months, 8 months 9 months, 10 months, 11 months, or 1 year.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Embodiments of the Invention

A new use of a known compound that modulates PPARγ has now been discovered. Specifically, it has been discovered that PPARγ agonists, and in particular, INT131, are effective to treat progressive supranuclear palsy.

Thus, in one embodiment, the present invention is directed to a method of treating progressive supranuclear palsy or its symptoms in a subject in need thereof comprising administering to the subject a pharmaceutical composition comprising a therapeutically effective amount of INT131 or a pharmaceutically acceptable salt, prodrug, or isomer thereof.

Without wishing to be limited to a particular theory, it is believed that INT131 increases PPARγ activation in brain cells (including activation of elements in the PPARγ pathway), increases adiponectin levels, improves energy metabolism in brain cells, and reduces or prevents aggregation of abnormal Tau proteins by reducing oxidative stress and neuroinflammation, and therefore, treats progressive supranuclear palsy.

Adiponectin affects glucose and lipid metabolism, insulin sensitivity, and inflammation. Yamauchi T, et al., Adiponectin stimulates glucose utilization and fatty-acid oxidation by activating AMP-activated protein kinase. *Nat Med.* 2002; 8:1288-1295; Berg A H, et al., The adipocyte-secreted protein Acrp30 enhances hepatic insulin action. *Nat Med.* 2001; 7:947-953; and Yamauchi T, et al., Targeted disruption of AdipoR1 and AdipoR2 causes abrogation of adiponectin binding and metabolic actions. *Nat Med.* 2007; 13:332-339. Additionally, adiponectin targets the central nervous system and it also modulates appetite and energy homeostasis. Moreover, adiponectin stimulates food intake. Kubota N, et al., Adiponectin stimulates AMP-activated protein kinase in the hypothalamus and increases food intake. *Cell Metab.* 2007; 6:55-68. Since subjects with progressive supranuclear palsy suffer weight loss, administration of INT131 to increase adiponectin and stimulate food intake treats subjects with progressive supranuclear palsy.

PSP has been associated with increased oxidative stress and neuroinflammation. Specifically, malondialdehyde, a biomarker for oxidative stress, has been demonstrated to be elevated in neurons in areas of the brain affected by PSP, but not in unaffected areas. Albers DS, et al., Frontal lobe dysfunction in progressive supranuclear palsy: evidence for oxidative stress and mitochondrial impairment, *J Neurochem.* 2000 February; 74(2):878-81. Further, the cortex of PSP patients show a 39% decrease in ketoglutarate dehydrodenase/glutamate dehydrogenase ratio, which is indicative of oxidative stress to those areas. Albers, et al. 2000. Finally, patients affected with PSP demonstrate abnormal lipid peroxidation and protein peroxidation, hallmarks of oxidative stress. Odetti P, et al., Lipoperoxidation is selectively involved in progressive supranuclear palsy, *J Neuropathol Exp Neurol.* 2000 May; 59(5):393-7.

Activated microglia and astrocytes, which are associated with neuroinflammation, have been found in affected areas of the brain in PSP patients. Ferrer I, et al., Phosphorylated map kinase (ERK1, ERK2) expression is associated with early tau deposition in neurons and glial cells, but not with increased nuclear DNA vulnerability and cell death, in Alzheimer disease, Pick's disease, progressive supranuclear palsy and corticobasal degeneration, *Brain Pathol.* 2001 April; 11(2):144-58. Recent studies have shown a region-specific upregulation of IL-1β in the substantia nigra of PSP patients, as compared to either Parkinson's disease or Alzheimer's Disease brains. Moreover, Further other markers of neuroinflammation, including TNFα, and IL-6 have been found to be elevated in affected areas of the brain in PSP patients, whereas the anti-inflammatory cytokines TGFβ and IL-10 are not elevated. Fernandez-Botran R, et al., Cytokine expression and microglial activation in progressive supranuclear palsy, *Parkinsonism Relat Disord.* 2011 November; 17(9):683-8.

PPARγ agonists, including INT131, have been shown to inhibit both oxidative stress and neuroinflammation in animal models and humans. Specifically, this inhibition has been demonstrated for: pioglitazone and rosiglitazone for ischemic stroke with reperfusion, Collino M, et al., Modulation of the oxidative stress and inflammatory response by PPAR-gamma agonists in the hippocampus of rats exposed to cerebral ischemia/reperfusion, *Eur J Pharmacol.* 2006 Jan. 13; 530 (1-2): 70-80; pioglitazone and rosiglitazone for traumatic brain injury, Kapadia R, et al., Mechanisms of anti-inflammatory and neuroprotective actions of PPAR-gamma agonists, *Front Biosci.* 2008 Jan. 1; 13:1813-26; INT131 for type-2 diabetes mellitus, Lee, D H, et al., Selective PPARγ modulator INT131 normalizes insulin signaling defects and improves bone mass in diet-induced obese mice. *Am J Physiol Endocrinol Metab.* 2012; 302: 552-560; and INT131 for multiple sclerosis, US Patent Application Publication 2014/0213612.

Notably, there are disadvantages to treating humans with rosiglitazone and pioglitazone. Avandia (rosiglitazone) is only approved for treating patients with type 2 diabetes and increases the risk of: heart failure, cardiovascular events in individuals with heart failure, edema, weight gain, macular edema, bone fractures, decreases in hemoglobin and hemocrit, and other adverse events. Moreover, Avandia does not cross the blood-brain-barrier. Avanida package insert, September 2016. Since only 9-14% of rosiglitazone crosses the blood brain barrier, it may have limited efficacy or require more frequent and higher doses to adequately treat neurological disorders such as progressive supranuclear palsy. Like Avandia, Actos (pioglitazone) is only approved for treating patients with type 2 diabetes. Actos also caries several serious warnings and precautions including: increased risk of fluid retention leading to congestive heart failure, hypoglycemia, sometimes fatal hepatic failure, bladder cancer, edema, bone fractures, macular edema, and other adverse events. Actos package insert, December 2016. Notably, unlike the two commercially available PPAR-γ ligands, rosiglitazone and pioglitazone, INT131 readily crosses the blood brain barrier.

Despite data for full PPARγ agonists decreasing oxidative stress and neuroinflammation, the benefits of INT131 is surprising since it was unknown if the selective PPARγ pathway activation of INT131 would treat PSP.

Accordingly, it is surprising and unexpected that INT131 treats progressive supranuclear palsy.

In one embodiment, INT131 reduces the signs and symptoms of progressive supranuclear palsy. INT131 reduces one or more sign or symptom of progressive supranuclear palsy. In a further embodiment, the reduction of the signs and symptoms of progressive supranuclear palsy is reduction in the number of the signs and symptoms of progressive supranuclear palsy. In yet a further embodiment, the reduction of the signs and symptoms of progressive supranuclear palsy is reduction in the severity or degree of at least one sign or symptom of progressive supranuclear palsy. In still a further embodiment, the reduction of the signs and symptoms of progressive supranuclear palsy is reduction in the duration of at least one sign or symptom of progressive supranuclear palsy.

In another embodiment, the onset of a sign or symptom of progressive supranuclear palsy is prevented or delayed in a subject with progressive supranuclear palsy upon administration of INT131 to the subject with progressive supranuclear palsy In one embodiment, INT131 reduces neural inflammation in a subject with progressive supranuclear palsy.

In one embodiment, INT131 is neuroprotective in a subject with progressive supranuclear palsy. In another embodiment, INT131 treats neuronal degeneration. In another embodiment, INT131 reduces atrophy or degeneration of the brain in subjects with progressive supranuclear palsy. In a further embodiment, INT131 reduces atrophy or degradation of the substantial nigra, globus palladus, subthalamic nucleus and or cerebellum.

In one embodiment, INT131 reduces or prevents weight loss in a subject with progressive supranuclear palsy. In another embodiment, INT131 increases appetite in a subject with progressive supranuclear palsy.

In another embodiment, INT131 treats metabolic dysfunction in a subject with progressive supranuclear palsy. In yet a further embodiment, INT131 increases adiponectin levels in a subject with progressive supranuclear palsy. In another embodiment, INT131 improves or increases glucose metabolism in a subject with progressive supranuclear palsy. In another embodiment, INT131 reduces hyperglycemia in a subject with progressive supranuclear palsy.

In another embodiment, INT131 improves mitochondrial function. In a further embodiment, INT131 improves mitochondrial calcium handling, and mitochondrial trafficking. In yet a further embodiment, INT131 increases the expression of peroxisome proliferator-activated receptor gamma coactivator 1-alpha (PGC-1a) and mitochondrial biogenesis. This results in improved behavior, improved survival (i.e. lifespan) and reduced brain degeneration in a subject with progressive supranuclear palsy.

In another embodiment, INT131 reduces the aggregation of abnormal Tau protein, or fragments of Tau protein, in a subject with progressive supranuclear palsy. In a further embodiment, INT131 ameliorates the reduction of neuroprotective proteins in the brain. In yet a further embodiment, INT131 reduces the reduction of brain-derived neurotrophic factor and Bcl 2.

In another embodiment, a period of time during which the therapeutic effects of INT131 are observed in a subject with progressive supranuclear palsy comprises 1 week, 2 weeks, 3 weeks, 4 weeks, 1 month, 2 months, 3 months, 4 months, 5 months, 6 months, 7 months, 8 months, 9 months, 10 months, 11 months, 1 year, 1.25 years, 1.5 years, 1.75 years, 2 years, 2.25 years, 2.5 years, 2.75 years, 3 years, 3.5 years, 4 years, 4.5 years, and 5 years.

In one embodiment, INT131 is in the form of a besylate salt.

In another embodiment, the therapeutically effective amount is from about 0.1 to about 10 milligrams. In another embodiment, the therapeutically effective amount is from about 1 to about 4 milligrams. In another embodiment, the therapeutically effective amount is from about 2 to about 3 milligrams.

In another embodiment, a composition comprising a therapeutically effective amount of INT131 is administered to a subject in need thereof at an interval that includes, but is not limited to, twice a day, daily, every other day, three times a week, twice a week, weekly, every other week, twice a month, monthly, and every other month.

In another embodiment, a composition comprising a therapeutically effective amount of INT131 is administered orally to a subject. In yet another embodiment, the composition is substantially the same as those disclosed in US Patent Application Publication 2013-0243865, the disclosure of which is expressly incorporated herein by reference.

In one embodiment, INT-131 is as effective, or more effective, treating progressive supranuclear palsy than other therapies. These therapies include therapies approved for treating progressive supranuclear palsy and those in development for treating progressive supranuclear palsy. These therapies include, but are not limited to, medications to treat movement disorders, medications to treat psychiatric disorders, psychotherapy, speech therapy, physical therapy, and occupational therapy.

Medications to treat movement disorders include, but are not limited to, tetrabenazine, antipsychotic drugs, such as haloperidol, chlorpromazine, risperidone, and quetiapine, and other medications such as amantadine, levetiracetam, and, clonazepam.

Medications to treat psychiatric disorders include, but are not limited to, antidepressants such as citalopram, fluoxetine, and sertraline, antipsychotic drugs such as quetiapine, risperidone, and olanzapine, and mood-stabilizing drugs, including anticonvulsants, such as valproate, carbamazepine, and lamotrigine.

Psychotherapy includes, but is not limited to, talk therapy to help a subject manage behavioral problems, depression, and suicidal thoughts.

Speech therapy includes, but is not limited to, improving a subjects ability to speak clearly, and improve function and control of muscles used for eating and swallowing.

Physical therapy includes, but is not limited to, enhancing strength, flexibility, balance and coordination, reducing the risk of falls, and improve posture to lessen the severity of movement problems.

Occupational therapy includes, but is not limited to, use of assistive devices that improve functional abilities such as handrails, and eating and drinking utensils for subjects with diminished motor skills.

In another embodiment, INT-131 is administered to a subject in need thereof in combination with one or more therapies listed herein.

Also provided herein are methods of treating a subject that include: selecting a subject identified or diagnosed as having PSP (e.g., any of the types of PSP described herein) (e.g., using any of the techniques for identifying or diagnosing PSP described herein) and administering a therapeutically effective dose of a compound of formula (I), or a pharmaceutically acceptable salt, prodrug, or isomer thereof, to the selected subject. In some embodiments of these methods, the subject identified or diagnosed as having PSP did not benefit from a previously administered (different) therapeutic treatment for PSP.

Also provided herein are methods of treating a subject that include: selecting a subject identified as having an increased risk of developing PSP (e.g., any of the types of PSP described herein) (e.g., using any of the techniques for identifying a subject having an increased risk of developing PSP described herein) and administering a therapeutically effective dose of a compound of formula (I), or a pharmaceutically acceptable salt, prodrug, or isomer thereof, to the selected subject.

Also provided herein are methods of treating a subject that include: diagnosing or identifying a subject as having PSP (e.g., any of the types of PSP described herein) or having an increased risk of developing PSP (e.g., any of the types of PSP described herein) (e.g., by performing any of the techniques for diagnosing or identifying a subject as having PSP described herein or known in the art, or by performing any of the techniques for identifying a subject as having an increased risk of developing PSP described herein or known in the art), and administering a therapeutically effective dose of a compound of formula (I), or a pharmaceutically acceptable salt, prodrug, or isomer thereof, to the diagnosed or identified subject.

In some embodiments of any of the methods of treatment described herein, the method can result in a decreased risk of developing comorbidity in the subject (e.g., as compared to the risk of developing comorbidity in a similar subject having a similar neurological disorder (e.g., PSP), but administered a different treatment). Some embodiments of any of the methods described herein can further include administering to the subject an agent that alleviates a negative side effect of a compound of formula (I), or a pharmaceutically acceptable salt, prodrug, or isomer thereof, in the subject (e.g., weight loss or mood swings).

In some embodiments of any of the methods of treatment described herein, the method can result in increasing the life span of the subject (e.g., as compared to a similar subject having a similar neurological disorder (e.g., PSP), but receiving a different treatment). In some embodiments of any of the methods of treatment described herein, the method results in an improvement in the motor function of the subject (e.g., as compared to the motor function of the subject prior to treatment).

Some embodiments of any of the methods of treatment described herein further can include administering to the subject an agent for treating depression, obsessive-compulsive behavior, and/or apathy. Some embodiments of any of the methods described herein can further include administering to the subject an agent that alleviates eye irritation and/or eye closure symptoms. Some embodiments of any of the methods described herein can further include administering to the subject a treatment for reducing weight loss or a treatment for reducing the risk of developing aspiration pneumonia.

Also provided are methods of reducing the rate of progression of PSP in a subject (e.g., as compared to a similar subject having a similar stage of PSP but administered a different treatment) that include: identifying a subject having an early stage of PSP (e.g., pre-symptomatic PSP or suggestive-of-PSP) (e.g., by performing any of the techniques for determining the stage of PSP described herein); and administering a therapeutically effective dose of a compound of formula (I), or a pharmaceutically acceptable salt, prodrug, or isomer thereof, to the identified subject.

Also provided are methods of reducing the rate or progression of PSP in a subject (e.g., as compared to a similar subject having a similar stage of PSP but administered a different treatment) that include administering a therapeutically effective dose of a compound of formula (I), or a pharmaceutically acceptable salt, prodrug, or isomer thereof, to a subject identified or diagnosed as having an early state of PSP (e.g., pre-symptomatic PSP or suggestive-of-PSP) (e.g., using any of the techniques described herein).

Also provided herein are methods of selecting a treatment for a subject that include: selecting a subject identified or diagnosed as having PSP (e.g., any of the types of PSP described herein) (e.g., using any of the techniques for identifying or diagnosing PSP in a subject described herein), and selecting a therapeutically effective dose of a compound of formula (I), or a pharmaceutically acceptable salt, prodrug, or isomer thereof, for the selected subject.

Also provided herein are methods of selecting a subject for treatment with a compound of formula (I), or a pharmaceutically acceptable salt, prodrug, or isomer thereof, that include: selecting a subject identified as having an increased risk of developing PSP (e.g., any of the types of PSP described herein) (e.g., using any of the techniques for identifying a subject as having an increased risk of developing PSP described herein or known in the art); and selecting the selected subject for treatment with a therapeutically effective dose of a compound of formula (I), or a pharmaceutically acceptable salt, prodrug, or isomer thereof.

Also provided herein are methods of determining the efficacy of treatment in a subject having PSP that include: (a) determining a first level of one or more biomarkers (e.g., by performing an immunoassay) in a sample obtained from the subject at a first time point; (b) administering a therapeutically effective amount of a compound of formula (I), or a pharmaceutically acceptable salt, prodrug, or isomer thereof to the subject after the first time point; and (c) determining a second level of the one or more biomarkers (e.g., by performing an immunoassay) in a sample obtained from the subject at a second time point, where the second time point occurs after the first time point and after step (b), wherein the administered compound of formula (I), or a pharmaceutically acceptable salt, prodrug, or isomer thereof, is identified as being effective if the second level is about the same, is decreased as compared to the first level, or is within +/−20% (e.g., within +/−15%, within +/−10%, or within +/−5%) of the first level. In some embodiments, the methods for determining the efficacy of treatment in a subject having PSP include: (a) determining a first level of neuro-filament light chain (e.g., by performing an immunoassay) in a sample comprising blood or cerebrospinal fluid obtained from the subject at a first time point; (b) administering a therapeutically effective amount of a compound of formula (I), or a pharmaceutically acceptable salt, prodrug, or isomer thereof to the subject after the first time point; and (c) determining a second level of neuro-filament light chain (e.g., by performing an immunoassay) in a sample comprising blood or cerebrospinal fluid obtained from the subject at a second time point, where the second time point occurs after the first time point and after step (b), wherein the administered compound of formula (I), or a pharmaceutically acceptable salt, prodrug, or isomer thereof, is identified as being effective if the second level is about the same, is decreased as compared to the first level, or is within +/−20% (e.g., within +/−15%, within +/−10%, or within +/−5%) of the first level.

Also provided herein are methods of monitoring a subject having PSP receiving a treatment including a compound of formula (I), or a pharmaceutically acceptable salt, prodrug, or isomer thereof, that include: determining two or more levels of a biomarker (e.g., by performing an immunoassay) on different samples comprising blood or cerebrospinal fluid obtained from a subject having PSP (e.g., any of the types of PSP described herein) at different time points. In some embodiments, the biomarker is neurofilament light chain. Some embodiments of these methods can further include performing MRI, CT scan, or PET scan on the subject's brain.

In some embodiments, methods of determining the efficacy of treatment or the methods of monitoring a subject can further include assessing the severity, duration, and/or frequency of one or more additional symptoms of PSP in the subject (e.g., any of the symptoms of PSP described herein using any of the exemplary techniques or metrics described herein).

Some embodiments of any of the methods described herein can further include administering physical therapy, speech and language therapy, occupational therapy, and/or an antidepressant to the subject, Also provided herein are methods of treating a subject that include selecting a subject (e.g., any of the subjects described herein) having an elevated level of neurofilament light chain protein in a sample including cerebrospinal fluid, blood, serum, or plasma obtained from the subject, as compared to a reference level of neurofilament light chain protein (e.g., any of the reference levels of neurofilament light chain protein described herein); and administering a pharmaceutical composition including a therapeutically effective amount of a compound of formula (I), or a pharmaceutically acceptable salt, prodrug, or isomer thereof (e.g., using any of the doses or frequencies of administration described herein), to the selected subject.

Also provided are methods of selecting a treatment for a subject (e.g., any of the subjects described herein) that include identifying a subject having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein); and selecting a pharmaceutical composition including a therapeutically effective amount of a compound of formula (I), or a pharmaceutically acceptable salt, prodrug, or isomer thereof, for the identified subject.

Provided herein are methods of selecting a subject for treatment that include: identifying a subject (e.g., any of the subjects described herein) having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein); and selecting the identified subject for treatment with a pharmaceutical composition including a therapeutically effective amount of a compound of formula (I), or a pharmaceutically acceptable salt, prodrug, or isomer thereof.

Provided herein are methods of selecting a subject for participation in a clinical trial that include: identifying a subject (e.g., any of the subjects described herein) having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein); and selecting the identified subject for participation in a clinical trial that includes administration of a pharmaceutical composition comprising a therapeutically effective amount of a compound of formula (I), or a pharmaceutically acceptable salt, prodrug, or isomer thereof.

Provided herein are methods of predicting the efficacy of a treatment in a subject (e.g., any of the subjects described herein) that include: determining a level of neurofilament light chain protein level in a sample including cerebrospinal fluid, blood, serum, or plasma obtained from the subject; and determining that a treatment with a pharmaceutical composition including a therapeutically effective amount of a compound of formula (I), or a pharmaceutically acceptable salt, prodrug, or isomer thereof, is more likely to be effective in a subject having an elevated level of neurofilament light chain protein in the sample as compared to a reference level of neurofilament light chain protein (e.g., any of the exemplary reference levels of neurofilament light chain protein described herein), as compared to a subject not having an elevated level of neurofilament light chain protein in a sample including blood, serum, or plasma as compared to the reference level of neurofilament light chain protein.

Provided herein are methods of determining the efficacy of a treatment in a subject (e.g., any of the subjects described herein) that include: determining a first level of neurofilament light chain protein level in a sample including cerebrospinal fluid, blood, serum, or plasma obtained from the subject at a first time point; determining a second level of neurofilament light chain protein level in a sample including cerebrospinal fluid, blood, serum, or plasma obtained from the subject at a second time point, where the subject received at least one (e.g., at least two, at least three, at least four, at least five, at least six, at least seven, at least eight, at least nine, or at least ten) dose of a pharmaceutical composition including a therapeutically effective amount of a compound of formula (I), or a pharmaceutically acceptable salt, prodrug, or isomer thereof, between the first and the second time points; and identifying the pharmaceutical composition as being effective in a subject having a reduced second level of neurofilament light chain protein as compared to the first level of neurofilament light chain protein.

Provided herein are methods of treating a subject that includes: selecting a subject (e.g., any of the subjects described herein) having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and administering a pharmaceutical composition including a therapeutically effective amount of a compound of formula (I), or a pharmaceutically acceptable salt, prodrug, or isomer thereof, to the selected subject.

Provided herein are methods of selecting a treatment for a subject that include identifying a subject (e.g., any of the subjects described herein) having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting a pharmaceutical composition including a therapeutically effective amount of a compound of formula (I), or a pharmaceutically acceptable salt, prodrug, or isomer thereof, for the identified subject.

Also provided herein are methods of selecting a subject for treatment that include: identifying a subject (e.g., any of the subjects described herein) having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting the identified subject for treatment with a pharmaceutical composition including a therapeutically effective amount of a compound of formula (I), or a pharmaceutically acceptable salt, prodrug, or isomer thereof.

Also provided herein are methods of selecting a subject for participation in a clinical trial that include: identifying a subject (e.g., any of the subjects described herein) having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting the identified subject for participation in a clinical trial that includes administration of a pharmaceutical composition including a therapeutically effective amount of a compound of formula (I), or a pharmaceutically acceptable salt, prodrug, or isomer thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the invention will be apparent from the detailed description and figures, and from the claims.

Neurofilament Light Chain Protein and Methods of Detecting Neurofilament Light Chain Protein Neurofilaments are type IV intermediate filaments and heteropolymers. Neurofilaments are expressed in the brain and are unique to neuronal cells. Neurofilaments in the central nervous system include neurofilament heavy chain (NFH), neurofilament medium chain (NFM), neurofilament light chain (NFL), and α-internexin. Neurofilaments in the peripheral nervous system comprise NFH, NFM, NFL, and peripherin. Neurofilaments are vital for the maintenance of axon caliber, axon radial growth, and the intracellular transport of electrical impulses along axons (Eyer and Peterson, *Neuron* 12: 389-405, 1994; Ohara et al., *J. Cell Biol.* 121: 387-395, 1993; Zhu et al., *Exp. Neurol.* 148: 299-316, 1997).

Mutations in the NFL gene have been shown to cause Charcot-Marie Tooth disease, demyelinating type 1F (CMT1F), and Charcot-Marie Tooth disease, axonal type 2E (CMT2). Mutations in the NFL gene affect the assembly of neurofilaments in neurons (Sasaki et al., *Hum. Mol. Genet.* 15: 943-952, 2006; and Yates et al., *Eur. J. Cell Biol.* 88: 193-202, 2009).

Together with the medium and heavy subunits, neurofilament light chain represents one of the scaffolding proteins of the neuronal cytoskeleton (Teunissen et al., *Mult. Scler.* 18(5):552-556, 2012) and is released in the extracellular space following axonal damage.

The cDNA sequence and protein sequence of human neurofilament light chain is provided in SEQ ID NO: 1 and SEQ ID NO: 2, respectively. The cDNA sequence and protein sequence of mouse neurofilament light chain is provided in SEQ ID NO: 3 and SEQ ID NO: 4, respectively.

```
Human neurofilament light chain cDNA sequence
                                                          (SEQ ID NO: 1)
ATGAGTTCCTTCAGCT ACGAGCCGTA CTACTCGACC TCCTACAAGC GGCGCTACGT

GGAGACGCCCCGGGTGCACA TCTCCAGCGT GCGCAGCGGC TACAGCACCG

CACGCTCAGC TTACTCCAGCTACTCGGCGC CGGTGTCTTC CTCGCTGTCC

GTGCGCCGCA GCTACTCCTC CAGCTCTGGATCGTTGATGC CCAGTCTGGA

GAACCTCGAC CTGAGCCAGG TAGCCGCCAT CAGCAACGACCTCAAGTCCA

TCCGCACGCA GGAGAAGGCG CAGCTCCAGG ACCTCAATGA CCGCTTCGCC
```

-continued

```
AGCTTCATCG AGCGCGTGCA CGAGCTGGAG CAGCAGAACA AGGTCCTGGA

AGCCGAGCTG CTGGTGCTGC GCCAGAAGCA CTCCGAGCCA TCCCGCTTCC

GGGCGCTGTA CGAGCAGGAGATCCGCGACC TGC GCCTGGC GGCGGAAGAT

GCCACCAACG AGAAGCAGGC GCTCCAGGGCGAGCGCGAAG GGCTGGAGGA

GACCCTGCGC AACCTGCAGG CGCGCTATGA AGAGGAGGTGCTGAGCCGCG

AGGACGCCGA GGGCCGGCTG ATGGAAGCGC GCAAAGGCGC CGACGAGGCG

GCGCTCGCTC GCGCCGAGCT CGAGAAGCGC ATCGACAGCT TGATGGACGA

AATCTCTTTTCTGAAGAAAG TGCACGAAGA GGAGATCGCC GAACTGCAGG

CGCAGATCCA GTACGCGCAGATCTCCGTGG AGATGGACGT GACCAAGCCC

GACCTTTCCG CCGCGCTCAA GGACATCCGCGCGCAGTACG AGAAGCTGGC

CGCCAAGAAC ATGCAGAACG CTGAGGAATG GTTCAAGAGCCGCTTCACCG

TGCTGACCGA GAGCGCCGCC AAGAACACCG ACGCCGTGCG CGCCGCCAAG

GACGAGGTGT CCGAGAGCCG TCGTCTGCTC AAGGCCAAGA CCCTGGAAAT

CGAAGCATGCCGGGGCATGA ATGAAGCGCT GGAGAAGCAG CTGCAGGAGC

TGGAGGACAA GCAGAACGCCGACATCAGCG CTATGCAGGA CACGATCAAC

AAATTAGAAA ATGAATTGAG GACCACAAAGAGTGAAATGG CACGATACCT

AAAAGAATAC CAAGACCTCC TCAACGTGAA GATGGCTTTGGATATTGAGA

TTGCAGCTTA CAGGAAACTC TTGGAAGGCG AGGAGACCCG ACTCAGTTTC

ACCAGCGTGG GAAGCATAAC CAGTGGCTAC TCCCAGAGCT CCCAGGTCTT

TGGCCGATCTGCCTACGGCG GTTTACAGAC CAGCTCCTAT CTGATGTCCA

CCCGCTCCTT CCCGTCCTACTACACCAGCC ATGTCCAAGA GGAGCAGATC

GAAGTGGAGG AAACCATTGA GGCTGCCAAGGCTGAGGAAG CCAAGGATGA

GCCCCCCTCT GAAGGAGAAG CCGAGGAGGA GGAGAAGGACAAGGAAGAGG

CCGAGGAAGA GGAGGCAGCT GAAGAGGAAG AAGCTGCCAA GGAAGAGTCT

GAAGAAGCAA AGAAGAAGAA AGAAGGAGGT GAAGGTGAAG AAGGAGAGGA

AACCAAGAAGCTGAAGAGG AGGAGAAGAA AGTTGAAGGT GCTGGGGAGG

AACAAGCAGC TAAGAAGAAAGATTGA
```

Human neurofilament light chain amino acid sequence
(SEQ ID NO: 2)
MSSFSYEPYYSTSYKRRYVETPRVHISSVRSGYSTARSAYSSYSAPVSSSLSVRRSYSSSS

GSLMPSLENLDLSQVAAISNDLKSIRTQEKAQLQDLNDRFASFIERVHELEQQNKVLEAE

LLVLRQKHSEPSRFRALYEQEIRDLRLAAEDATNEKQALQGEREGLEETLRNLQARYEE

EVLSREDAEGRLMEARKGADEAALARAELEKRIDSLMDEISFLKKVHEEEIAELQAQIQ

YAQISVEMDVTKPDLSAALKDIRAQYEKLAAKNMQNAEEWFKSRFTVLTESAAKNTDA

VRAAKDEVSESRRLLKAKTLEIEACRGMNEALEKQLQELEDKQNADISAMQDTINKLEN

ELRTTKSEMARYLKEYQDLLNVKMALDIEIAAYRKLLEGEETRLSFTSVGSITSGYSQSS

QVFGRSAYGGLQTSSYLMSTRSFPSYYTSHVQEEQIEVEETIEAAKAEEEAKDEPPSEGEA

EEEEKDKEEAEEEEAAEEEEAAKEESEEAKEEEEGGEGEEGEETKEAEEEEKKVEGAGE

EQAAKKKD

Mouse neurofilament light chain cDNA sequence
(SEQ ID NO: 3)
ATGAGTTCGTTCGGCTACGATCCGTACTTTTCGACCTCCTACAAGCGGCGCTATGTG

GAGACGCCCCGGGTGCACATCTCCAGCGTGCGCAGCGGCTACAGCACGGCGCGCTC

-continued

```
CGCGTACTCCAGCTACTCCGCGCCGGTCTCCTCCTCGCTGTCCGTGCGCCGCAGCTA

CTCGTCCAGCTCTGGCTCTTTGATGCCCAGCCTGGAGAATCTCGATCTGAGCCAGGT

AGCCGCCATCAGCAACGACCTCAAGTCTATCCGCACACAAGAGAAGGCACAGCTGC

AGGACCTCAACGATCGCTTCGCCAGCTTCATCGAGCGCGTGCACGAGCTGGAGCAG

CAGAACAAGGTCCTGGAAGCCGAGCTGTTGGTGCTGCGCCAGAAACACTCTGAGCC

TTCCCGCTTCCGCGCCCTGTACGAGCAGGAGATCCGCGATCTGCGGCTGGCAGCGGA

AGACGCCACTAACGAGAAGCAGGCGCTGCAGGGCGAGCGCGAGGGGCTGGAGGAG

ACTCTGCGCAACCTGCAGGCTCGCTATGAGGAAGAAGTGCTGAGCCGCGAGGACGC

CGAGGGCCGGCTGATGGAAGCGCGCAAAGGTGCGGATGAGGCCGCGCTCGCCCGCG

CCGAGCTGGAGAAGCGCATCGACAGCCTGATGGACGAGATAGCTTTCCTGAAGAAG

GTGCACGAGGAAGAGATCGCCGAGCTGCAGGCTCAGATCCAGTATGCTCAGATCTC

CGTGGAGATGGACGTGTCCTCCAAGCCCGACCTCTCCGCCGCTCTCAAGGACATCCG

CGCTCAGTACGAGAAGCTGGCCGCCAAGAACATGCAGAACGCCGAAGAGTGGTTCA

AGAGCCGCTTCACCGTGCTAACCGAGAGCGCCGCCAAGAACACCGACGCTGTGCGC

GCTGCCAAGGACGAGGTGTCGGAAAGCCGCCGCCTGCTCAAGGCTAAGACCCTGGA

GATCGAAGCCTGCCGGGGTATGAACGAAGCTCTGGAGAAGCAGCTGCAGGAGCTAG

AGGACAAGCAGAATGCAGACATTAGCGCCATGCAGGACACAATCAACAAACTGGA

GAATGAGCTGAGAAGCACGAAGAGCGAGATGGCCAGGTACCTGAAGGAGTACCAG

GACCTCCTCAATGTCAAGATGGCCTTGGACATCGAGATTGCAGCTTACAGAAAACTC

TTGGAAGGCGAAGAGACCAGGCTCAGTTTCACCAGCGTGGGTAGCATAACCAGCGG

CTACTCTCAGAGCTCGCAGGTCTTCGGCCGTTCTGCTTACAGTGGCTTGCAGAGCAG

CTCCTACTTGATGTCTGCTCGCTCTTTCCCAGCCTACTATACCAGCCACGTCCAGGAA

GAGCAGACAGAGGTCGAGGAGACCATTGAGGCTACGAAAGCTGAGGAGGCCAAGG

ATGAGCCCCCCTCTGAAGGAGAAGCAGAAGAGGAGGAGAAGGAGAAAGAGGAGGG

AGAGGAAGAGGAAGGCGCTGAGGAGGAAGAAGCTGCCAAGGATGAGTCTGAAGAC

ACAAAAGAAGAAGAAGAAGGTGGTGAGGGTGAGGAGGAAGACACCAAAGAATCTG

AAGAGGAAGAGAAGAAAGAGGAGAGTGCTGGAGAGGAGCAGGTGGCTAAGAAGA

AAGATTGA
```

Mouse neurofilament light chain amino acid sequence
(SEQ ID NO: 4)

```
MSSFGYDPYFSTSYKRRYVETPRVHISSVRSGYSTARSAYSSYSAPVSSSLSVRRSYSSSS

GSLMPSLENLDLSQVAAISNDLKSIRTQEKAQLQDLNDRFASFIERVHELEQQNKVLEAE

LLVLRQKHSEPSRFRALYEQEIRDLRLAAEDATNEKQALQGEREGLEETLRNLQARYEE

EVLSREDAEGRLMEARKGADEAALARAELEKRIDSLMDEIAFLKKVHEEEIAELQAQIQ

YAQISVEMDVSSKPDLSAALKDIRAQYEKLAAKNMQNAEEWFKSRFTVLTESAAKNTD

AVRAAKDEVSESRRLLKAKTLEIEACRGMNEALEKQLQELEDKQNADISAMQDTINKLE

NELRSTKSEMARYLKEYQDLLNVKMALDIEIAAYRKLLEGEETRLSFTSVGSITSGYSQS

SQVFGRSAYSGLQSSSYLMSARSFPAYYTSHVQEEQTEVEETIEATKAEEAKDEPPSEGE

AEEEEKEKEEGEEEEGAEEEEAAKDESEDTKEEEGGEGEEEDTKESEEEEKKEESAGEE

QVAKKKD
```

Some embodiments of any of the methods described herein can include a step of performing an assay to determine a level or levels (e.g., first and second level) of neurofilament light chain protein in a sample or samples (e.g., samples obtained from the subject at a first and a second time point). Non-limiting assays that may be used to detect a level or levels of neurofilament light chain are described herein. Additional assays that may be used to detect a level or levels of neurofilament light chain are known in the art.

A commercially-available enzyme-linked immunosorbent assay (UmanDiagnostics) can be used to measure a level or levels of neurofilament light chain protein in a sample or samples including cerebrospinal fluid, blood, serum, or plasma from a subject. An electrochemiluminescence (ECL)-based assay can also be used to detect a level or levels of neurofilament light chain. See, e.g., Lycke et al., *J. Neurol. Neurosurg. Psychiatry* 64(3):402-404, 1998; Teunissen et al., *Neurology* 72(15):1322-1329, 2009; Disanto et al., *J. Neurol. Neurosurg. Psychiatry* 87(2):126-129, 2015; and Kuhle et al., *Mult. Scler.* 22(12): 1550-1559, 2016). Another assay that can be performed to detect a level or levels of neurofilament light chain protein is a single-molecule array (Simoa) assay, which is described in detail in Kuhle et al., *Clin. Chem. Lab Med.* 54(10): 1655-166, 2016; and Gisslen et al., *EBioMedicine* 3:135-140, 2016). A Simoa assay for neurofilament light chain is commercially available from Quanterix (NF-LIGHT®). The NF-LIGHT® Quanterix Simoa assay has been used to detect levels of neurofilament light chain protein in samples including cerebrospinal fluid, blood, serum, or plasma from human subjects. The antibodies used in the NF-LIGHT® Quanteriz Simoa assay (obtained from Uman Diagnostics, Umea, Sweden) show cross-reactivity with human, mouse, bovine, and macaque neurofilament light chain proteins. The NF-LIGHT® Quanterix Simoa assay is a digital immunoassay.

Additional non-limiting assays that can be used to detect a level of neurofilament light chain protein in a sample include: enzyme-linked immunosorbent assay (ELISA), sensitive sandwich ELISA assay, electrochemiluminescence (ECL)-based assay, mass spectrometry (MS), western blotting, fluorescence-activated cell sorting (FACS), immunohistochemistry.

Other assays that can be used to detect a level or levels of neurofilament light chain in a sample obtained from a subject (e.g., any of the exemplary samples described herein) include immunoassays (e.g., enzyme-linked immunosorbent assays, sandwich enzyme-linked immunosorbent assays, and immunoprecipitation) and proteomic techniques.

Detecting Neurofilament Light Chain Protein

Assay for Detecting Neurofilament Light Chain (NFL) in Serum, Plasma, or Blood Samples Single-molecule array (Simoa) assay is a highly sensitive assay that allows accurate quantification of low neurofilament light chain concentrations (Disanto et al., *Ann. Neurol.* 81(6):857-870, 2017; Rohrer et al., *Neurology* 87(13):1329-1336, 2016; and Novakova et al., *Neurology* 89(22): 2230-2237, 2017).

Capture monoclonal antibody (mAB) 47: 3 is buffer exchanged and diluted to 0.3 mg/mL $4 \times 10^6$ paramagnetic beads (Quanterix Corporation) are buffer exchanged and activated using 0.5 mg/mL 1-ethyl-3-(3-dimetylaminopropyl) carbodiimide (Quanterix), followed by a 30-minute incubation at room temperature (HulaMixer, Thermo Fischer Scientific). The diluted capture mAB 47:3 is conjugated with the washed and activated paramagnetic beads for a 2-hour incubation at room temperature on a mixer. After the incubation, the beads are washed three times using a magnetic separator and blocked. Next, the conjugated beads are suspended and stored at 4° C.

The Simoa assay is run on a Simoa HD-1 instrument (Quanterix) using a two-step Assay Neat 20 protocol. Briefly, 100 µL of calibrator/sample in Tris-buffered saline (TBS), 0.1% Tween 20, 1% milk powder, 400 m/mL Heteroblock (Omega Biologicals), 25 µL conjugated beads in TBS, 0.1% Tween 20, 1% milk powder, 300 m/mL Heteroblock, and 20 µL of mAB 2:1 (0.1 m/mL in TBS, 0.1% Tween 20, 1% milk powder, 300 m/mL Heteroblock) are incubated for 35 minutes 15 seconds (47 cadences with 1 cadence is 45 seconds). Next, the mixture is washed. Then, 100 µL of streptavidin-conjugated 0-galactosidase (150 pM; Quanterix) is added, followed by a 5 minutes 15 second (7-cadence) incubation and wash. The mixture will then be placed on a Simoa HD-1 instrument. Prior to reading, 25 µL Resorufin β-D-galactopyranoside (Quanterix) is added. The calibrator curve is constructed using the standard from the NFL ELISA (NF-light, UmanDiagnostics). Samples and calibrators are measured in duplicates.

NFL levels are log-transformed to meet the normal assumption. The distribution of sNfl in healthy control is modeled by means of Generalized Additive Models for Location, Scale, and Shape (GAMLSS) using a Box-Cox t distribution according to Rigby and Stasinopoulous, Stat Med 23: 3053-3076, 2004, and cubic splines and percentile curves are obtained.

To quantify, intra- and interassay variability, bootstrapping is applied by drawing 100 random samples from the healthy controls.

Linear regression models are used to investigate the associations with log sNFL. Linear generalized estimating equation (GEE) models are similarly used to investigate associations with log sNFL.

Blood NFL Measurements by Ultrasensitive Simoa Assay

Serum Nfl levels are investigated in longitudinal blood samples.

A commercially available ELISA (UmanDiagnostics NF-light® assay) uses two highly specific, non-competing monoclonal antibodies (47:3 and 2:1) to quantify soluble NFL in cerebrospinal fluid (CSF) samples. Using this assay to analyze CSF samples, it was found that NFL is more sensitive than NFH to distinguish patients in different stages of MS versus controls (Kuhle et al., Mutt Scler 19:1597-1603, 2013). Together with UmanDiagnostics a highly sensitive electrochemiluminescence (ECL)-based NfL assay was developed suitable for the quantification of NFL in serum at concentrations relevant to clinical settings (Gaiottino et al., *PLoS One* 2013; 8(9): e75091, 2013; and Disanto et al., J Neurol Neurosurg Psychiatry 87(2): 126-129, 2015). The HD-1 analyzer relies on single-molecule arrays (Simoa) and the simultaneous counting of singulated capture microbeads (Rissin et al., Nat Biotechnol 28:595-599, 2010). The instrument integrates established paramagnetic microbead-based reagent robotics with a novel imaging module that digitizes the immunoassay with an array consumable and optical system at a cost similar to that of conventional immunoassay platforms (Wilson et al., *J Lab Autom* 21(4): 533-547, 2015). The system can accommodate user-developed custom reagents and assay protocols, as well as a menu of pre-validated assay kits. Across a range of immunoassays covering several disease areas, the fully automated Simoa assays exhibited ≥4 logs of measurement range, single digit CVs, and sensitivities in the femtogram per milliliter range (Wilson et al., *J Lab Autom* 21(4): 533-547, 2015). Thus, the Simoa HD-1 Analyzer is approximately 3 logs more sensitive than conventional fluorescence, chemiluminescence, and ECL immunoassay instrumentation.

Reference Levels

In some embodiments of any of the methods described herein, the reference level can be a level of neurofilament light chain protein detected in a similar sample obtained from a subject (e.g., a subject who is between 18 to 70 years of age), that has not been diagnosed or identified as having a neurological disorder (e.g. MS) or neural tissue damage, and does not have a family history of a neurological disorder (e.g., MS) or neural tissue damage. In some embodiments, a reference level can be threshold level of neurofilament light chain protein.

A reference level of neurofilament light chain protein (e.g., for samples including serum) is about 10 pg/mL to about 35 pg/mL (e.g., about 10 pg/mL to about 30 pg/mL, about 10 pg/mL to about 25 pg/mL, about 10 pg/mL to about 20 pg/mL, 10 pg/mL to about 15 pg/mL, 15 pg/mL to about 35 pg/mL about 15 pg/mL to about 30 pg/mL, about 15 pg/mL to about 25 pg/mL, about 15 pg/mL to about 20 pg/mL, about 20 pg/mL to about 35 pg/mL, about 20 pg/mL to about 30 pg/mL, about 20 pg/mL to about 25 pg/mL, about 25 pg/mL to about 35 pg/mL, or about 25 pg/mL or about 30 pg/mL).

In some embodiments, a reference level of neurofilament light chain protein can be a percentile value (e.g., mean value, 99% percentile, 95% percentile, 90% percentile, 85% percentile, 80% percentile, 75% percentile, 70% percentile, 65% percentile, 60% percentile, 55% percentile, or 50% percentile) of the levels of neurofilament light chain protein detected in similar samples in a population of healthy subjects (e.g., subjects that are not diagnosed or identified as having a disease (e.g., any of the neurological disorders described herein or neural tissue damage), do not present with a symptom of a disorder or disease (e.g., a neurological disease or disorder), and are not considered to have an elevated risk of developing a neurological disease or disorder).

In some embodiments, a reference level can be the level of neurofilament light chain detected in a similar sample obtained from the subject at an earlier time point.

CHS-131 (INT-131)

CHS-131 is an exemplary compound of formula (I).

In one aspect, CHS-131 reduces neural inflammation in a subject having been diagnosed as having a neurological disorder (e.g., multiple sclerosis (MS), relapsing-remitting MS (RRMS), or Alzheimer's disease) or neural tissue damage, or a subject that does not present with a symptom of a neurological disorder (e.g., multiple sclerosis (MS), relapsing-remitting MS (RRMS), or Alzheimer's disease) or neural tissue damage. In some embodiments, a subject can be identified or diagnosed as having an early stage of a neurological disorder or an early stage or mild neural tissue damage.

In some embodiments, administration of CHS-131 reduces atrophy or degeneration of the brain in the subject (e.g., any of the subjects described herein). In some embodiments, administration of CHS-131 reduces atrophy or degradation of the substantia nigra, globus palladus, subthalamic nucleus and/or cerebellum in the subject (e.g., any of the subjects described herein). In some embodiments, administration of CHS-131 reduces cortical atrophy in the brain of the subject (e.g., any of the subjects described herein).

In one aspect, administration of CHS-131 decreases the risk of developing a comorbidity (e.g., cardiovascular disease, type 2 diabetes mellitus) in the subject (e.g., any of the subjects described herein).

In one embodiment, CHS-131 is as effective, or more effective, treating a neurological disorder or neural tissue damage than other therapies. These therapies include therapies approved for treating a neurological disorder or neural tissue damage (e.g., any of the neurological disorders described herein) and those in development for treating a neurological disorder or neural tissue damage (e.g., any of the neurological disorder described herein).

In some embodiments of any of the methods described herein, a pharmaceutical composition including a therapeutically effective amount of formula (I), or a pharmaceutically acceptable salt, prodrug, or isomer thereof, can be co-administered to the subject with one or more additional treatments (e.g., any of the other exemplary treatments or therapies described herein).

Additional Methods of Treating

Provided herein are methods of treating a subject that include: selecting a subject (e.g., any of the exemplary subjects described herein) having an elevated level of neurofilament light chain protein in a sample including cerebrospinal fluid, blood, serum, or plasma obtained from the subject, as compared to a reference level of neurofilament light chain protein (e.g., any of the exemplary reference levels of neurofilament light chain protein described herein or known in the art); and administering a pharmaceutical composition including a therapeutically effective amount of a compound of formula (I), or a pharmaceutically acceptable salt, prodrug, or isomer thereof, to the selected subject (e.g., e.g., CHS-131) using any of the doses or frequencies of administration described herein).

Also provided are methods of treating a subject (e.g., any of the subjects described herein) that include: selecting a subject having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and administering a pharmaceutical composition including a therapeutically effective amount of a compound of formula (I), or a pharmaceutically acceptable salt, prodrug, or isomer thereof, to the selected subject (e.g., CHS-131, e.g., using any of the doses or frequencies of administration described herein).

Methods of Selecting a Treatment for a Subject

Provided herein are methods of selecting a treatment for a subject (e.g., any of the subjects described herein) that include: identifying a subject having an elevated level of neurofilament light chain protein in a sample comprising cerebrospinal fluid, blood, serum, or plasma obtained from the subject, as compared to a reference level of neurofilament light chain protein (e.g., any of the exemplary reference levels of neurofilament light chain protein described herein); and selecting a pharmaceutical composition including a therapeutically effective amount of a compound of formula (I), or a pharmaceutically acceptable salt, prodrug, or isomer thereof, for the identified subject.

Also provided are methods of selecting a treatment for a subject (e.g., any of the subjects described herein) that include: identifying a subject having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting a pharmaceutical composition including a therapeutically effective amount of a compound of formula (I), or a pharmaceutically acceptable salt, prodrug, or isomer thereof, for the identified subject. In any of the methods that include detecting a level of neurofilament light chain protein in a first and a second sample, one skilled in the art will appreciate that, e.g., the samples should be similar (e.g., both samples are serum samples, both samples are blood samples, both samples are plasma samples, or both samples are cerebrospinal fluid samples).

Some embodiments of these methods further include administering one or more doses (e.g., at least two, at least five, or at least ten doses) of the selected pharmaceutical composition to the identified subject. Some embodiments of these methods further include recording the selected pharmaceutical composition in the identified subject's clinical records.

Also provided herein are methods of selecting a subject for treatment that include: identifying a subject having an elevated level of neurofilament light chain protein in a sample comprising cerebrospinal fluid, blood, serum, or plasma obtained from the subject, as compared to a reference level of neurofilament light chain protein; and selecting the identified subject for treatment with a pharmaceutical composition comprising a therapeutically effective amount of a compound of formula (I), or a pharmaceutically acceptable salt, prodrug, or isomer thereof.

Also provided are methods of selecting a subject (e.g., any of the subjects described herein) for treatment that include: identifying a subject having an elevated second level of neurofilament light chain protein in a sample including cerebrospinal fluid, blood, serum, or plasma obtained from the subject at a second time point, as compared to a first level of neurofilament light chain protein in a sample including cerebrospinal fluid, blood, serum, or plasma obtained from the subject at a first time point; and selecting the identified subject for treatment with a pharmaceutical composition including a therapeutically effective amount of a compound of formula (I), or a pharmaceutically acceptable salt, prodrug, or isomer thereof.

Also provided herein are methods of selecting a subject (e.g., any of the subjects described herein) for participation in a clinical trial that include: identifying a subject having an elevated level of neurofilament light chain protein in a sample comprising cerebrospinal fluid, blood, serum, or plasma obtained from the subject, as compared to a reference level of neurofilament light chain protein (e.g., any of the exemplary reference levels of neurofilament light chain protein described herein); and selecting the identified subject for participation in a clinical trial that comprises administration of a pharmaceutical composition comprising a therapeutically effective amount of a compound of formula (I), or a pharmaceutically acceptable salt, prodrug, or isomer thereof (e.g., CHS-131, e.g., using any of the doses or frequencies of administration described herein).

Also provided are methods of selecting a subject for participation in a clinical trial that include: identifying a subject (e.g., any of the subjects described herein) having an elevated second level of neurofilament light chain protein in a sample including cerebrospinal fluid, blood, serum, or plasma obtained from the subject at a second time point, as compared to a first level of neurofilament light chain protein in a sample comprising cerebrospinal fluid, blood, serum, or plasma obtained from the subject at a first time point; and selecting the identified subject for participation in a clinical trial that comprises administration of a pharmaceutical composition comprising a therapeutically effective amount of a compound of formula (I), or a pharmaceutically acceptable salt, prodrug, or isomer thereof (e.g., CHS-131, e.g., using any of the doses or frequencies of administration described herein).

Methods of Predicting

Provided herein are methods of predicting the efficacy of a treatment in a subject that include: determining a level of neurofilament light chain protein level in a sample comprising cerebrospinal fluid, blood, serum, or plasma obtained from the subject; and determining that a treatment with a pharmaceutical composition comprising a therapeutically effective amount of a compound of formula (I), or a pharmaceutically acceptable salt, prodrug, or isomer thereof, is more likely to be effective in a subject having an elevated level of neurofilament light chain protein in the sample as compared to a reference level of neurofilament light chain protein, as compared to a subject not having an elevated level of neurofilament light chain protein in a sample comprising blood, serum, or plasma as compared to the reference level of neurofilament light chain protein.

In some aspects, the methods can include obtaining from the subject a second sample comprising cerebrospinal fluid, blood, serum, or plasma at a second time point and repeating the determining step.

Compositions and Kits

Also provided herein are compositions (e.g., pharmaceutical compositions) that include at least one compound of formula (I) of any of the compounds described herein and instructions for performing any of the methods described herein. In some embodiments, the compositions (e.g., pharmaceutical compositions) can be disposed in a sterile vial or a pre-loaded syringe.

In some embodiments, the compositions (e.g., pharmaceutical compositions) are formulated for different routes of administration (e.g., intracranial, intravenous, subcutaneous, or intramuscular). In some embodiments, the compositions (e.g., pharmaceutical compositions) can include a pharmaceutically acceptable salt (e.g., phosphate buffered saline). In some embodiments, the compositions (e.g., pharmaceutical compositions) can include a prodrug, or an isomer thereof. Single or multiple administrations of any of the pharmaceutical compositions described herein can be given to a subject depending on, for example: the dosage and frequency as required and tolerated by the patient. A dosage of the pharmaceutical composition should provide a sufficient quantity of the compound of formula (I) a pharmaceutically acceptable salt, prodrug, or an isomer thereof to effectively treat or ameliorate conditions, diseases or symptoms.

Also provided herein are kits containing one or more (e.g., at least 2, 3, 4, 5, 6, 7, 8, 9, 10, 12, 14, 16, 18, 20) of any of the pharmaceutical compositions described herein that include a therapeutically effective amount of a compound of formula (I), or a pharmaceutically acceptable salt, prodrug, or isomer thereof. In some embodiments, the kits can include instructions for performing any of the methods described herein. In some embodiments, the kits can include at least one dose of any of the compositions (e.g., pharmaceutical compositions) described herein. In some embodiments, the kits can provide a syringe for administering any of the pharmaceutical compositions described herein. The kits described herein are not so limited; other variations will be apparent to one of ordinary skill in the art.

The invention is further described in the following examples, which do not limit the scope of the invention described in the claims.

EXAMPLES

Example 1: INT131 is a Potent Upregulator of Adiponectin in Patients with Reduced Adiponectin Levels Method A randomized, double-blind, placebo-controlled, 24-week study was conducted in which adiponectin levels were measured. The study had a 2-week lead-in period, a 24-week double-blind treatment period and a 2-week follow up period. 367 subjects with type 2 diabetes (TD2)—a disease in which patient adiponectin levels are reduced—were randomly assigned to receive either 0.5, 1, 2 or 3 milligrams ("mg") of INT131 besylate, 45 mg of pioglitazone or placebo daily for 24 weeks. To measure adiponectin levels blood was drawn at Weeks 0, 2, 6, 12 and 24.

The results of this study demonstrated that 1, 2, and 3 mg doses of INT131 caused a statistically significant reduction of $HbA_{1c}$ levels as compared to placebo. Further, the study demonstrated that the 2 and 3 mg doses of INT131 reduced $HbA_{1c}$ levels at least as well as 45 mg of pioglitazone, which is an FDA approved treatment for TD2. See, DePaoli, et al. Diabetes Care 2014; 37:1918-1923. Thus, 2 and 3 mg doses of INT131 would be effective in treating TD2.

Adiponectin Results

At baseline (Week 0) mean adiponectin levels were 1.94 micrograms per milliliter ("µg/mL"). The mean adiponectin levels at baseline and Week 24, and the mean change in adiponectin levels from baseline (Week 0) to Week 24 are disclosed in Table 1, below. The standard deviation for samples tested in each group is listed in (parenthesis). Mean baseline adiponectin values were similar for the treatment groups.

TABLE 1

Changes in Adiponectin Serum Levels

| Mean Adiponectin (µg/mL) | Placebo | 0.5 mg INT131 | 1 mg INT131 | 2 mg INT131 | 3 mg INT131 | 45 mg Pioglitazone |
|---|---|---|---|---|---|---|
| n | 56 | 56 | 59 | 60 | 60 | 57 |
| Week 0 | 1.85 | 1.73 | 1.87 | 1.87 | 2.00 | 2.32 |
|  | (1.153) | (1.190) | (1.217) | (1.098) | (1.215) | (2.185) |
| Week 24 | 1.9 | 2.28 | 3.15 | 5.14 | 5.83 | 5.28 |
|  | (1.510) | (1.540) | (2.533) | (3.650) | (4.826) | (3.222) |
| Mean Change | 0.05 | 0.56 | 1.28 | 3.27 | 3.83 | 2.96 |
|  | (0.680) | (0.906) | (1.882) | (3.002) | (4.313) | (2.618) |

The treatment comparisons of 1 mg, 2 mg, and 3 mg doses of INT131 with placebo were statistically significant ($p \leq 0.0109$). This demonstrates that treatment with INT131 resulted in a statistically significant increase in adiponectin levels in patients suffering from a disease in which adiponectin levels are reduced (e.g. TD2). Thus, INT131 is therapeutically effective in treating patients with diseases (e.g. progressive supranuclear palsy) in which increasing lowered adiponectin levels may be beneficial.

Additionally, the treatment comparisons of 0.5 mg, 1 mg, and 3 mg doses of INT131 with pioglitazone 45 mg were statistically significant ($p \leq 0.0408$). Thus, the dose dependent increase of adiponectin levels by INT131 is independent from the increase resulting from pioglitazone.

CONCLUSIONS

The effect of treatment on serum adiponectin was assessed, enabling a more direct comparison of the relative potencies of INT131 and pioglitazone 45 mg as selective PPARγ modulators. The mean change in adiponectin from baseline to Week 24 with LOCF (last observation carried forward) was 0.05 µg/mL for the placebo group, 0.56 µg/mL for the INT131 0.5 mg group, 1.28 µg/mL for the INT131 1 mg group, 3.27 µg/mL for the 2 mg group, 3.83 µg/mL for the INT131 3 mg group, and 2.96 µg/mL for the pioglitazone 45 mg group. Therefore, in a manner quantitatively different from the effects on $HbA_{1c}$, where the INT131 dose roughly equivalent to pioglitazone 45 mg is between 2 mg and 3 mg, a dose of INT131 between 1 mg and 2 mg was equivalent to pioglitazone 45 mg for increasing adiponectin levels.

Surprisingly, administration of INT131 at either 2 or 3 mg resulted in a greater upregulation of serum adiponectin levels than did administration of at least 22 times the amount of pioglitazone. Small amounts of INT131 are at least as efficacious in treating diseases in which adiponectin levels are reduced as are other drugs which also increase adiponectin levels. Since INT131 crosses the blood brain barrier more readily than other PPARγ agonists, less INT131 is required to achieve the same increase adiponectin, and INT131 has fewer side effects than other PPARγ agonists, INT131 is a superior treatment for neurological diseases.

Administration of 1, 2, or 3 mg of INT131 treats patients suffering from diseases in which prevention or inhibition of adiponectin level decreases, or increasing adiponectin levels, may be beneficial (e.g. progressive supranuclear palsy).

Example 2: INT131 is a Potent Upregulator of Adiponectin in Healthy Subjects

Method

A study was conducted to determine the effect of INT131 on serum adiponectin levels. Thirty healthy subjects were randomly selected to receive either placebo, 0.1 mg INT131, 1 mg INT131 or 4 mg INT131 daily for 14 days. To measure adiponectin levels blood was drawn at Days 1, 4, 8 and 14.

Results

From Day 1 to Day 14 administration of placebo and 0.1 mg INT131 resulted in no significant change in serum adiponectin levels and further administration of 0.1 mg INT131 resulted in no significant change in adiponectin levels over placebo. See FIG. 1. However, administration of 1 mg or 4 mg INT131 resulted in a significant change in serum adiponectin levels over placebo and a significant change from Day 1 to Day 14. Thus, administration of INT131 is capable of upregulating adiponectin in healthy individuals (i.e. subjects without reduced adiponectin levels as a result of a disease or disorder).

Since INT131 upregulates adiponectin, even if a subject's adiponectin level has not been reduced by disease or disorder, upregulation of adiponectin in a subject with progressive supranuclear palsy may be beneficial in delaying progression of signs and symptoms of the disease.

Example 3: INT131 is Neuroprotective in Neurodegenerative Disease and is Useful in Treating PSP Methods 227 treatment-naive adult subjects (mean age 31 [range 18-50]; 65% female) were randomized into one of three arms: oral CHS-131 at 3 mg (n=76); oral CHS-131 at 1 mg (n=76); placebo (n=75), at 21 sites in Russia. 97% completed Part 1. Inclusion criteria: Relapsing Remitting Multiple Sclerosis (RRMS) for ≤3 years, ≥1 gadolinium-positive lesion within 1-year of enrollment, and an EDSS≤6 at screening. The patients underwent monthly MRI examinations with contrast to identify new inflammatory lesions. All Mills were read blinded at the Buffalo Neuroimaging Center (Buffalo, N.Y.). In addition to CE lesions the images were scored for cumulative new/enlarged T2 lesions, and serial cortical and whole brain volumetric analysis.

Results

CHS-131 treatment resulted in a dose-dependent reduction in cumulative CE lesions over 6 months (complete case analysis). 3 mg daily reduced CE lesion burden by 52% (4.2 lesions [LSMean 3.10]) vs. placebo (7.8 [LSMean 6.49]) (p=0.003). 1 mg treatment was less robust—21% reduction vs. placebo (7.6 [LSMean 5.15]) (p=ns). New/enlarged T2 lesions were reduced by 30% (3 mg)(p=0.0767) and 14% (1 mg)(p=ns) compared to placebo.

Figure 2:
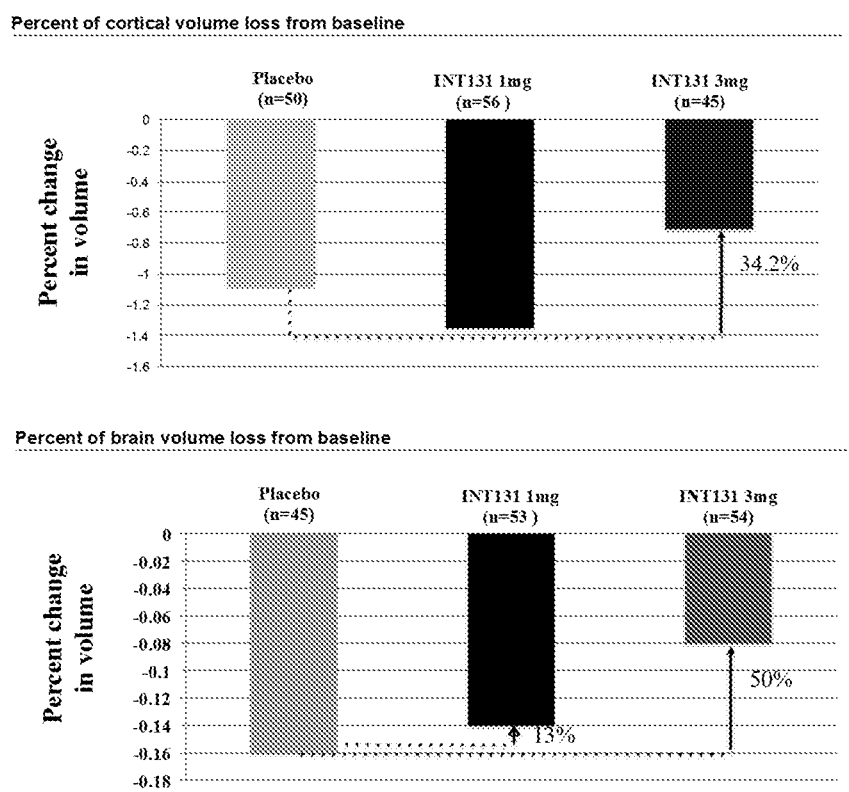
FIG. 2. Neuroprotective effects of CHS-131: subjects with a neurodegenerative disease (RRMS) administered 3 mg daily CHS-131 for six months had 34.2% less cortical volume loss and 50% less whole brain volume loss, when compared to placebo.

In addition to the dose-dependent anti-neuroinflammatory effects, CHS-131 treatment appeared to attenuate gray matter volume loss at 6-months. Compared to placebo, there was 34.2% less cortical volume loss and 50% less whole brain volume loss in the 3 mg cohort. Volume losses in the 1 mg treatment group were similar to placebo at 6 months. See, FIG. 2.

These data demonstrate that CHS-131 is neuroprotective. Therefore, administration of CHS-131 to a subject with progressive supranuclear palsy may be beneficial in delaying progression of signs and symptoms of the disease.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating progressive supranuclear palsy in a subject in need thereof comprising administering to the subject a pharmaceutical composition comprising a therapeutically effective amount of a compound of formula (I),

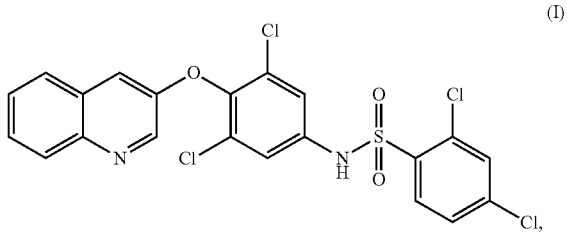 [SMILES: O=S(=O)(Nc1cc(Cl)c(Oc2cnc3ccccc3c2)c(Cl)c1)c1ccc(Cl)cc1Cl]

(I)

or a pharmaceutically acceptable salt thereof.

2. A method of treating the symptoms of progressive supranuclear palsy in a subject in need thereof comprising administering to the subject a pharmaceutical composition comprising a therapeutically effective amount of a compound of formula (I),

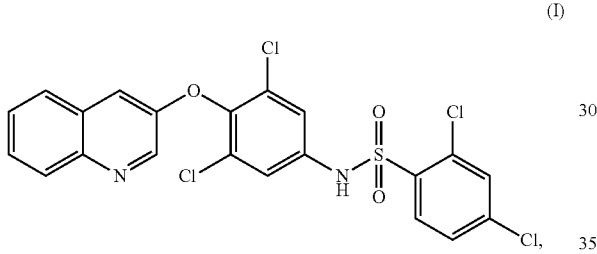

(I)

or a pharmaceutically acceptable salt thereof.

3. The method of claim 1, wherein the compound of formula (I), or a pharmaceutically acceptable salt thereof is given prophylactically.

4. The method of claim 3, wherein onset of progressive supranuclear palsy signs and symptoms are delayed.

5. The method of claim 1, wherein the compound of formula (I), or a pharmaceutically acceptable salt thereof is given to the subject in need thereof within one week of diagnosis of progressive supranuclear palsy.

6. The method of claim 5, wherein progression of progressive supranuclear palsy and symptoms thereof is impeded.

7. The method of claim 1, wherein the compound of formula (I) is in the form of a besylate salt.

8. The method of claim 1, wherein the therapeutically effective amount is from about 0.1 to about 15 milligrams.

9. The method of claim 8, wherein the therapeutically effective amount is from about 1 to about 10 milligrams.

10. The method of claim 9, wherein the therapeutically effective amount is from about 2 to about 6 milligrams.

11. The method of claim 10, wherein the therapeutically effective amount is about 3 milligrams.

12. The method of claim 1, wherein the pharmaceutical composition is administered to the subject daily.

13. The method of claim 2, wherein the compound of formula (I) is in the form of a besylate salt.

14. The method of claim 2, wherein the therapeutically effective amount is from about 0.1 to about 15 milligrams.

15. The method of claim 14, wherein the therapeutically effective amount is from about 1 to about 10 milligrams.

16. The method of claim 15, wherein the therapeutically effective amount is from about 2 to about 6 milligrams.

17. The method of claim 16, wherein the therapeutically effective amount is about 3 milligrams.

18. The method of claim 2, wherein the pharmaceutical composition is administered to the subject daily.

19. A method of treating progressive supranuclear palsy in a subject in need thereof comprising:
selecting a subject having an elevated level of neurofilament light chain protein in a sample from the subject compared to a reference level of neurofilament light chain protein;
wherein the sample comprises cerebrospinal fluid, blood, serum, or plasma; and
administering to the subject a pharmaceutical composition comprising a therapeutically effective amount of a compound of formula (I),

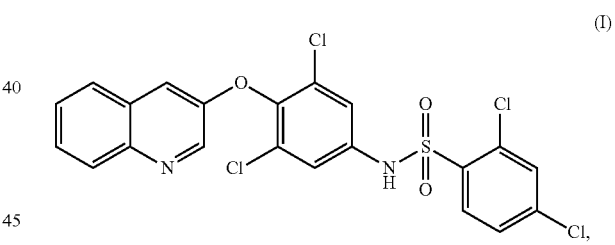

(I)

or a pharmaceutically acceptable salt thereof.

20. The method of claim 19, wherein the therapeutically effective amount is from about 1 to about 10 milligrams.

* * * * *

SEQUENCE LISTING

```
<160> NUMBER OF SEQ ID NOS: 4

<210> SEQ ID NO 1
<211> LENGTH: 1632
<212> TYPE: DNA
<213> ORGANISM: Human

<400> SEQUENCE: 1
atgagttcct tcagctacga gccgtactac tcgacctcct acaagcggcg ctacgtggag      60
acgccccggg tgcacatctc cagcgtgcgc agcggctaca gcaccgcacg ctcagcttac     120
tccagctact cggcgccggt gtcttcctcg ctgtccgtgc gccgcagcta ctcctccagc     180
tctggatcgt tgatgcccag tctggagaac ctcgacctga gccaggtagc cgccatcagc     240
aacgacctca agtccatccg cacgcaggag aaggcgcagc tccaggacct caatgaccgc     300
ttcgccagct tcatcgagcg cgtgcacgag ctggagcagc agaacaaggt cctggaagcc     360
gagctgctgg tgctgcgcca gaagcactcc gagccatccc gcttccgggc gctgtacgag     420
caggagatcc gcgacctgcg cctggcggcg gaagatgcca ccaacgagaa gcaggcgctc     480
cagggcgagc gcgaagggct ggaggagacc ctgcgcaacc tgcaggcgcg ctatgaagag     540
gaggtgctga gccgcgagga cgccgagggc cggctgatgg aagcgcgcaa aggcgccgac     600
gaggcggcgc tcgctcgcgc cgagctcgag aagcgcatcg acagcttgat ggacgaaatc     660
tcttttctga agaaagtgca cgaagaggag atcgccgaac tgcaggcgca gatccagtac     720
gcgcagatct ccgtggagat ggacgtgacc aagcccgacc tttccgccgc gctcaaggac     780
atccgcgcgc agtacgagaa gctggccgcc aagaacatgc agaacgctga ggaatggttc     840
aagagccgct tcaccgtgct gaccgagagc gccgccaaga caccgacgc cgtgcgcgcc     900 gccaaggacg aggtgtccga gagccgtcgt ctgctcaagg ccaagaccct ggaaatcgaa     960
gcatgccggg gcatgaatga agcgctggag aagcagctgc aggagctgga ggacaagcag    1020
```

```
aacgccgaca tcagcgctat gcaggacacg atcaacaaat tagaaaatga attgaggacc    1080
acaaagagtg aaatggcacg atacctaaaa gaataccaag acctcctcaa cgtgaagatg    1140
gctttggata ttgagattgc agcttacagg aaactcttgg aaggcgagga gacccgactc    1200
agtttcacca gcgtgggaag cataaccagt ggctactccc agagctccca ggtctttggc    1260
cgatctgcct acggcggttt acagaccagc tcctatctga tgtccacccg ctccttcccg    1320
tcctactaca ccagccatgt ccaagaggag cagatcgaag tggaggaaac cattgaggct    1380
gccaaggctg aggaagccaa ggatgagccc ccctctgaag agaagccga ggaggaggag    1440 aaggacaagg aagaggccga ggaagaggag gcagctgaag aggaagaagc tgccaaggaa    1500
gagtctgaag aagcaaaaga agaagaagaa ggaggtgaag gtgaagaagg agaggaaacc    1560
aaagaagctg aagaggagga gaagaaagtt gaaggtgctg gggaggaaca agcagctaag    1620
aagaaagatt ga                                                        1632

<210> SEQ ID NO 2
<211> LENGTH: 543
<212> TYPE: PRT
<213> ORGANISM: Human

<400> SEQUENCE: 2

Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
        35                  40                  45

Ser Ser Leu Ser Val Arg Arg Ser Tyr Ser Ser Ser Gly Ser Leu
    50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
            100                 105                 110

Gln Gln Asn Lys Val Leu Glu Ala Glu Leu Leu Val Leu Arg Gln Lys
        115                 120                 125

His Ser Glu Pro Ser Arg Phe Arg Ala Leu Tyr Glu Gln Glu Ile Arg
    130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
            180                 185                 190

Met Glu Ala Arg Lys Gly Ala Asp Glu Ala Ala Leu Ala Arg Ala Glu
        195                 200                 205

Leu Glu Lys Arg Ile Asp Ser Leu Met Asp Glu Ile Ser Phe Leu Lys
    210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                245                 250                 255

Ala Leu Lys Asp Ile Arg Ala Gln Tyr Glu Lys Leu Ala Ala Lys Asn
```

```
                260               265                270
Met Gln Asn Ala Glu Glu Trp Phe Lys Ser Arg Phe Thr Val Leu Thr
            275                 280                285

Glu Ser Ala Ala Lys Asn Thr Asp Ala Val Arg Ala Ala Lys Asp Glu
            290                 295                300

Val Ser Glu Ser Arg Arg Leu Leu Lys Ala Lys Thr Leu Glu Ile Glu
305                 310                315                320

Ala Cys Arg Gly Met Asn Glu Ala Leu Glu Lys Gln Leu Gln Glu Leu
                325                330                335

Glu Asp Lys Gln Asn Ala Asp Ile Ser Ala Met Gln Asp Thr Ile Asn
            340                 345                350

Lys Leu Glu Asn Glu Leu Arg Thr Thr Lys Ser Glu Met Ala Arg Tyr
            355                 360                365

Leu Lys Glu Tyr Gln Asp Leu Leu Asn Val Lys Met Ala Leu Asp Ile
            370                 375                380

Glu Ile Ala Ala Tyr Arg Lys Leu Leu Glu Gly Glu Glu Thr Arg Leu
385                 390                395                400

Ser Phe Thr Ser Val Gly Ser Ile Thr Ser Gly Tyr Ser Gln Ser Ser
                405                410                415

Gln Val Phe Gly Arg Ser Ala Tyr Gly Gly Leu Gln Thr Ser Ser Tyr
                420                425                430

Leu Met Ser Thr Arg Ser Phe Pro Ser Tyr Tyr Thr Ser His Val Gln
            435                 440                445

Glu Glu Gln Ile Glu Val Glu Glu Thr Ile Glu Ala Ala Lys Ala Glu
            450                 455                460

Glu Ala Lys Asp Glu Pro Pro Ser Glu Gly Glu Ala Glu Glu Glu Glu
465                 470                475                480

Lys Asp Lys Glu Glu Ala Glu Glu Glu Ala Glu Glu Glu Glu
                485                490                495

Ala Ala Lys Glu Glu Ser Glu Glu Ala Lys Glu Glu Glu Glu Gly Gly
                500                505                510

Glu Gly Glu Glu Gly Glu Glu Thr Lys Glu Ala Glu Glu Glu Glu Lys
            515                 520                525

Lys Val Glu Gly Ala Gly Glu Glu Gln Ala Ala Lys Lys Lys Asp
            530                 535                540

<210> SEQ ID NO 3
<211> LENGTH: 1632
<212> TYPE: DNA
<213> ORGANISM: Human

<400> SEQUENCE: 3
atgagttcgt tcggctacga tccgtacttt tcgacctcct acaagcggcg ctatgtggag      60
acgccccggg tgcacatctc cagcgtgcgc agcggctaca gcacggcgcg ctccgcgtac     120
tccagctact ccgcgccggt ctcctcctcg ctgtccgtgc gccgcagcta tcgtccagc      180 tctggctctt tgatgcccag cctggagaat ctcgatctga ccaggtagc cgccatcagc      240 aacgacctca gtctatccg cacacaagag aaggcacagc tgcaggacct caacgatcgc     300
ttcgccagct tcatcgagcg cgtgcacgag ctggagcagc agaacaaggt cctggaagcc     360
gagctgttgg tgctgcgcca gaaacactct gagccttccc gcttccgcgc cctgtacgag     420
caggagatcc gcgatctgcg gctggcagcg aagacgccca ctaacgagaa gcaggcgctg     480
cagggcgagc gcgaggggct ggaggagact ctgcgcaacc tgcaggctcg ctatgaggaa     540
```

```
gaagtgctga gccgcgagga cgccgagggc cggctgatgg aagcgcgcaa aggtgcggat    600
gaggccgcgc tcgcccgcgc cgagctggag aagcgcatcg acagcctgat ggacgagata    660
gctttcctga agaaggtgca cgaggaagag atcgccgagc tgcaggctca gatccagtat    720
gctcagatct ccgtggagat ggacgtgtcc tccaagcccg acctctccgc cgctctcaag    780
gacatccgcg ctcagtacga gaagctggcc gccaagaaca tgcagaacgc cgaagagtgg    840
ttcaagagcc gcttcaccgt gctaaccgag agcgccgcca gaacaccga cgctgtgcgc    900 gctgccaagg acgaggtgtc ggaaagccgc cgcctgctca aggctaagac cctggagatc    960
gaagcctgcc ggggtatgaa cgaagctctg gagaagcagc tgcaggagct agaggacaag   1020
cagaatgcag acattagcgc catgcaggac acaatcaaca aactggagaa tgagctgaga   1080
agcacgaaga gcgagatggc caggtacctg aaggagtacc aggacctcct caatgtcaag   1140
atggccttgg acatcgagat tgcagcttac agaaaactct tggaaggcga agagaccagg   1200
ctcagtttca ccagcgtggg tagcataacc agcggctact ctcagagctc gcaggtcttc   1260
ggccgttctg cttacagtgg cttgcagagc agctcctact tgatgtctgc tcgctctttc   1320
ccagcctact ataccagcca cgtccaggaa gagcagacag aggtcgagga gaccattgag   1380
gctacgaaag ctgaggaggc caaggatgag ccccccctctg aaggagaagc agaagaggag   1440
gagaaggaga agaggaggg agaggaagag gaaggcgctg aggaggaaga agctgccaag   1500
gatgagtctg aagcacacaaa agaagaagaa aaggtggtg agggtgagga ggaagacacc   1560
aaagaatctg aagaggaaga gaagaaagag gagagtgctg agaggagca ggtggctaag   1620 aagaaagatt ga                                                       1632

<210> SEQ ID NO 4
<211> LENGTH: 543
<212> TYPE: PRT
<213> ORGANISM: Human

<400> SEQUENCE: 4

Met Ser Ser Phe Gly Tyr Asp Pro Tyr Phe Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
        35                  40                  45

Ser Ser Leu Ser Val Arg Arg Ser Tyr Ser Ser Ser Gly Ser Leu
    50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
            100                 105                 110

Gln Gln Asn Lys Val Leu Glu Ala Glu Leu Leu Val Leu Arg Gln Lys
        115                 120                 125

His Ser Glu Pro Ser Arg Phe Arg Ala Leu Tyr Glu Gln Glu Ile Arg
    130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175
```

-continued

Arg Tyr Glu Glu Val Leu Ser Arg Glu Asp Ala Glu Gly Arg Leu
            180                 185                 190

Met Glu Ala Arg Lys Gly Ala Asp Glu Ala Ala Leu Ala Arg Ala Glu
            195                 200                 205

Leu Glu Lys Arg Ile Asp Ser Leu Met Asp Glu Ile Ala Phe Leu Lys
            210                 215                 220

Lys Val His Glu Glu Ile Ala Glu Leu Gln Ala Gln Ile Gln Tyr
225                 230                 235                 240

Ala Gln Ile Ser Val Glu Met Asp Val Ser Ser Lys Pro Asp Leu Ser
            245                 250                 255

Ala Ala Leu Lys Asp Ile Arg Ala Gln Tyr Glu Lys Leu Ala Ala Lys
            260                 265                 270

Asn Met Gln Asn Ala Glu Glu Trp Phe Lys Ser Arg Phe Thr Val Leu
            275                 280                 285

Thr Glu Ser Ala Ala Lys Asn Thr Asp Ala Val Arg Ala Ala Lys Asp
            290                 295                 300

Glu Val Ser Glu Ser Arg Arg Leu Leu Lys Ala Lys Thr Leu Glu Ile
305                 310                 315                 320

Glu Ala Cys Arg Gly Met Asn Glu Ala Leu Glu Lys Gln Leu Gln Glu
            325                 330                 335

Leu Glu Asp Lys Gln Asn Ala Asp Ile Ser Ala Met Gln Asp Thr Ile
            340                 345                 350

Asn Lys Leu Glu Asn Glu Leu Arg Ser Thr Lys Ser Glu Met Ala Arg
            355                 360                 365

Tyr Leu Lys Glu Tyr Gln Asp Leu Leu Asn Val Lys Met Ala Leu Asp
            370                 375                 380

Ile Glu Ile Ala Ala Tyr Arg Lys Leu Leu Glu Gly Glu Glu Thr Arg
385                 390                 395                 400

Leu Ser Phe Thr Ser Val Gly Ser Ile Thr Ser Gly Tyr Ser Gln Ser
            405                 410                 415

Ser Gln Val Phe Gly Arg Ser Ala Tyr Ser Gly Leu Gln Ser Ser Ser
            420                 425                 430

Tyr Leu Met Ser Ala Arg Ser Phe Pro Ala Tyr Tyr Thr Ser His Val
            435                 440                 445

Gln Glu Glu Gln Thr Glu Val Glu Glu Thr Ile Glu Ala Thr Lys Ala
            450                 455                 460

Glu Glu Ala Lys Asp Glu Pro Pro Ser Glu Gly Glu Ala Glu Glu Glu
465                 470                 475                 480

Glu Lys Glu Lys Glu Glu Gly Glu Glu Glu Gly Ala Glu Glu Glu
            485                 490                 495

Glu Ala Ala Lys Asp Glu Ser Glu Asp Thr Lys Glu Glu Glu Glu Gly
            500                 505                 510

Gly Glu Gly Glu Glu Gly Asp Thr Lys Glu Ser Glu Glu Glu Glu Lys
            515                 520                 525

Lys Glu Glu Ser Ala Gly Glu Glu Gln Val Ala Lys Lys Lys Asp
            530                 535                 540